United States Patent
Darrow et al.

(10) Patent No.: US 6,420,157 B1
(45) Date of Patent: Jul. 16, 2002

(54) ZYMOGEN ACTIVATION SYSTEM

(75) Inventors: Andrew Darrow, Lansdale, PA (US); Jenson Qi, Branchburg, NJ (US); Patricia Andrade-Grodon, Doylestown, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/386,642

(22) Filed: Aug. 31, 1999

Related U.S. Application Data

(63) Continuation-in-part of application No. 09/303,162, filed on Apr. 30, 1999.

(51) Int. Cl.$^7$ .................. C12N 9/64; C12N 15/62; C12N 15/63; C07K 19/00; A61K 38/48

(52) U.S. Cl. .................. 435/226; 435/69.7; 435/23; 435/174; 435/252.3; 435/320.1; 424/94.64; 536/23.2; 536/23.4

(58) Field of Search ............ 435/69.7, 23, 252.3, 435/320.1, 226

(56) References Cited

U.S. PATENT DOCUMENTS

| | | | |
|---|---|---|---|
| 4,992,373 A | 2/1991 | Bang et al. | 435/226 |
| 5,196,322 A | 3/1993 | Bang et al. | 435/69.7 |
| 5,200,340 A | 4/1993 | Foster et al. | 424/94.64 |
| 5,217,878 A | 6/1993 | Van Eekelen et al. | 435/69.1 |
| 5,270,178 A | 12/1993 | Gerlitz et al. | 435/69.1 |
| 5,278,062 A | 1/1994 | Samal et al. | 435/223 |
| 5,326,700 A | 7/1994 | Berg et al. | 435/240 |
| 5,342,762 A | 8/1994 | Mosher et al. | 435/69.3 |
| 5,665,566 A | 9/1997 | Lavallie | 435/693 |
| 5,834,247 A | 11/1998 | Comb et al. | 435/169.7 |

FOREIGN PATENT DOCUMENTS

| | | |
|---|---|---|
| EP | 0 887 414 | 12/1998 |
| WO | WO97/47737 | 6/1997 |
| WO | WO 98/49326 | 11/1998 |

OTHER PUBLICATIONS

Sherman, P.M. et al., "Identification of Tissue–type Plasminogen Activator–specific Plasminogen Activator Inhibitor–1 Mutants", The Journal of Biological Chemistry, Apr. 21, 1995, 9301–9306, vol. 270, No. 16.

Yu, J.X. et al., "Molecular Cloning: Tissue Specific Expression, and Cellular Localization of Human Prostasin mRNA", The Journal of Biological Chemistry, Jun. 2, 1995, 13483–13489, vol. 270, No. 22.

Kühn, Sabine and Zipfel, Peter F., "The Baculovirus Expression Vector pBSV–8His Directs Secretion of Histidine–Tagged Proteins", Gene, 1995, 225–229, vol. 12, Elsevier Science B.V.

Altschul, S. F., Gish, W., Miller, W., Myers, E. W., and Lipman, D. J. (1990). "Basic local alignment search tool". J. Mol. Bio., 215: 403–410.

(List continued on next page.)

*Primary Examiner*—Ponnathapu Achutamurthy
*Assistant Examiner*—William W. Moore
(74) *Attorney, Agent, or Firm*—John W. Wallen III

(57) ABSTRACT

We describe the DNA sequences encoding an expression vector system that will permit, through limited proteolysis, the activation of expressed zymogen precursor of (S1) serine proteases in a highly controlled and reproducible fashion. The processed expressed protein, once activated, is rendered in a form amenable to measuring the catalytic activity. This catalytic activity of the activated form, is often a more accurate representation of the mature S1 protease gene product relative to the unprocessed zymogen precursor. Thus, this series of zymogen activation constructs represents a significant system for the analysis and characterization of serine protease gene products.

16 Claims, 34 Drawing Sheets

OTHER PUBLICATIONS

Chen, Z.-L., Yoshida, S., Kato, K., Momota, Y., Suzuki, J., Tanaka, T., Ito, J., Nishino, H., Aimoto, S., Kiyama, H., and Shiosaka, S. (1995). Expression and activity–dependent changes of a novel limbic–serine protease gene in the hippocampus. J. Neurosci. 15, 5088–97.

Davie, E. W., Fujikawa, K., and Kisiel, W. (1991). The coagulation cascade: initiation, maintenance, and regulation. Biochemistry 30, 10363–70.

Hansson, L., Stroemqvist, M., Baeckman, A., Wallbrandt, P., Carlstein, A., and Egelrud, T. (1994). Clonding, expression, and characterization of stratum corneum chymotryptic enzyme. A skin–specific human serine proteinase. J. Biol. Chem. 269, 19420–6.

Huber, R., and Bode, W. (1978). Structural basis of the activation and action of trypsin. Acc. Chem. Res. 11, 114–22.

Inoue, M., Kanbe, N., Kurosawa, M., and Kido, H. (1998). Cloning and tissue distribution of a novel serine protease esp–1 from human eosinophils. Biochem. Biophys. Res. Commun. 252, 307–312.

Ishii, K., Hein, L., Kobilka, B., and Coughlin, S. R. (1993). Kinetics of thrombin receptor cleavage on intact cells. Relation to signaling. J. Biol. Chem. 268, 9780–6.

Kossiakoff, A. A., Chambers, J. L., Kay, L. M., and Stroud, R. M. (1977). Structure of bovine trypsinogen at 1.9 .ANG. resolution. Biochemistry 16, 654–64.

Kyte, J., and Doolittle, R. F. (1982). A simple method for displaying the hydropathic character of a protein. J. Mol. Biol. 157, 105–32.

Leytus, S. P., Loeb, K. R., Hagen, F. S., Kurachi, K., and Davie, E. W. (1988). A novel trypsin–like serine protease (hepsin) with a putative transmembrane domain expressed by human liver and hepatoma cells. Biochemistry 27, 1067–74.

Little, S. P., Dixon, E. P., Norris, F., Buckley, W., Becker, G. W., Johnson, M., Dobbins, J. R., Wyrick, T., Miller, J. R., Mackellar, W., Hepburn, D., Corvalin, J., Mcclure, D., Liu, X., Stpehenson, D., Clemens, J., and Johnstone, E. M. (1997). Zyme, a novel and potentially amyloidogenic enzyme cDNA isolated from Alzheimer's disease brain. J. Biol. Chem. 272, 25135–25142.

Martoglio, B., and Dobberstein, B. (1998). Signal sequences: more than just greasy peptides. Trends Cell Biol. 8, 410–415.

Matthews, B. W., Sigler, P. B., Henderson, R., and Blow, D. M. (1967). Three–dimensional structure of tosyl–.alpha.–chymotrypsin. Nature (London) 214, 652–6.

Nelson, P.S., Gan, L., Ferguson, C., Moss, P., Gelinas, R., Hood, L., and Wang, K. (1999). Molecular cloning and characterization of prostase, an androgen–regulated serine protease with prostate–restricted expression. Proc. Natl. Acad. Sci. U. S. A. 96, 3114–3119.

Pearson, W. R., and Lipman, D. J. (1988). Improved tools for biological sequence comparison. Proc. Natl. Acad. Sci. U. S. A. 85, 2444–8.

Proud, D., and Kaplan, A. P. (1988). Kinin formation: mechanisms and role in inflammatory disorders. Annu. Rev. Immunol. 6,, 49–83.

Rawlings, N. D., and Barrett, A. J. (1994). Families of serine peptidases. Methods Enzymol. 244, 19–61.

Reid, K. B. M., and Porter, R. R. (1981). The proteolytic activation systems of complement. Annual Review of Biochemistry 50, 433–464.

Stroud, R. M., Kay, L. M., and Dickerson, R. E. (1974). Structure of bovine trypsin. Electron density maps of the inhibited enzyme at 5 .ang. and 2.7 .ang. resolution. J. Mol. Biol. 83, 185–208.

Tachias, K., and Madison, E. L. (1996). Converting tissue–type plasminogen activator into a zymogen. J. Biol. Chem. 271, 2879–28752.

Takayama, T. K., Fujikawa, K., and Davie, E. W. (1997). Characterization of the precursor of prostate–specific antigen Activation by trypsin and by human glandular kallikrein. J. Biol. Chem. 272, 21582–21588.

Wang, Z.–m., Rubin, H., and Schechter, N. M. (1995). Production of active recombinant human chymase from a construct containing the enterokinase cleavage site of trypsinogen in place of the native propeptide sequence. Biol. Chem. Hoppe–Seyler 376, 681–4.

Yamashiro, K., Tsuruoka, N., Kodama, S., Tsujimoto, M., Yamamura, Y., Tanaka, T., Nakazato, H., and Yamaguchi, N. (1997). Molecular cloning of a novel trypsin–like serine protease (neurosin) preferentially expressed in brain. Biochim. Biophys. Acta 1350, 11–14.

Yoshida, S., Taniguchi, M., Hirata, A., and Shiosaka, S. (1998). Sequence analysis and expression of human neuropsin cDNA and gene. Gene 213, 9–16.

Yoshida, S., Taniguchi, M., Suemoto, T., Oka, T., He, X., and Shiosaka, S. (1998). cDNA cloning and expression of a novel serine protease, TLSP1. Biochim. Biophys. Acta 1399, 225–228.

Yu, J. X., Chao, L., and Chao, J. (1994). Prostasin is a novel human serine proteinase from seminal fluid. Purification, tissue distribution, and localization in prostate gland. J. Biol. Chem. 269, 18843–8.

C. T. N. Pham, D.A. Thomas J.D. Mercer and T. J. Ley Production of Fully Active Recombinant Murine Granzymen B in Yeast The Journal of Biological Chemistry vol. 273, No. 3, Issue of Jan. 19, 1998 pp. 1629–1698.

Ausubel, I.; Frederick, M. Short protocols in molecular biology. Molecular biology–Laboratory Manuals. 1997.

SEQ.ID.NO.:1

FIG. 2(A)

```
       Eco RI
     GAATTCACCACCATGGACAGCAAAGGTTCGTCGCAGAAATCCCGCCTGCT
  1  ----------+---------+---------+---------+---------+  50
     CTTAAGTGGTGGTACCTGTCGTTTCCAAGCAGCGTCTTTAGGGCGGACGA
            M  D  S  K  G  S  S  Q  K  S  R  L  L
            └─── Prolactin Signal Sequence ───
```

```
     CCTGCTGCTGGTGGTGTCAAATCTACTCTTGTGCCAGGGTGTGGTCTCCG
 51  ----------+---------+---------+---------+---------+  100
     GGACGACGACCACCACAGTTTAGATGAGAACACGGTCCCACACCAGAGGC
      L  L  L  V  V  S  N  L  L  L  C  Q  G  V  V  S
     ─────── Prolactin Signal Sequence ───────
```

```
                                   Not I
     ACTACAAGGACGACGACGACGTGGACGCGGCCGCTCTTGCTGCCCCCTTT
101  ----------+---------+---------+---------+---------+  150
     TGATGTTCCTGCTGCTGCTGCACCTGCGCCGGCGAGAACGACGGGGGAAA
      D  Y  K  D  D  D  D │ V  D │ A  A  A  L  A  A  P  F
      ─── FLAG ───              ─────── EK2 Pro ───
```

```
                                 Xba I      Not I
     GATGATGATGACAAGATCGTTGGGGGCTATGCTCTAGATAGCGGCCGCTT
151  ----------+---------+---------+---------+---------+  200
     CTACTACTACTGTTCTAGCAACCCCCGATACGAGATCTATCGCCGGCGAA
       D  D  D  D  K  I  V  G  G  Y  A  L │   *  │
      ─────── EK2 Pro ───────
```

```
     CCCTTTAGTGAGGGTTAATGCTTCGAGCAGACATGATAAGATACATTGAT
201  ----------+---------+---------+---------+---------+  250
     GGGAAATCACTCCCAATTACGAAGCTCGTCTGTACTATTCTATGTAACTA
     ═════════════════════════════════════════════════
                        SV40 Late pA
```

```
     GAGTTTGGACAAACCACAACTAGAATGCAGTGAAAAAAATGCTTTATTTG
251  ----------+---------+---------+---------+---------+  300
     CTCAAACCTGTTTGGTGTTGATCTTACGTCACTTTTTTTACGAAATAAAC
     ═════════════════════════════════════════════════
                        SV40 Late pA
```

```
     TGAAATTTGTGATGCTATTGCTTTATTTGTAACCATTATAAGCTGCAATA
301  ----------+---------+---------+---------+---------+  350
     ACTTTAAACACTACGATAACGAAATAAACATTGGTAATATTCGACGTTAT
     ═════════════════════════════════════════════════
                        SV40 Late pA
```

```
       HincII
     AACAAGTTGAC
351  ----------+- 361
     TTGTTCAACTG
     ───
```

FIG. 2(B)

SEQ.ID.NO.:2

```
        Eco RI                                        Not I
        GAATTCACCATGAATCCACTCCTGATCCTTACCTTTGTGGCGGCCGCTCT
  1     ----------+---------+---------+---------+---------+    50
        CTTAAGTGGTACTTAGGTGAGGACTAGGAATGGAAACACCGCCGGCGAGA
              | M  N  P  L  L  I  L  T  F  V| A  A  A  L
              |------ Trypsinogen Pre ------|

Xba I
        TGCTGCCCCCTTTGATGATGATGACAAGATCGTTGGGGGCTATTGTCTAG
 51     ----------+---------+---------+---------+---------+    100
        ACGACGGGGGAAACTACTACTACTGTTCTAGCAACCCCCGATAACAGATC
         A  A  P  F  D  D  D  D  K  I  V  G  G  Y  C  L|
        |------ EK3 Pro ------|

Not I
        ATACCCCTACGATGTGCCCGATTACGCCTAGCGGCCGCTTCCCTTTAGTG
 101    ----------+---------+---------+---------+---------+    150
        TATGGGGATGCTACACGGGCTAATGCGGATCGCCGGCGAAGGGAAATCAC
        | Y  P  Y  D  V  P  D  Y  A  *|
        |------ 1 X HA-TAG ------|                 ▬▬▬▬▬▬▬

AGGGTTAATGCTTCGAGCAGACATGATAAGATACATTGATGAGTTTGGAC
 151    ----------+---------+---------+---------+---------+    200
        TCCCAATTACGAAGCTCGTCTGTACTATTCTATGTAACTACTCAAACCTG
        ▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬
                            SV40 Late pA AAACCACAACTAGAATGCAGTGAAAAAAATGCTTTATTTGTGAAATTTGT
 201    ----------+---------+---------+---------+---------+    250
        TTTGGTGTTGATCTTACGTCACTTTTTTTACGAAATAAACACTTTAAACA
        ▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬
                            SV40 Late pA
                                                       HincII
        GATGCTATTGCTTTATTTGTAACCATTATAAGCTGCAATAAACAAGTTGA
 251    ----------+---------+---------+---------+---------+    300
        CTACGATAACGAAATAAACATTGGTAATATTCGACGTTATTTGTTCAACT
        ▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬
                             SV40 Late

SEQ.ID.NO.:3

```
     Eco RI
     GAATTCACCACCATGGACAGCAAAGGTTCGTCGCAGAAATCCCGCCTGCT
  1  ----------+---------+---------+---------+---------+  50
     CTTAAGTGGTGGTACCTGTCGTTTCCAAGCAGCGTCTTTAGGGCGGACGA
             M  D  S  K  G  S  S  Q  K  S  R  L  L
             └─── Prolactin Signal Sequence ───

CCTGCTGCTGGTGGTGTCAAATCTACTCTTGTGCCAGGGTGTGGTCTCCG
 51  ----------+---------+---------+---------+---------+ 100
     GGACGACGACCACCACAGTTTAGATGAGAACACGGTCCCACACCAGAGGC
      L  L  L  V  V  S  N  L  L  C  Q  G  V  V  S
     ─── Prolactin Signal Sequence ─────────────────┘

Not I
     ACTACAAGGACGACGACGACGTGGACGCGGCCGCTCTTGCTGCCCCCTTT
101  ----------+---------+---------+---------+---------+ 150
     TGATGTTCCTGCTGCTGCTGCACCTGCGCCGGCGAGAACGACGGGGGAAA
      D  Y  K  D  D  D  D  V  D  A  A  A  L  A  A  P  F
      ──── FLAG ────────┘  └─── ──── FXa Pro ────

Xba I
     ATCGAGGGGCGCATTGTGGAGGGCTCGGATCTAGATACCCCTACGATGTG
151  ----------+---------+---------+---------+---------+ 200
     TAGCTCCCCGCGTAACACCTCCCGAGCCTAGATCTATGGGGATGCTACAC
      I  E  G  R  I  V  E  G  S  D  L   Y  P  Y  D  V
                ──── FXa Pro ──────────┘ └────

CCCGATTACGCCGCTAGATACCCCTACGATGTGCCCGATTACGCCGCTAG
201  ----------+---------+---------+---------+---------+ 250
     GGGCTAATGCGGCGATCTATGGGGATGCTACACGGGCTAATGCGGCGATC
      P  D  Y  A  A  R  Y  P  Y  D  V  P  D  Y  A  A  R
      ──────────────────── 3 X HA-TAG ────────────────

ATACCACTACGATGTGCCCGATTACGCCGCTAGATACCCCTACGATGTGC
251  ----------+---------+---------+---------+---------+ 300
     TATGGTGATGCTACACGGGCTAATGCGGCGATCTATGGGGATGCTACACG
       Y  H  Y  D  V  P  D  Y  A  A  R  Y  P  Y  D  V
      ──────────────────── 3 X HA-TAG ────────────────

Not I
     CCGATTACGCCTAGCGGCCGCTTCCCTTTAGTGAGGGTTAATGCTTCGAG
301  ----------+---------+---------+---------+---------+ 350
     GGCTAATGCGGATCGCCGGCGAAGGGAAATCACTCCCAATTACGAAGCTC
      P  D  Y  A  *
```

FIG. 2(D)

```
     CAGACATGATAAGATACATTGATGAGTTTGGACAAACCACAACTAGAATG
351  --------+---------+---------+---------+---------+  400
     GTCTGTACTATTCTATGTAACTACTCAAACCTGTTTGGTGTTGATCTTAC
     ──────────────────────────────────────────────────
                          SV40 Late pA CAGTGAAAAAAATGCTTTATTTGTGAAATTTGTGATGCTATTGCTTTATT
401  --------+---------+---------+---------+---------+  450
     GTCACTTTTTTACGAAATAAACACTTTAAACACTACGATAACGAAATAA
     ──────────────────────────────────────────────────
                          SV40 Late pA
                          HincII
     TGTAACCATTATAAGCTGCAATAAACAAGTTGAC
451  --------+---------+---------+----  484
     ACATTGGTAATATTCGACGTTATTTGTTCAACTG
     ──────────────────────────────────
```

SEQ.ID.NO.:4

FIG. 2(E)

Eco RI
```
    GAATTCACCACCATGGACAGCAAAGGTTCGTCGCAGAAATCCCGCCTGCT
1   ---------+---------+---------+---------+---------+    50
    CTTAAGTGGTGGTACCTGTCGTTTCCAAGCAGCGTCTTTAGGGCGGACGA
              | M  D  S  K  G  S  S  Q  K  S  R  L  L
              └── Prolactin Signal Sequence ──────
```

```
     CCTGCTGCTGGTGGTGTCAAATCTACTCTTGTGCCAGGGTGTGGTCTCCG
51   ---------+---------+---------+---------+---------+    100
     GGACGACGACCACCACAGTTTAGATGAGAACACGGTCCCACACCAGAGGC
      L  L  L  V  V  S  N  L  L  L  C  Q  G  V  V  S |
      ──────── Prolactin Signal Sequence ───────────
```

```
                                  Not I
     ACTACAAGGACGACGACGACGTGGACGCGGCCGCTCTTGCTGCCCCCTTT
101  ---------+---------+---------+---------+---------+    150
     TGATGTTCCTGCTGCTGCTGCACCTGCGCCGGCGAGAACGACGGGGGAAA
      D  Y  K  D  D  D  D  V  D| A  A  A  L  A  A  P  F
      ──────── FLAG ──────────  ──────── EK1 Pro ──────
```

```
                                            Xba I
     GATGATGATGACAAGATCGTTGGGGGCTACAACTGTCTAGACATCACCAT
151  ---------+---------+---------+---------+---------+    200
     CTACTACTACTGTTCTAGCAACCCCCGATGTTGACAGATCTGTAGTGGTA
      D  D  D  D  K  I  V  G  G  Y  N  C  L| H  H  H
      ──────── EK1 Pro ──────────────────
```

```
               Not I
     CACCATCACTAGCGGCCGCTTCCCTTTAGTGAGGGTTAATGCTTCGAGCA
201  ---------+---------+---------+---------+---------+    250
     GTGGTAGTGATCGCCGGCGAAGGGAAATCACTCCCAATTACGAAGCTCGT
      H  H  H  *|                ▬▬▬▬▬▬▬▬▬▬▬▬▬▬▬▬▬▬▬▬
      6 X HIS-TAG
```

```
     GACATGATAAGATACATTGATGAGTTTGGACAAACCACAACTAGAATGCA
251  ---------+---------+---------+---------+---------+    300
     CTGTACTATTCTATGTAACTACTCAAACCTGTTTGGTGTTGATCTTACGT
     ▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬
                        SV40 Late pA
```

```
     GTGAAAAAAATGCTTTATTTGTGAAATTTGTGATGCTATTGCTTTATTTG
301  ---------+---------+---------+---------+---------+    350
     CACTTTTTTTACGAAATAAACACTTTAAACACTACGATAACGAAATAAAC
     ▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬
                        SV40 Late pA
```

FIG. 2(F)

```
                              HincII
         TAACCATTATAAGCTGCAATAAACAAGTTGAC
   351   ----------+----------+----------+--   382
         ATTGGTAATATTCGACGTTATTTGTTCAACTG
```

FIG. 2(G)

SEQ.ID.NO.:5

```
           Eco RI
           GAATTCACCACCATGGCTTTCCTCTGGCTCCTCTCCTGCTGGGCCCTCCT
      1    ---------+---------+---------+---------+---------+    50
           CTTAAGTGGTGGTACCGAAAGGAGACCGAGGAGAGGACGACCCGGGAGGA
                     M  A  F  L  W  L  L  S  C  W  A  L  L
                     |—————— Chymotrypsinogen Pre ——————

GGGTACCACCTTCGGCTGCGGGGTCCCCGACTACAAGGACGACGACGACG
     51    ---------+---------+---------+---------+---------+    100
           CCCATGGTGGAAGCCGACGCCCCAGGGGCTGATGTTCCTGCTGCTGCTGC
            G  T  T  F  G  C  G  V  P  D  Y  K  D  D  D  D
           ——Chymotrypsinogen Pre ————————|——————— FLAG ———————|

Not I
           CGGCCGCTCTTGCTGCCCCCTTTGATGATGATGACAAGATCGTTGGGGGC
    101    ---------+---------+---------+---------+---------+    150
           GCCGGCGAGAACGACGGGGGAAACTACTACTACTGTTCTAGCAACCCCCG
            A  A  A  L  A  A  P  F  D  D  D  D  K  I  V  G  G
                                 ———————— EK2 Pro ————————

Xba I                        Not I
           TATGCTCTAGACATCACCATCACCATCACTAGCGGCCGCTTCCCTTTAGT
    151    ---------+---------+---------+---------+---------+    200
           ATACGAGATCTGTAGTGGTAGTGGTAGTGATCGCCGGCGAAGGGAAATCA
            Y  A  L  | H  H  H  H  H  H  *  |
                    |——————— 6 X HIS-TAG ——————|       ▬▬▬▬▬▬▬▬

GAGGGTTAATGCTTCGAGCAGACATGATAAGATACATTGATGAGTTTGGA
    201    ---------+---------+---------+---------+---------+    250
           CTCCCAATTACGAAGCTCGTCTGTACTATTCTATGTAACTACTCAAACCT
           ▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬
                               SV40 Late pA CAAACCACAACTAGAATGCAGTGAAAAAAATGCTTTATTTGTGAAATTTG
    251    ---------+---------+---------+---------+---------+    300
           GTTTGGTGTTGATCTTACGTCACTTTTTTTACGAAATAAACACTTTAAAC
           ▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬
                               SV40 Late pA
                                                          Hinc
           TGATGCTATTGCTTTATTTGTAACCATTATAAGCTGCAATAAACAAGTTG
    301    ---------+---------+---------+---------+---------+    350
           ACTACGATAACGAAATAAACATTGGTAATATTCGACGTTATTTGTTCAAC
           ▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬▬
                               SV40 Late pA

SEQ.ID.NO.:6

```
          Eco RI
       GAATTCACCACCATGGCTTTCCTCTGGCTCCTCTCCTGCTGGGCCCTCCT
  1    ---------+---------+---------+---------+---------+   50
       CTTAAGTGGTGGTACCGAAAGGAGACCGAGGAGAGGACGACCCGGGAGGA
                      M  A  F  L  W  L  L  S  C  W  A  L  L
                     └───── Chymotrypsinogen Pre ─────

GGGTACCACCTTCGGCTGCGGGGTCCCCGACTACAAGGACGACGACGACG
  51   ---------+---------+---------+---------+---------+  100
       CCCATGGTGGAAGCCGACGCCCCAGGGGCTGATGTTCCTGCTGCTGCTGC
        G  T  T  F  G  C  G  V  P │ D  Y  K  D  D  D  D │
       ─ Chymotrypsinogen Pre ──  └─────── FLAG ───────

Not I
       CGGCCGCTCTTGCTGCCCCCTTTGATGATGATGACAAGATCGTTGGGGGC
 101   ---------+---------+---------+---------+---------+  150
       GCCGGCGAGAACGACGGGGGAAACTACTACTACTGTTCTAGCAACCCCCG
        A  A  A  L  A  A  P  F  D  D  D  D  K  I  V  G  G
       ───────────────────── EK2 Pro ─────────────────────

Xba I
       TATGCTCTAGATACCCCTACGATGTGCCCGATTACGCCGCTAGACATCAC
 151   ---------+---------+---------+---------+---------+  200
       ATACGAGATCTATGGGGATGCTACACGGGCTAATGCGGCGATCTGTAGTG
        Y  A  L │ Y  P  Y  D  V  P  D  Y  A  A  R  H  H
       ─────────└────────── HA 6 X HIS-TAG ──────────────

Not I
       CATCACCATCACTAGCGGCCGCTTCCCTTTAGTGAGGGTTAATGCTTCGA
 201   ---------+---------+---------+---------+---------+  250
       GTAGTGGTAGTGATCGCCGGCGAAGGGAAATCACTCCCAATTACGAAGCT
        H  H  H  H  * │
                     ─────────────────────────────────

GCAGACATGATAAGATACATTGATGAGTTTGGACAAACCACAACTAGAAT
 251   ---------+---------+---------+---------+---------+  300
       CGTCTGTACTATTCTATGTAACTACTCAAACCTGTTTGGTGTTGATCTTA
       ═══════════════════════════════════════════════════
                         SV40 Late pA GCAGTGAAAAAAATGCTTTATTTGTGAAATTTGTGATGCTATTGCTTTAT
 301   ---------+---------+---------+---------+---------+  350
       CGTCACTTTTTTTACGAAATAAACACTTTAAACACTACGATAACGAAATA
       ═══════════════════════════════════════════════════
                         SV40 Late pA
```

FIG. 2(I)

```
                                      HincII
        TTGTAACCATTATAAGCTGCAATAAACAAGTTGAC
351     ---------+---------+---------+-----   385
        AACATTGGTAATATTCGACGTTATTTGTTCAACTG
```

SEQ.ID.NO.:7

FIG. 3(A)

```
            Eco RI
     GAATTCACCACCATGGACAGCAAAGGTTCGTCGCAGAAATCCCGCCTGCT
  1  ---------+---------+---------+---------+---------+  50
     CTTAAGTGGTGGTACCTGTCGTTTCCAAGCAGCGTCTTTAGGGCGGACGA
          | M  D  S  K  G  S  S  Q  K  S  R  L  L
          └──────── Prolactin Signal Sequence ────────

CCTGCTGCTGGTGGTGTCAAATCTACTCTTGTGCCAGGGTGTGGTCTCCG
 51  ---------+---------+---------+---------+---------+  100
     GGACGACGACCACCACAGTTTAGATGAGAACACGGTCCCACACCAGAGGC
      L  L  L  V  V  S  N  L  L  L  C  Q  G  V  V  S |
      ─────────── Prolactin Signal Sequence ──────────|

Not I
     ACTACAAGGACGACGACGACGTGGACGCGGCCGCTCTTGCTGCCCCCTTT
101  ---------+---------+---------+---------+---------+  150
     TGATGTTCCTGCTGCTGCTGCACCTGCGCCGGCGAGAACGACGGGGGAAA
      D  Y  K  D  D  D  D | V  D | A  A  A  L  A  A  P  F
      ──── FLAG ─────────           ──────── EK2 Pro ────

Xba I
     GATGATGATGACAAGATCGTTGGGGGCTATGCTCTAGAGGCCGGTCAGTG
151  ---------+---------+---------+---------+---------+  200
     CTACTACTACTGTTCTAGCAACCCCCGATACGAGATCTCCGGCCAGTCAC
      D  D  D  D  K  I  V  G  G  Y  A  L | E | A  G  Q  W
      ──────────── EK2 Pro ──────────────

GCCCTGGCAGGTCAGCATCACCTATGAAGGCGTCCATGTGTGTGGTGGCT
201  ---------+---------+---------+---------+---------+  250
     CGGGACCGTCCAGTCGTAGTGGATACTTCCGCAGGTACACACACCACCGA
      P  W  Q  V  S  I  T  Y  E  G  V  H  V  C  G  G
      ──────────────── Prostasin.CDS ─────────────────

CTCTCGTGTCTGAGCAGTGGGTGCTGTCAGCTGCTCACTGCTTCCCCAGC
251  ---------+---------+---------+---------+---------+  300
     GAGAGCACAGACTCGTCACCCACGACAGTCGACGAGTGACGAAGGGGTCG
      S  L  V  S  E  Q  W  V  L  S  A  A  H  C  F  P  S
      ──────────────── Prostasin.CDS ─────────────────

GAGCACCACAAGGAAGCCTATGAGGTCAAGCTGGGGGCCCACCAGCTAGA
301  ---------+---------+---------+---------+---------+  350
     CTCGTGGTGTTCCTTCGGATACTCCAGTTCGACCCCCGGGTGGTCGATCT
      E  H  H  K  E  A  Y  E  V  K  L  G  A  H  Q  L  D
      ──────────────── Prostasin.CDS ─────────────────
```

FIG. 3(B)

```
       CTCCTACTCCGAGGACGCCAAGGTCAGCACCCTGAAGGACATCATCCCCC
351    ---------+---------+---------+---------+---------+    400
       GAGGATGAGGCTCCTGCGGTTCCAGTCGTGGGACTTCCTGTAGTAGGGGG
        S  Y  S  E  D  A  K  V  S  T  L  K  D  I  I  P  H
       ─────────────────── Prostasin.CDS ───────────────────

ACCCCAGCTACCTCCAGGAGGGCTCCCAGGGCGACATTGCACTCCTCCAA
401    ---------+---------+---------+---------+---------+    450
       TGGGGTCGATGGAGGTCCTCCCGAGGGTCCCGCTGTAACGTGAGGAGGTT
         P  S  Y  L  Q  E  G  S  Q  G  D  I  A  L  L  Q
       ─────────────────── Prostasin.CDS ───────────────────

CTCAGCAGACCCATCACCTTCTCCCGCTACATCCGGCCCATCTGCCTCCC
451    ---------+---------+---------+---------+---------+    500
       GAGTCGTCTGGGTAGTGGAAGAGGGCGATGTAGGCCGGGTAGACGGAGGG
         L  S  R  P  I  T  F  S  R  Y  I  R  P  I  C  L  P
       ─────────────────── Prostasin.CDS ───────────────────

TGCAGCCAACGCCTCCTTCCCCAACGGCCTCCACTGCACTGTCACTGGCT
501    ---------+---------+---------+---------+---------+    550
       ACGTCGGTTGCGGAGGAAGGGGTTGCCGGAGGTGACGTGACAGTGACCGA
         A  A  N  A  S  F  P  N  G  L  H  C  T  V  T  G
       ─────────────────── Prostasin.CDS ───────────────────

GGGGTCATGTGGCCCCCTCAGTGAGCCTCCTGACGCCCAAGCCACTGCAG
551    ---------+---------+---------+---------+---------+    600
       CCCCAGTACACCGGGGGAGTCACTCGGAGGACTGCGGGTTCGGTGACGTC
         W  G  H  V  A  P  S  V  S  L  L  T  P  K  P  L  Q
       ─────────────────── Prostasin.CDS ───────────────────

CAACTCGAGGTGCCTCTGATCAGTCGTGAGACGTGTAACTGCCTGTACAA
601    ---------+---------+---------+---------+---------+    650
       GTTGAGCTCCACGGAGACTAGTCAGCACTCTGCACATTGACGGACATGTT
         Q  L  E  V  P  L  I  S  R  E  T  C  N  C  L  Y  N
       ─────────────────── Prostasin.CDS ───────────────────

CATCGACGCCAAGCCTGAGGAGCCGCACTTTGTCCAAGAGGACATGGTGT
651    ---------+---------+---------+---------+---------+    700
       GTAGCTGCGGTTCGGACTCCTCGGCGTGAAACAGGTTCTCCTGTACCACA
          I  D  A  K  P  E  E  P  H  F  V  Q  E  D  M  V
       ─────────────────── Prostasin.CDS ───────────────────
```

FIG. 3(C)

```
      GTGCTGGCTATGTGGAGGGGGGCAAGGACGCCTGCCAGGGTGACTCTGGG
701   ---------+---------+---------+---------+---------+   750
      CACGACCGATACACCTCCCCCCGTTCCTGCGGACGGTCCCACTGAGACCC
       C  A  G  Y  V  E  G  G  K  D  A  C  Q  G  D  S  G
      ─────────────────── Prostasin.CDS ──────────────────

GGCCCACTCTCCTGCCCTGTGGAGGGTCTCTGGTACCTGACGGGCATTGT
751   ---------+---------+---------+---------+---------+   800
      CCGGGTGAGAGGACGGGACACCTCCCAGAGACCATGGACTGCCCGTAACA
         G  P  L  S  C  P  V  E  G  L  W  Y  L  T  G  I  V
      ─────────────────── Prostasin.CDS ──────────────────

GAGCTGGGGAGATGCCTGTGGGGCCCGCAACAGGCCTGGTGTGTACACTC
801   ---------+---------+---------+---------+---------+   850
      CTCGACCCCTCTACGGACACCCCGGGCGTTGTCCGGACCACACATGTGAG
         S  W  G  D  A  C  G  A  R  N  R  P  G  V  Y  T
      ─────────────────── Prostasin.CDS ──────────────────

TGGCCTCCAGCTATGCCTCCTGGATCCAAAGCAAGGTGACAGAACTCCAG
851   ---------+---------+---------+---------+---------+   900
      ACCGGAGGTCGATACGGAGGACCTAGGTTTCGTTCCACTGTCTTGAGGTC
         L  A  S  S  Y  A  S  W  I  Q  S  K  V  T  E  L  Q
      ─────────────────── Prostasin.CDS ──────────────────

CCTCGTGTGGTGCCCCAAACCCAGGAGTCCCAGCCCGACAGCAACCTCTG
901   ---------+---------+---------+---------+---------+   950
      GGAGCACACCACGGGGTTTGGGTCCTCAGGGTCGGGCTGTCGTTGGAGAC
         P  R  V  V  P  Q  T  Q  E  S  Q  P  D  S  N  L  C
      ─────────────────── Prostasin.CDS ──────────────────

Xba I
      TGGCAGCCACCTGGCCTTCAGCTCTAGACATCACCATCACCATCACTAGC
951   ---------+---------+---------+---------+---------+   1000
      ACCGTCGGTGGACCGGAAGTCGAGATCTGTAGTGGTAGTGGTAGTGATCG
         G  S  H  L  A  F  S │ S  R  H  H  H  H  H  H  * │
      ── Prostasin.CDS ──────┘         └─── 6 X HIS-TAG ──┘

Not I
      GGCCGCTTCCCTTTAGTGAGGGTTAATGCTTCGAGCAGACATGATAAGAT
1001  ---------+---------+---------+---------+---------+   1050
      CCGGCGAAGGGAAATCACTCCCAATTACGAAGCTCGTCTGTACTATTCTA
      ━━━━━━━━━━━━━━━━━━━━━━━━━━━━━━━━━━━━━━━━━━━━━━━━━
                          SV40 Late pA
```

FIG. 3(D)

```
     ACATTGATGAGTTTGGACAAACCACAACTAGAATGCAGTGAAAAAAATGC
1051 ----------+---------+---------+---------+---------+ 1100
     TGTAACTACTCAAACCTGTTTGGTGTTGATCTTACGTCACTTTTTTTACG
     ══════════════════════════════════════════════════
                          SV40 Late pA TTTATTTGTGAAATTTGTGATGCTATTGCTTTATTTGTAACCATTATAAG
1101 ----------+---------+---------+---------+---------+ 1150
     AAATAAACACTTTAAACACTACGATAACGAAATAAACATTGGTAATATTC
     ══════════════════════════════════════════════════
                          SV40 Late pA CTGCAATAAACAAGTTGAC
1151 ----------+--------  1169
     GACGTTATTTGTTCAACTG
     ═══════════════════
```

FIG. 4(A)

SEQ.ID.NO.:8

```
       Eco RI
       GAATTCACCACCATGGCTTTCCTCTGGCTCCTCTCCTGCTGGGCCCTCCT
  1    ----------+---------+---------+---------+---------+   50
       CTTAAGTGGTGGTACCGAAAGGAGACCGAGGAGAGGACGACCCGGGAGGA
                     M  A  F  L  W  L  L  S  C  W  A  L  L
                     |_____ Chymotrypsinogen Pre _____

GGGTACCACCTTCGGCTGCGGGGTCCCCGACTACAAGGACGACGACGACG
  51   ----------+---------+---------+---------+---------+   100
       CCCATGGTGGAAGCCGACGCCCCAGGGGCTGATGTTCCTGCTGCTGCTGC
        G  T  T  F  G  C  G  V  P | D  Y  K  D  D  D  D |
       ___Chymotrypsinogen Pre ___|____ FLAG _____|

Not I
       CGGCCGCTCTTGCTGCCCCCTTTGATGATGATGACAAGATCGTTGGGGGC
  101  ----------+---------+---------+---------+---------+   150
       GCCGGCGAGAACGACGGGGGAAACTACTACTACTGTTCTAGCAACCCCCG
        A  A  A  L  A  A  P  F  D  D  D  D  K  I  V  G  G
       _____ EK2 Pro _____

Xba I
       TATGCTCTAGAGGCCGGTCAGTGGCCCTGGCAGGTCAGCATCACCTATGA
  151  ----------+---------+---------+---------+---------+   200
       ATACGAGATCTCCGGCCAGTCACCGGGACCGTCCAGTCGTAGTGGATACT
        Y  A  L | E | A  G  Q  W  P  W  Q  V  S  I  T  Y  E
       _____ Prostasin.CDS _____

AGGCGTCCATGTGTGTGGTGGCTCTCTCGTGTCTGAGCAGTGGGTGCTGT
  201  ----------+---------+---------+---------+---------+   250
       TCCGCAGGTACACACACCACCGAGAGAGCACAGACTCGTCACCCACGACA
         G  V  H  V  C  G  G  S  L  V  S  E  Q  W  V  L
         _____ Prostasin.CDS _____

CAGCTGCTCACTGCTTCCCCAGCGAGCACCACAAGGAAGCCTATGAGGTC
  251  ----------+---------+---------+---------+---------+   300
       GTCGACGAGTGACGAAGGGGTCGCTCGTGGTGTTCCTTCGGATACTCCAG
        S  A  A  H  C  F  P  S  E  H  H  K  E  A  Y  E  V
        _____ Prostasin.CDS _____

AAGCTGGGGGCCCACCAGCTAGACTCCTACTCCGAGGACGCCAAGGTCAG
  301  ----------+---------+---------+---------+---------+   350
       TTCGACCCCCGGGTGGTCGATCTGAGGATGAGGCTCCTGCGGTTCCAGTC
         K  L  G  A  H  Q  L  D  S  Y  S  E  D  A  K  V  S
         _____ Prostasin.CDS _____
```

FIG. 4(B)

```
          CACCCTGAAGGACATCATCCCCCACCCCAGCTACCTCCAGGAGGGCTCCC
351       ----------+---------+---------+---------+---------+      400
          GTGGGACTTCCTGTAGTAGGGGGTGGGGTCGATGGAGGTCCTCCCGAGGG
            T  L  K  D  I  I  P  H  P  S  Y  L  Q  E  G  S
          ─────────────── Prostasin.CDS ───────────────

AGGGCGACATTGCACTCCTCCAACTCAGCAGACCCATCACCTTCTCCCGC
401       ----------+---------+---------+---------+---------+      450
          TCCCGCTGTAACGTGAGGAGGTTGAGTCGTCTGGGTAGTGGAAGAGGGCG
            Q  G  D  I  A  L  L  Q  L  S  R  P  I  T  F  S  R
          ─────────────── Prostasin.CDS ───────────────

TACATCCGGCCCATCTGCCTCCCTGCAGCCAACGCCTCCTTCCCCAACGG
451       ----------+---------+---------+---------+---------+      500
          ATGTAGGCCGGGTAGACGGAGGGACGTCGGTTGCGGAGGAAGGGGTTGCC
             Y  I  R  P  I  C  L  P  A  A  N  A  S  F  P  N  G
          ─────────────── Prostasin.CDS ───────────────

CCTCCACTGCACTGTCACTGGCTGGGGTCATGTGGCCCCCTCAGTGAGCC
501       ----------+---------+---------+---------+---------+      550
          GGAGGTGACGTGACAGTGACCGACCCCAGTACACCGGGGGAGTCACTCGG
             L  H  C  T  V  T  G  W  G  H  V  A  P  S  V  S
          ─────────────── Prostasin.CDS ───────────────

TCCTGACGCCCAAGCCACTGCAGCAACTCGAGGTGCCTCTGATCAGTCGT
551       ----------+---------+---------+---------+---------+      600
          AGGACTGCGGGTTCGGTGACGTCGTTGAGCTCCACGGAGACTAGTCAGCA
             L  L  T  P  K  P  L  Q  Q  L  E  V  P  L  I  S  R
          ─────────────── Prostasin.CDS ───────────────

GAGACGTGTAACTGCCTGTACAACATCGACGCCAAGCCTGAGGAGCCGCA
601       ----------+---------+---------+---------+---------+      650
          CTCTGCACATTGACGGACATGTTGTAGCTGCGGTTCGGACTCCTCGGCGT
             E  T  C  N  C  L  Y  N  I  D  A  K  P  E  E  P  H
          ─────────────── Prostasin.CDS ───────────────

CTTTGTCCAAGAGGACATGGTGTGTGCTGGCTATGTGGAGGGGGGCAAGG
651       ----------+---------+---------+---------+---------+      700
          GAAACAGGTTCTCCTGTACCACACACGACCGATACACCTCCCCCCGTTCC
             F  V  Q  E  D  M  V  C  A  G  Y  V  E  G  G  K
          ─────────────── Prostasin.CDS ───────────────
```

FIG. 4(C)

```
      ACGCCTGCCAGGGTGACTCTGGGGGCCCACTCTCCTGCCCTGTGGAGGGT
701   --------+---------+---------+---------+---------+   750
      TGCGGACGGTCCCACTGAGACCCCCGGGTGAGAGGACGGGACACCTCCCA
      D  A  C  Q  G  D  S  G  G  P  L  S  C  P  V  E  G
      ——————————————————— Prostasin.CDS ———————————————————

CTCTGGTACCTGACGGGCATTGTGAGCTGGGGAGATGCCTGTGGGGCCCG
751   --------+---------+---------+---------+---------+   800
      GAGACCATGGACTGCCCGTAACACTCGACCCCTCTACGGACACCCCGGGC
      L  W  Y  L  T  G  I  V  S  W  G  D  A  C  G  A  R
      ——————————————————— Prostasin.CDS ———————————————————

CAACAGGCCTGGTGTGTACACTCTGGCCTCCAGCTATGCCTCCTGGATCC
801   --------+---------+---------+---------+---------+   850
      GTTGTCCGGACCACACATGTGAGACCGGAGGTCGATACGGAGGACCTAGG
       N  R  P  G  V  Y  T  L  A  S  S  Y  A  S  W  I
      ——————————————————— Prostasin.CDS ———————————————————

AAAGCAAGGTGACAGAACTCCAGCCTCGTGTGGTGCCCCAAACCCAGGAG
851   --------+---------+---------+---------+---------+   900
      TTTCGTTCCACTGTCTTGAGGTCGGAGCACACCACGGGGTTTGGGTCCTC
       Q  S  K  V  T  E  L  Q  P  R  V  V  P  Q  T  Q  E
      ——————————————————— Prostasin.CDS ———————————————————

Xba I
      TCCCAGCCCGACAGCAACCTCTGTGGCAGCCACCTGGCCTTCAGCTCTAG
901   --------+---------+---------+---------+---------+   950
      AGGGTCGGGCTGTCGTTGGAGACACCGTCGGTGGACCGGAAGTCGAGATC
       S  Q  P  D  S  N  L  C  G  S  H  L  A  F  S│ S  R
      ——————————————————— Prostasin.CDS ———————————————

Not I
      ACATCACCATCACCATCACTAGCGGCCGCTTCCCTTTAGTGAGGGTTAAT
951   --------+---------+---------+---------+---------+   1000
      TGTAGTGGTAGTGGTAGTGATCGCCGGCGAAGGGAAATCACTCCCAATTA
      │H  H  H  H  H  H  *│                ▄▄▄▄▄▄▄▄▄▄▄▄▄▄
      ┴———— 6 X HIS-TAG ——┘

GCTTCGAGCAGACATGATAAGATACATTGATGAGTTTGGACAAACCACAA
1001  --------+---------+---------+---------+---------+   1050
      CGAAGCTCGTCTGTACTATTCTATGTAACTACTCAAACCTGTTTGGTGTT
      ▄▄▄▄▄▄▄▄▄▄▄▄▄▄▄▄▄▄▄▄▄▄▄▄▄▄▄▄▄▄▄▄▄▄▄▄▄▄▄▄▄▄▄▄▄▄▄▄▄▄
                         SV40 Late pA
```

FIG. 4(D)

```
     CTAGAATGCAGTGAAAAAAATGCTTTATTTGTGAAATTTGTGATGCTATT
1051 ---------+---------+---------+---------+---------+ 1100
     GATCTTACGTCACTTTTTTACGAAATAAACACTTTAAACACTACGATAA
     ═══════════════════════════════════════════════════
                           SV40 Late pA GCTTTATTTGTAACCATTATAAGCTGCAATAAACAAGTTGAC
1101 ---------+---------+---------+---------+-- 1142
     CGAAATAAACATTGGTAATATTCGACGTTATTTGTTCAACTG
     ═════════════════════════════════════════
```

FIG. 5(A)

SEQ.ID.NO.:9

```
         Eco RI
         GAATTCACCACCATGGACAGCAAAGGTTCGTCGCAGAAATCCCGCCTGCT
  1      ----------+---------+---------+---------+---------+  50
         CTTAAGTGGTGGTACCTGTCGTTTCCAAGCAGCGTCTTTAGGGCGGACGA
                        M  D  S  K  G  S  S  Q  K  S  R  L  L
                        └──── Prolactin Signal Sequence ─────

CCTGCTGCTGGTGGTGTCAAATCTACTCTTGTGCCAGGGTGTGGTCTCCG
 51      ----------+---------+---------+---------+---------+  100
         GGACGACGACCACCACAGTTTAGATGAGAACACGGTCCCACACCAGAGGC
          L  L  L  V  V  S  N  L  L  L  C  Q  G  V  V  S
         ─────────── Prolactin Signal Sequence ──────────┘

Not I
         ACTACAAGGACGACGACGACGTGGACGCGGCCGCTCTTGCTGCCCCCTTT
101      ----------+---------+---------+---------+---------+  150
         TGATGTTCCTGCTGCTGCTGCACCTGCGCCGGCGAGAACGACGGGGGAAA
          D  Y  K  D  D  D │ V  D │ A  A  A  L  A  A  P  F
         ──── FLAG ───────┘      └───────── EK1 Pro ───────

Xba I
         GATGATGATGACAAGATCGTTGGGGGCTACAACTGTCTAGAACCCCATTC
151      ----------+---------+---------+---------+---------+  200
         CTACTACTACTGTTCTAGCAACCCCCGATGTTGACAGATCTTGGGGTAAG
          D  D  D  D  K  I  V  G  G  Y  N  C  L │ E │ P  H  S
         ─────────── EK1 Pro ──────────────────┘

GCAGCCTTGGCAGGCGGCCTTGTTCCAGGGCCAGCAACTACTCTGTGGCG
201      ----------+---------+---------+---------+---------+  250
         CGTCGGAACCGTCCGCCGGAACAAGGTCCCGGTCGTTGATGAGACACCGC
          Q  P  W  Q  A  A  L  F  Q  G  Q  Q  L  L  C  G
         ─────────────────── Neuropsin.CDS ───────────────

GTGTCCTTGTAGGTGGCAACTGGGTCCTTACAGCTGCCCACTGTAAAAAA
251      ----------+---------+---------+---------+---------+  300
         CACAGGAACATCCACCGTTGACCCAGGAATGTCGACGGGTGACATTTTTT
          G  V  L  V  G  G  N  W  V  L  T  A  A  H  C  K  K
         ─────────────── Neuropsin.CDS ─────────────

CCGAAATACACAGTACGCCTGGGAGACCACAGCCTACAGAATAAAGATGG
301      ----------+---------+---------+---------+---------+  350
         GGCTTTATGTGTCATGCGGACCCTCTGGTGTCGGATGTCTTATTTCTACC
          P  K  Y  T  V  R  L  G  D  H  S  L  Q  N  K  D  G
         ─────────────── Neuropsin.CDS ─────────────
```

FIG. 5(B)

```
     CCCAGAGCAAGAAATACCTGTGGTTCAGTCCATCCCACACCCCTGCTACA
351  --------+---------+---------+---------+---------+  400
     GGGTCTCGTTCTTTATGGACACCAAGTCAGGTAGGGTGTGGGGACGATGT
      P  E  Q  E  I  P  V  V  Q  S  I  P  H  P  C  Y
      ─────────────── Neuropsin.CDS ───────────────
```

```
     ACAGCAGCGATGTGGAGGACCACAACCATGATCTGATGCTTCTTCAACTG
401  --------+---------+---------+---------+---------+  450
     TGTCGTCGCTACACCTCCTGGTGTTGGTACTAGACTACGAAGAAGTTGAC
      N  S  S  D  V  E  D  H  N  H  D  L  M  L  L  Q  L
      ─────────────── Neuropsin.CDS ───────────────
```

```
     CGTGACCAGGCATCCCTGGGGTCCAAAGTGAAGCCCATCAGCCTGGCAGA
451  --------+---------+---------+---------+---------+  500
     GCACTGGTCCGTAGGGACCCCAGGTTTCACTTCGGGTAGTCGGACCGTCT
      R  D  Q  A  S  L  G  S  K  V  K  P  I  S  L  A  D
      ─────────────── Neuropsin.CDS ───────────────
```

```
     TCATTGCACCCAGCCTGGCCAGAAGTGCACCGTCTCAGGCTGGGGCACTG
501  --------+---------+---------+---------+---------+  550
     AGTAACGTGGGTCGGACCGGTCTTCACGTGGCAGAGTCCGACCCCGTGAC
       H  C  T  Q  P  G  Q  K  C  T  V  S  G  W  G  T
      ─────────────── Neuropsin.CDS ───────────────
```

```
     TCACCAGTCCCCGAGAGAATTTTCCTGACACTCTCAACTGTGCAGAAGTA
551  --------+---------+---------+---------+---------+  600
     AGTGGTCAGGGGCTCTCTTAAAAGGACTGTGAGAGTTGACACGTCTTCAT
      V  T  S  P  R  E  N  F  P  D  T  L  N  C  A  E  V
      ─────────────── Neuropsin.CDS ───────────────
```

```
     AAAATCTTTCCCCAGAAGAAGTGTGAGGATGCTTACCCGGGGCAGATCAC
601  --------+---------+---------+---------+---------+  650
     TTTTAGAAAGGGGTCTTCTTCACACTCCTACGAATGGGCCCCGTCTAGTG
       K  I  F  P  Q  K  K  C  E  D  A  Y  P  G  Q  I  T
      ─────────────── Neuropsin.CDS ───────────────
```

```
     AGATGGCATGGTCTGTGCAGGCAGCAGCAAAGGGGCTGACACGTGCCAGG
651  --------+---------+---------+---------+---------+  700
     TCTACCGTACCAGACACGTCCGTCGTCGTTTCCCCGACTGTGCACGGTCC
       D  G  M  V  C  A  G  S  S  K  G  A  D  T  C  Q
      ─────────────── Neuropsin.CDS ───────────────
```

FIG. 5(C)

```
     GCGATTCTGGAGGCCCCCTGGTGTGTGATGGTGCACTCCAGGGCATCACA
701  ----------+---------+---------+---------+---------+ 750
     CGCTAAGACCTCCGGGGGACCACACACTACCACGTGAGGTCCCGTAGTGT
      G  D  S  G  G  P  L  V  C  D  G  A  L  Q  G  I  T
     ——————————————————— Neuropsin.CDS ———————————————————

TCCTGGGGCTCAGACCCCTGTGGGAGGTCCGACAAACCTGGCGTCTATAC
751  ----------+---------+---------+---------+---------+ 800
     AGGACCCCGAGTCTGGGGACACCCTCCAGGCTGTTTGGACCGCAGATATG
       S  W  G  S  D  P  C  G  R  S  D  K  P  G  V  Y  T
     ——————————————————— Neuropsin.CDS ———————————————————

CAACATCTGCCGCTACCTGGACTGGATCAAGAAGATCATAGGCAGCAAGG
801  ----------+---------+---------+---------+---------+ 850
     GTTGTAGACGGCGATGGACCTGACCTAGTTCTTCTAGTATCCGTCGTTCC
       N  I  C  R  Y  L  D  W  I  K  K  I  I  G  S  K
     ——————————————————— Neuropsin.CDS ———————————————————

Xba I                     Not I
     GCTCTAGACATCACCATCACCATCACTAGCGGCCGCTTCCCTTTAGTGAG
851  ----------+---------+---------+---------+---------+ 900
     CGAGATCTGTAGTGGTAGTGGTAGTGATCGCCGGCGAAGGGAAATCACTC
      G | S  R | H  H  H  H  H  H  *  |              ———
     ————————|———— 6 X HIS-TAG ————————|

GGTTAATGCTTCGAGCAGACATGATAAGATACATTGATGAGTTTGGACAA
901  ----------+---------+---------+---------+---------+ 950
     CCAATTACGAAGCTCGTCTGTACTATTCTATGTAACTACTCAAACCTGTT
     ═══════════════════════════════════════════════════
                          SV40 Late pA ACCACAACTAGAATGCAGTGAAAAAAATGCTTTATTTGTGAAATTTGTGA
951  ----------+---------+---------+---------+---------+ 1000
     TGGTGTTGATCTTACGTCACTTTTTTTACGAAATAAACACTTTAAACACT
     ═══════════════════════════════════════════════════
                          SV40 Late pA TGCTATTGCTTTATTTGTAACCATTATAAGCTGCAATAAACAAGTTGAC
1001 ----------+---------+---------+---------+--------- 1049
     ACGATAACGAAATAAACATTGGTAATATTCGACGTTATTTGTTCAACTG
     ══════════════════════════════════════════════════
                          SV40 Late pA
```

FIG. 6(A)

SEQ.ID.NO.:10

```
         Eco RI
         GAATTCACCACCATGGACAGCAAAGGTTCGTCGCAGAAATCCCGCCTGCT
   1     ---------+---------+---------+---------+---------+   50
         CTTAAGTGGTGGTACCTGTCGTTTCCAAGCAGCGTCTTTAGGGCGGACGA
           | M   D   S   K   G   S   S   Q   K   S   R   L   L
           └────── Prolactin Signal Sequence ──────

CCTGCTGCTGGTGGTGTCAAATCTACTCTTGTGCCAGGGTGTGGTCTCCG
  51     ---------+---------+---------+---------+---------+   100
         GGACGACGACCACCACAGTTTAGATGAGAACACGGTCCCACACCAGAGGC
           L   L   L   V   V   S   N   L   L   C   Q   G   V   V   S |
         ────── Prolactin Signal Sequence ──────

Not I
         ACTACAAGGACGACGACGACGTGGACGCGGCCGCTCTTGCTGCCCCCTTT
 101     ---------+---------+---------+---------+---------+   150
         TGATGTTCCTGCTGCTGCTGCACCTGCGCCGGCGAGAACGACGGGGGAAA
           D   Y   K   D   D   D   D | V   D | A   A   A   L   A   A   P   F
         ───── FLAG ─────            ───── EK1 Pro ─────

Xba I
         GATGATGATGACAAGATCGTTGGGGGCTACAACTGTCTAGAAAAGCACTC
 151     ---------+---------+---------+---------+---------+   200
         CTACTACTACTGTTCTAGCAACCCCCGATGTTGACAGATCTTTTCGTGAG
           D   D   D   D   K   I   V   G   G   Y   N   C   L | E   K   H   S
         ─────── EK1 Pro ───────

CCAGCCCTGGCAGGCAGCCCTGTTCGAGAAGACGCGGCTACTCTGTGGGG
 201     ---------+---------+---------+---------+---------+   250
         GGTCGGGACCGTCCGTCGGGACAAGCTCTTCTGCGCCGATGAGACACCCC
           Q   P   W   Q   A   A   L   F   E   K   T   R   L   L   C   G
         ─────── Protease O.CDS ───────

CGACGCTCATCGCCCCCAGATGGCTCCTGACAGCAGCCCACTGCCTCAAG
 251     ---------+---------+---------+---------+---------+   300
         GCTGCGAGTAGCGGGGGTCTACCGAGGACTGTCGTCGGGTGACGGAGTTC
           A   T   L   I   A   P   R   W   L   L   T   A   A   H   C   L   K
         ─────── Protease O.CDS ───────

CCCCGCTACATAGTTCACCTGGGGCAGCACAACCTCCAGAAGGAGGAGGG
 301     ---------+---------+---------+---------+---------+   350
         GGGGCGATGTATCAAGTGGACCCCGTCGTGTTGGAGGTCTTCCTCCTCCC
           P   R   Y   I   V   H   L   G   Q   H   N   L   Q   K   E   E   G
         ─────── Protease O.CDS ───────
```

FIG. 6(B)

```
           CTGTGAGCAGACCCGGACAGCCACTGAGTCCTTCCCCCACCCCGGCTTCA
351        ---------+---------+---------+---------+---------+    400
           GACACTCGTCTGGGCCTGTCGGTGACTCAGGAAGGGGGTGGGGCCGAAGT
            C  E  Q  T  R  T  A  T  E  S  F  P  H  P  G  F
           ─────────────── Protease O.CDS ───────────────

ACAACAGCCTCCCCAACAAAGACCACCGCAATGACATCATGCTGGTGAAG
401        ---------+---------+---------+---------+---------+    450
           TGTTGTCGGAGGGGTTGTTTCTGGTGGCGTTACTGTAGTACGACCACTTC
            N  N  S  L  P  N  K  D  H  R  N  D  I  M  L  V  K
           ─────────────── Protease O.CDS ───────────────

ATGGCATCGCCAGTCTCCATCACCTGGGCTGTGCGACCCCTCACCCTCTC
451        ---------+---------+---------+---------+---------+    500
           TACCGTAGCGGTCAGAGGTAGTGGACCCGACACGCTGGGGAGTGGGAGAG
              M  A  S  P  V  S  I  T  W  A  V  R  P  L  T  L  S
           ─────────────── Protease O.CDS ───────────────

CTCACGCTGTGTCACTGCTGGCACCAGCTGCCTCATTTCCGGCTGGGGCA
501        ---------+---------+---------+---------+---------+    550
           GAGTGCGACACAGTGACGACCGTGGTCGACGGAGTAAAGGCCGACCCCGT
             S  R  C  V  T  A  G  T  S  C  L  I  S  G  W  G
           ─────────────── Protease O.CDS ───────────────

GCACGTCCAGCCCCCAGTTACGCCTGCCTCACACCTTGCGATGCGCCAAC
551        ---------+---------+---------+---------+---------+    600
           CGTGCAGGTCGGGGGTCAATGCGGACGGAGTGTGGAACGCTACGCGGTTG
              S  T  S  S  P  Q  L  R  L  P  H  T  L  R  C  A  N
           ─────────────── Protease O.CDS ───────────────

ATCACCATCATTGAGCACCAGAAGTGTGAGAACGCCTACCCCGGCAACAT
601        ---------+---------+---------+---------+---------+    650
           TAGTGGTAGTAACTCGTGGTCTTCACACTCTTGCGGATGGGGCCGTTGTA
             I  T  I  I  E  H  Q  K  C  E  N  A  Y  P  G  N  I
           ─────────────── Protease O.CDS ───────────────

CACAGACACCATGGTGTGTGCCAGCGTGCAGGAAGGGGGCAAGGACTCCT
651        ---------+---------+---------+---------+---------+    700
           GTGTCTGTGGTACCACACACGGTCGCACGTCCTTCCCCCGTTCCTGAGGA
             T  D  T  M  V  C  A  S  V  Q  E  G  G  K  D  S
           ─────────────── Protease O.CDS ───────────────
```

FIG. 6(C)

```
      GCCAGGGTGACTCCGGGGGCCCTCTGGTCTGTAACCAGTCTCTTCAAGGC
 701  ---------+---------+---------+---------+---------+  750
      CGGTCCCACTGAGGCCCCCGGGAGACCAGACATTGGTCAGAGAAGTTCCG
       C  Q  G  D  S  G  G  P  L  V  C  N  Q  S  L  Q  G
      ─────────────────── Protease O.CDS ───────────────

ATTATCTCCTGGGGCCAGGATCCGTGTGCGATCACCCGAAAGCCTGGTGT
 751  ---------+---------+---------+---------+---------+  800
      TAATAGAGGACCCCGGTCCTAGGCACACGCTAGTGGGCTTTCGGACCACA
        I  I  S  W  G  Q  D  P  C  A  I  T  R  K  P  G  V
      ─────────────────── Protease O.CDS ───────────────

CTACACGAAAGTCTGCAAATATGTGGACTGGATCCAGGAGACGATGAAGA
 801  ---------+---------+---------+---------+---------+  850
      GATGTGCTTTCAGACGTTTATACACCTGACCTAGGTCCTCTGCTACTTCT
        Y  T  K  V  C  K  Y  V  D  W  I  Q  E  T  M  K
      ─────────────────── Protease O.CDS ───────────────

Xba I                          Not I
      ACAATTCTAGACATCACCATCACCATCACTAGCGGCCGCTTCCCTTTAGT
 851  ---------+---------+---------+---------+---------+  900
      TGTTAAGATCTGTAGTGGTAGTGGTAGTGATCGCCGGCGAAGGGAAATCA
        N  N │ S  R │ H  H  H  H  H  H  * │         ━━━━━
      ───────    ── 6 X HIS-TAG ──────────

GAGGGTTAATGCTTCGAGCAGACATGATAAGATACATTGATGAGTTTGGA
 901  ---------+---------+---------+---------+---------+  950
      CTCCCAATTACGAAGCTCGTCTGTACTATTCTATGTAACTACTCAAACCT
      ━━━━━━━━━━━━━━━━━━━━━━━━━━━━━━━━━━━━━━━━━━━━━━━━━
                            SV40 Late pA CAAACCACAACTAGAATGCAGTGAAAAAAATGCTTTATTTGTGAAATTTG
 951  ---------+---------+---------+---------+---------+ 1000
      GTTTGGTGTTGATCTTACGTCACTTTTTTTACGAAATAAACACTTTAAAC
      ━━━━━━━━━━━━━━━━━━━━━━━━━━━━━━━━━━━━━━━━━━━━━━━━━
                            SV40 Late pA TGATGCTATTGCTTTATTTGTAACCATTATAAGCTGCAATAAACAAGTTG
1001  ---------+---------+---------+---------+---------+ 1050
      ACTACGATAACGAAATAAACATTGGTAATATTCGACGTTATTTGTTCAAC
      ━━━━━━━━━━━━━━━━━━━━━━━━━━━━━━━━━━━━━━━━━━━━━━━━━
                            SV40 Late pA

AC
1051  --  1052
      TG
```

Protease: PFEK1-neuropsin-6XHIS

Protease: PFEK1-protease O-6XHIS

Protease: CFEK2-Protease F-6XHIS

Protease: PFEK-MH2-6XHIS

SEQ.ID.NO.:53

FIG. 13(A)

```
      Eco RI
      GAATTCACCACCATGGCTTTCCTCTGGCTCCTCTCCTGCTGGGCCCTCCT
  1   ---------+---------+---------+---------+---------+   50
      CTTAAGTGGTGGTACCGAAAGGAGACCGAGGAGAGGACGACCCGGGAGGA
            M  A  F  L  W  L  L  S  C  W  A  L  L
              └─── Chymotrypsinogen Pre ───────
```

```
      GGGTACCACCTTCGGCTGCGGGGTCCCCGACTACAAGGACGACGACGACG
 51   ---------+---------+---------+---------+---------+  100
      CCCATGGTGGAAGCCGACGCCCCAGGGGCTGATGTTCCTGCTGCTGCTGC
       G  T  T  F  G  C  G  V  P │ D  Y  K  D  D  D  D │
      ──Chymotrypsinogen Pre ─────┘    ─── FLAG ─────────
```

```
          Not I
      CGGCCGCTCTTGCTGCCCCCTTTGATGATGATGACAAGATCGTTGGGGGC
 101  ---------+---------+---------+---------+---------+  150
      GCCGGCGAGAACGACGGGGGAAACTACTACTACTGTTCTAGCAACCCCCG
       A  A  A  L  A  A  P  F  D  D  D  D  K  I  V  G  G
      ──────────────── EK2 Pro ──────────
```

```
           Xba I
      TATGCTCTAGAACTCGGGCGTTGGCCGTGGCAGGGGAGCCTGCGCCTGTG
 151  ---------+---------+---------+---------+---------+  200
      ATACGAGATCTTGAGCCCGCAACCGGCACCGTCCCCTCGGACGCGGACAC
       Y  A  L │ E │ L  G  R  W  P  W  Q  G  S  L  R  L  W
      ─────────┘   └──────── Protease F.CDS ────────
```

```
      GGATTCCCACGTATGCGGAGTGAGCCTGCTCAGCCACCGCTGGGCACTCA
 201  ---------+---------+---------+---------+---------+  250
      CCTAAGGGTGCATACGCCTCACTCGGACGAGTCGGTGGCGACCCGTGAGT
       D  S  H  V  C  G  V  S  L  L  S  H  R  W  A  L
      ──────────── Protease F.CDS ────────
```

```
      CGGCGGCGCACTGCTTTGAAACCTATAGTGACCTTAGTGATCCCTCCGGG
 251  ---------+---------+---------+---------+---------+  300
      GCCGCCGCGTGACGAAACTTTGGATATCACTGGAATCACTAGGGAGGCCC
       T  A  A  H  C  F  E  T  Y  S  D  L  S  D  P  S  G
      ──────────── Protease F.CDS ────────
```

```
      TGGATGGTCCAGTTTGGCCAGCTGACTTCCATGCCATCCTTCTGGAGCCT
 301  ---------+---------+---------+---------+---------+  350
      ACCTACCAGGTCAAACCGGTCGACTGAAGGTACGGTAGGAAGACCTCGGA
       W  M  V  Q  F  G  Q  L  T  S  M  P  S  F  W  S  L
      ──────────── Protease F.CDS ────────
```

FIG. 13(B)

```
    GCAGGCCTACTACAACCGTTACTTCGTATCGAATATCTATCTGAGCCCTC
351 --------+---------+---------+---------+---------+ 400
    CGTCCGGATGATGTTGGCAATGAAGCATAGCTTATAGATAGACTCGGGAG
     Q  A  Y  Y  N  R  Y  F  V  S  N  I  Y  L  S  P
     ─────────── Protease F.CDS ───────────

GCTACCTGGGGAATTCACCCTATGACATTGCCTTGGTGAAGCTGTCTGCA
401 --------+---------+---------+---------+---------+ 450
    CGATGGACCCCTTAAGTGGGATACTGTAACGGAACCACTTCGACAGACGT
      R  Y  L  G  N  S  P  Y  D  I  A  L  V  K  L  S  A
     ─────────── Protease F.CDS ───────────

CCTGTCACCTACACTAAACACATCCAGCCCATCTGTCTCCAGGCCTCCAC
451 --------+---------+---------+---------+---------+ 500
    GGACAGTGGATGTGATTTGTGTAGGTCGGGTAGACAGAGGTCCGGAGGTG
     P  V  T  Y  T  K  H  I  Q  P  I  C  L  Q  A  S  T
     ─────────── Protease F.CDS ───────────

ATTTGAGTTTGAGAACCGGACAGACTGCTGGGTGACTGGCTGGGGGTACA
501 --------+---------+---------+---------+---------+ 550
    TAAACTCAAACTCTTGGCCTGTCTGACGACCCACTGACCGACCCCCATGT
      F  E  F  E  N  R  T  D  C  W  V  T  G  W  G  Y
     ─────────── Protease F.CDS ───────────

TCAAAGAGGATGAGGCACTGCCATCTCCCCACACCCTCCAGGAAGTTCAG
551 --------+---------+---------+---------+---------+ 600
    AGTTTCTCCTACTCCGTGACGGTAGAGGGGTGTGGGAGGTCCTTCAAGTC
     I  K  E  D  E  A  L  P  S  P  H  T  L  Q  E  V  Q
     ─────────── Protease F.CDS ───────────

GTCGCCATCATAAACAACTCTATGTGCAACCACCTCTTCCTCAAGTACAG
601 --------+---------+---------+---------+---------+ 650
    CAGCGGTAGTATTTGTTGAGATACACGTTGGTGGAGAAGGAGTTCATGTC
      V  A  I  I  N  N  S  M  C  N  H  L  F  L  K  Y  S
     ─────────── Protease F.CDS ───────────

TTTCCGCAAGGACATCTTTGGAGACATGGTTTGTGCTGGCAATGCCCAAG
651 --------+---------+---------+---------+---------+ 700
    AAAGGCGTTCCTGTAGAAACCTCTGTACCAAACACGACCGTTACGGGTTC
      F  R  K  D  I  F  G  D  M  V  C  A  G  N  A  Q
     ─────────── Protease F.CDS ───────────
```

FIG. 13(C)

```
     GCGGGAAGGATGCCTGCTTCGGTGACTCAGGTGGACCCTTGGCCTGTAAC
701  --------+---------+---------+---------+---------+   750
     CGCCCTTCCTACGGACGAAGCCACTGAGTCCACCTGGGAACCGGACATTG
      G  G  K  D  A  C  F  G  D  S  G  G  P  L  A  C  N
     ———————————————— Protease F.CDS ————————————————
```

```
     AAGAATGGACTGTGGTATCAGATTGGAGTCGTGAGCTGGGGAGTGGGCTG
751  --------+---------+---------+---------+---------+   800
     TTCTTACCTGACACCATAGTCTAACCTCAGCACTCGACCCCTCACCCGAC
       K  N  G  L  W  Y  Q  I  G  V  V  S  W  G  V  G  C
     ———————————————— Protease F.CDS ————————————————
```

```
     TGGTCGGCCCAATCGGCCCGGTGTCTACACCAATATCAGCCACCACTTTG
801  --------+---------+---------+---------+---------+   850
     ACCAGCCGGGTTAGCCGGGCCACAGATGTGGTTATAGTCGGTGGTGAAAC
        G  R  P  N  R  P  G  V  Y  T  N  I  S  H  H  F
     ———————————————— Protease F.CDS ————————————————
```

```
     AGTGGATCCAGAAGCTGATGGCCCAGAGTGGCATGTCCCAGCCAGACCCC
851  --------+---------+---------+---------+---------+   900
     TCACCTAGGTCTTCGACTACCGGGTCTCACCGTACAGGGTCGGTCTGGGG
      E  W  I  Q  K  L  M  A  Q  S  G  M  S  Q  P  D  P
     ———————————————— Protease F.CDS ————————————————
```

```
         Xba I                              Not I
     TCCTGGTCTAGACATCACCATCACCATCACTAGCGGCCGCTTCCCTTTAG
901  --------+---------+---------+---------+---------+   950
     AGGACCAGATCTGTAGTGGTAGTGGTAGTGATCGCCGGCGAAGGGAAATC
      S  W │ S  R │ H  H  H  H  H  H  * │
               ————— 6 X HIS-TAG —————
```

```
     TGAGGGTTAATGCTTCGAGCAGACATGATAAGATACATTGATGAGTTTGG
951  --------+---------+---------+---------+---------+   1000
     ACTCCCAATTACGAAGCTCGTCTGTACTATTCTATGTAACTACTCAAACC
     ════════════════════════════════════════════════════
                          SV40 Late pA
```

```
     ACAAACCACAACTAGAATGCAGTGAAAAAAATGCTTTATTTGTGAAATTT
1001 --------+---------+---------+---------+---------+   1050
     TGTTTGGTGTTGATCTTACGTCACTTTTTTTACGAAATAAACACTTTAAA
     ════════════════════════════════════════════════════
                          SV40 Late pA
```

```
     GTGATGCTATTGCTTTATTTGTAACCATTATAAGCTGCAATAAACAAGTT
1051 --------+---------+---------+---------+---------+   1100
     CACTACGATAACGAAATAAACATTGGTAATATTCGACGTTATTTGTTCAA
     ════════════════════════════════════════════════════
                          SV40 Late pA
```

FIG. 13(D)

```
           GAC
1101       ---       1103
           CTG
```

SEQ.ID.NO.:54 FIG. 14(A)

```
     Eco RI
     GAATTCACCACCATGGACAGCAAAGGTTCGTCGCAGAAATCCCGCCTGCT
1    ---------+---------+---------+---------+---------+  50
     CTTAAGTGGTGGTACCTGTCGTTTCCAAGCAGCGTCTTTAGGGCGGACGA
            | M   D   S   K   G   S   S   Q   K   S   R   L   L
            |—————— Prolactin Signal Sequence ——————

CCTGCTGCTGGTGGTGTCAAATCTACTCTTGTGCCAGGGTGTGGTCTCCG
51   ---------+---------+---------+---------+---------+  100
     GGACGACGACCACCACAGTTTAGATGAGAACACGGTCCCACACCAGAGGC
       L   L   L   V   V   S   N   L   L   C   Q   G   V   V   S |
     ——————— Prolactin Signal Sequence ————————

Not I
     ACTACAAGGACGACGACGACGTGGACGCGGCCGCTCTTGCTGCCCCCTTT
101  ---------+---------+---------+---------+---------+  150
     TGATGTTCCTGCTGCTGCTGCACCTGCGCCGGCGAGAACGACGGGGGAAA
       D   Y   K   D   D   D   D | V   D | A   A   A   L   A   A   P   F
     ————— FLAG —————           ———————————— EK1 Pro —————

Xba I
     GATGATGATGACAAGATCGTTGGGGGCTACAACTGTCTAGAGCCGCACTC
151  ---------+---------+---------+---------+---------+  200
     CTACTACTACTGTTCTAGCAACCCCCGATGTTGACAGATCTCGGCGTGAG
       D   D   D   D   K   I   V   G   G   Y   N   C   L | E | P   H   S
     ——————————— EK1 Pro ——————————

GCAGCCCTGGCAGGCGGCACTGGTCATGGAAAACGAATTGTTCTGCTCGG
201  ---------+---------+---------+---------+---------+  250
     CGTCGGGACCGTCCGCCGTGACCAGTACCTTTTGCTTAACAAGACGAGCC
       Q   P   W   Q   A   A   L   V   M   E   N   E   L   F   C   S
     ————————————— MH2.CDS —————————————

GCGTCCTGGTGCATCCGCAGTGGGTGCTGTCAGCCGCACACTGTTTCCAG
251  ---------+---------+---------+---------+---------+  300
     CGCAGGACCACGTAGGCGTCACCCACGACAGTCGGCGTGTGACAAAGGTC
       G   V   L   V   H   P   Q   W   V   L   S   A   A   H   C   F   Q
     ————————————— MH2.CDS —————————————

AACTCCTACACCATCGGGCTGGGCCTGCACAGTCTTGAGGCCGACCAAGA
301  ---------+---------+---------+---------+---------+  350
     TTGAGGATGTGGTAGCCCGACCCGGACGTGTCAGAACTCCGGCTGGTTCT
       N   S   Y   T   I   G   L   G   L   H   S   L   E   A   D   Q   E
     ————————————— MH2.CDS —————————————
```

FIG. 14(B)

```
       GCCAGGGAGCCAGATGGTGGAGGCCAGCCTCTCCGTACGGCACCCAGAGT
351    --------+---------+---------+---------+---------+    400
       CGGTCCCTCGGTCTACCACCTCCGGTCGGAGAGGCATGCCGTGGGTCTCA
         P  G  S  Q  M  V  E  A  S  L  S  V  R  H  P  E
       ───────────────────── MH2.CDS ─────────────────────

ACAACAGACCCTTGCTCGCTAACGACCTCATGCTCATCAAGTTGGACGAA
401    --------+---------+---------+---------+---------+    450
       TGTTGTCTGGGAACGAGCGATTGCTGGAGTACGAGTAGTTCAACCTGCTT
        Y  N  R  P  L  L  A  N  D  L  M  L  I  K  L  D  E
       ───────────────────── MH2.CDS ─────────────────────

TCCGTGTCCGAGTCTGACACCATCCGGAGCATCAGCATTGCTTCGCAGTG
451    --------+---------+---------+---------+---------+    500
       AGGCACAGGCTCAGACTGTGGTAGGCCTCGTAGTCGTAACGAAGCGTCAC
         S  V  S  E  S  D  T  I  R  S  I  S  I  A  S  Q  C
       ───────────────────── MH2.CDS ─────────────────────

CCCTACCGCGGGGAACTCTTGCCTCGTTTCTGGCTGGGGTCTGCTGGCGA
501    --------+---------+---------+---------+---------+    550
       GGGATGGCGCCCCTTGAGAACGGAGCAAAGACCGACCCCAGACGACCGCT
         P  T  A  G  N  S  C  L  V  S  G  W  G  L  L  A
       ───────────────────── MH2.CDS ─────────────────────

ACGGCAGAATGCCTACCGTGCTGCAGTGCGTGAACGTGTCGGTGGTGTCT
551    --------+---------+---------+---------+---------+    600
       TGCCGTCTTACGGATGGCACGACGTCACGCACTTGCACAGCCACCACAGA
         N  G  R  M  P  T  V  L  Q  C  V  N  V  S  V  V  S
       ───────────────────── MH2.CDS ─────────────────────

GAGGAGGTCTGCAGTAAGCTCTATGACCCGCTGTACCACCCCAGCATGTT
601    --------+---------+---------+---------+---------+    650
       CTCCTCCAGACGTCATTCGAGATACTGGGCGACATGGTGGGGTCGTACAA
         E  E  V  C  S  K  L  Y  D  P  L  Y  H  P  S  M  F
       ───────────────────── MH2.CDS ─────────────────────

CTGCGCCGGCGGAGGGCACGACCAGAAGGACTCCTGCAACGGTGACTCTG
651    --------+---------+---------+---------+---------+    700
       GACGCGGCCGCCTCCCGTGCTGGTCTTCCTGAGGACGTTGCCACTGAGAC
         C  A  G  G  G  H  D  Q  K  D  S  C  N  G  D  S
       ───────────────────── MH2.CDS ─────────────────────
```

FIG. 14(C)

```
      GGGGGCCCCTGATCTGCAACGGGTACTTGCAGGGCCTTGTGTCTTTCGGA
701   --------+---------+---------+---------+---------+   750
      CCCCCGGGGACTAGACGTTGCCCATGAACGTCCCGGAACACAGAAAGCCT
       G  G  P  L  I  C  N  G  Y  L  Q  G  L  V  S  F  G
      ─────────────────── MH2.CDS ───────────────────
```

```
      AAAGCCCCGTGTGGCCAAGTTGGCGTGCCAGGTGTCTACACCAACCTCTG
751   --------+---------+---------+---------+---------+   800
      TTTCGGGGCACACCGGTTCAACCGCACGGTCCACAGATGTGGTTGGAGAC
       K  A  P  C  G  Q  V  G  V  P  G  V  Y  T  N  L  C
      ─────────────────── MH2.CDS ───────────────────
```

```
                                              Xba I
      CAAATTCACTGAGTGGATAGAGAAAACCGTCCAGGCCAGTTCTAGACATC
801   --------+---------+---------+---------+---------+   850
      GTTTAAGTGACTCACCTATCTCTTTTGGCAGGTCCGGTCAAGATCTGTAG
       K  F  T  E  W  I  E  K  T  V  Q  A  S │ S  R │ H
      ─────────────────── MH2.CDS ───────────────────
```

```
              Not I
      ACCATCACCATCACTAGCGGCCGCTTCCCTTTAGTGAGGGTTAATGCTTC
851   --------+---------+---------+---------+---------+   900
      TGGTAGTGGTAGTGATCGCCGGCGAAGGGAAATCACTCCCAATTACGAAG
       H  H  H  H  H  *│
      ── 6 X HIS-TAG ──┘                ━━━━━━━━━━━━━━
```

```
      GAGCAGACATGATAAGATACATTGATGAGTTTGGACAAACCACAACTAGA
901   --------+---------+---------+---------+---------+   950
      CTCGTCTGTACTATTCTATGTAACTACTCAAACCTGTTTGGTGTTGATCT
      ━━━━━━━━━━━━━━━━━━━━━━━━━━━━━━━━━━━━━━━━━━━━━━━━
                          SV40 Late pA
```

```
      ATGCAGTGAAAAAAATGCTTTATTTGTGAAATTTGTGATGCTATTGCTTT
951   --------+---------+---------+---------+---------+  1000
      TACGTCACTTTTTTTACGAAATAAACACTTTAAACACTACGATAACGAAA
      ━━━━━━━━━━━━━━━━━━━━━━━━━━━━━━━━━━━━━━━━━━━━━━━━
                          SV40 Late pA
```

```
      ATTTGTAACCATTATAAGCTGCAATAAACAAGTTGAC
1001  --------+---------+---------+-------              1037
      TAAACATTGGTAATATTCGACGTTATTTGTTCAACTG
      ━━━━━━━━━━━━━━━━━━━━━━━━━━━━━━━━━━━━━
```

ZYMOGEN ACTIVATION SYSTEM

RELATED APPLICATION

This application is a continuation-in-part application of application Ser. No. 09/303,162 filed Apr. 30, 1999.

BACKGROUND OF THE INVENTION

Members of the trypsin/chymotrypsin-like (S1) serine protease family play pivotal roles in a multitude of diverse physiological processes, including digestive processes and regulatory amplification cascades through the proteolytic activation of inactive zymogen precursors. In many instances protease substrates within these cascades are themselves the inactive form, or zymogen, of a "downstream" serine protease. Well-known examples of serine protease-mediated regulation include blood coagulation, (Davie, et al (1991). *Biochemistry* 30:10363–70), kinin formation (Proud and Kaplan (1988). *Ann Rev Immunol* 6:49–83) and the complement system (Reid and Porter (1981). *Ann Rev Biochemistry* 50:433–464). Although these proteolytic pathways have been known for sometime, it is likely that the discovery of novel serine protease genes and their products will enhance our understanding of regulation within these existing cascades, and lead to the elucidation of entirely novel protease networks.

The S1 family of serine proteases is the largest family of peptidases (Rawlings and Barrett (1994). *Methods Enzymol* 244:19–61). As described above, members of this diverse family perform diverse functions including food digestion, blood coagulation and fibrinolysis, complement activation as well as other immune or inflammatory responses. It is likely that these functions in both normal physiology and during diseased states, currently under investigation by numerous laboratories, will become better understood in the near future. The discovery of novel S1 serine protease cDNAs will enhance our understanding of the complex pathways controlled by these enzymes. These functions will undoubtedly be aided by the ability to express large amounts of the active protease, which is then amenable to biochemical analyses.

In the vast majority of cases, maturation of an S1 serine protease zymogen into an active form by proteolytic cleavage, results in transformation into a protease of enhanced catalytic efficiency. Zymogenicity (Tachias and Madison (1996). *J Biol Chem* 271:28749–28752), the degree of enhanced catalytic efficiency, varies widely among individual members of the serine protease family. Proteolytic cleavage of the conserved amino terminus zymogen activation sequence results in an aliphatic amino acid, most frequently isoleucine (Ile-16 chymotrypsin numbering), becoming protonated and thus, positively charged. The event that accompanies zymogen activation is the creation of a rigid substrate specificity pocket generated by a salt bridge between the aliphatic amino acid and a highly conserved residue aspartic acid (Asp-194 chymotrypsin numbering) one amino acid upstream from the active-site serine (Ser-195 chymotrypsin numbering) within the catalytic domain (Huber and Bode (1978). *Acc Chem Res* 11:114–22).

Proteases are used in non-natural environments for various commercial purposes including laundry detergents, food processing, fabric processing and skin care products. In laundry detergents, the protease is employed to break down organic, poorly soluble compounds to more soluble forms that can be more easily dissolved in detergent and water. In this capacity the protease acts as a "stain remover." Examples of food processing include tenderizing meats and producing cheese. Proteases are used in fabric processing, for example, to treat wool in order prevent fabric shrinkage. Proteases may be included in skin care products to remove scales on the skin surface that build up due to an imbalance in the rate of desquamation. Common proteases used in some of these applications are derived from prokaryotic or eukaryotic cells that are easily grown for industrial manufacture of their enzymes, for example a common species used is Bacillus as described in U.S. Pat. No. 5,217,878. Alternatively, U.S. Pat. No. 5,278,062 describes serine proteases isolated from a fungus, *Tritirachium album*, for use in laundry detergent compositions. Unfortunately use of some proteases is limited by their potential to cause allergic reactions in sensitive individuals or by reduced efficiency when used in a non-natural environment. It is anticipated that protease proteins derived from non-human sources would be more likely to induce an immune response in a sensitive individual. Because of these limitations, there is a need for alternative proteases that are less immunogenic to sensitive individuals and/or provides efficient proteolytic activity in a non-natural environment. The advent of recombinant technology allows expression of any species' proteins in a host suitable for industrial manufacture.

A major drawback in the expression of full-length serine protease cDNAs has been overwhelming potential for the production of inactive zymogen. These zymogen precursors often have little or no proteolytic activity and thus must be activated by either one of two methods currently available. One method relies on autoactivation (Little, et al. (1997). *J Biol Chem* 272:25135–25142), which may occur in homogeneous purified protease preparations, that often requires high protein concentrations, and must be rigorously evaluated on a protease specific basis. The second method uses a surrogate protease, such as trypsin, to cleave the desired serine protease. The surrogate protease must then be either inactivated (Takayama, et al. (1997). *J Biol Chem* 272:21582–21588) or physically removed from the desired activated protease. (Hansson, et al. (1994). *J Biol Chem* 269:19420–6). In both methods, the exact conditions must be established empirically and activating reactions monitored carefully, since inadequate activation or over-digestion would result in a heterogeneous population of active and inactive zymogen protein. Some investigators studying particular members of the S1 serine protease family have exploited the use of restriction proteinases on the activation of zymogens expressed in either bacterium (Wang, et al. (1995). *Biol Chem* 376:681–4) or mammalian cells (Yamashiro, et al. (1997). *Biochim Biophys Acta* 1350:11–14). In one report, the authors successfully engineered the secretion of proteolytically processed and activated murine granzyme B by taking advantage of the endogenous yeast KEX2 signal peptidase in a *Pichia pastoris* expression system (Phain et al. (1998). *J. Biol. Chem.* 273:1629–1633). U.S. Pat. No. 5,326,700 shows modification of the tissue plasminogen activator (t-PA) molecule such that the polypeptide is cleaved by the expression host cell to yield mature protein upon secretion from the cell. This example of a specific modification, while simple, suffers from the requirement that the associated protease is expressed within the host cell at such levels as to cleave the t-PA, which would be expressed in large quantities relative to other host proteins. Similarly, U.S. Pat. Nos. 5,270,178 and 5,196,322 describe modification of the protein C cleavage site such that it becomes a more efficient substrate of the protease thrombin. These examples of activating recombinant zymogens clearly have the added value to permit expression and activation of several serine proteases, however there remains unmet needs in the field. The example of Pham et al clearly limits the expression system available for use due to the nature of the signal peptide. The other examples describe enzyme specific engineered constructs that do not easily predict a generic method to which other serine proteases may be applied.

Introduction of proteolytic cleavage sites into fusion proteins is well known in the art. However, it is the present invention, for the first time, that creates a fusion protein designed for the generic activation of S1 serine proteases by the introduction of a propeptide region with a predefined, easily processed, cleavage site. Inclusion of the catalytic domain of a serine protease into the fusion gene allows the specific enzyme's activity to be preserved without the requirement of a specific activating enzyme. Because the protein is proteolytically processed using commercially available enzymes after expression in the host cell, the fusion proteins of the present invention can be expressed in any suitable cell line, including prokaryotic, eukaryotic, yeast, and insect cell lines well known in the art.

The unmet need of a genetic method to express enzymatically active serine protease is described by the current invention that provides a nucleic acid cloning method to extract the catalytic domain from any serine protease. The extracted catalytic domain may then be manipulated to simplify purification, and then expressed in any suitable cell type including bacteria, yeasts, and eukaryotic cells. Herein we describe enzymatically active, human serine proteases herein termed, prostasin (Yu et al. (1995). *J. Biol. Chem.* 270:13483–9), O (Yoshida, S. et al. (1998). Biochim. Biophys. Acta 1399, 225–228), neuropsin (Yoshida, S. et al. (1998). *Gene* 213, 9–16), F (Inoue, M., et al (1998). Biochem. Biophys. Res. Commun. 252, 307–312.) and MH2 (Nelson et al. (1999). *Proc. Natl. Acad. Sci. U. S. A.* 96:3114–3119). Isolation of any one or more of these purified, enzymatically active proteases allows the protein to be used directly, for the treatment of certain diseases or as an additive in commercial products. For example, isolation of purified, enzymatically active protease O allows the protein to be used directly, for the treatment of certain skin diseases or to enhance skin pigmentation. Isolation of purified, enzymatically active protease F allows the protein to be used directly, for example, for the treatment of inflammatory disease or in reproductive development, since it is expressed in eosinophils and testis (Inoue et al. (1998). *Biochem. Biophys. Res. Commun.* 252:307–312) or as an additive in commercial products. Since protease MH2 is prostate specific (Nelson et al. (1999). *Proc. Natl. Acad. Sci. U. S. A.* 96:3114–3119), it may be used as a marker for certain grades of prostate cancer. Thus, the identification of sensitive protease MH2 substrates, which would be facilitated with an active protease MH2 preparation, may result in a more reliable diagnostic marker for prostate cancer medical evaluation. Isolation of any one of these purified, enzymatically active proteases will allow them to be used directly as therapeutic proteins, for example, for the treatment of neurological function, particularly in memory functions, as well as in dermatological diseases or pancreatic insufficiency. In addition, they may be used as an additive in commercial products. Because these proteases are derived from a human host, they are less likely to induce an allergic reaction in sensitive individuals, and therefore proteases prostasin, O, neuropsin, F and MH2 could also be useful for formulation of compositions for laundry detergents and skin care products. Alternatively, enzymatically active proteases prostasin, MH2, F, O, and neuropsin may be used to discover chemical modulators of the enzyme that may be useful for treatment of the aforementioned physiological and pathological states.

SUMMARY OF THE INVENTION

The present invention provides a series of DNA vectors allowing for the systematic expression of heterologous inactive zymogen proteases that can subsequently be proteolytically processed to generate the active enzyme product. The present invention provides a system that allows generic expression and activation of S1 protease family members in bacteria, yeasts, or eukaryotic cells.

The protein products of serine protease cDNAs generated within this particular zymogen activation system can be proteolytically activated, whereby the recombinant protein will become activated to an extent similar to its mature activated gene product counterpart from native or endogenous sources.

Enzymatically active proteases MH2, F, prostasin, O, and neuropsin or any other protease are amenable to further biochemical analyses for the identification of physiological substrates and specific modulators. Modulators identified in the chromogenic assay disclosed herein are potentially useful as therapeutic agents in the treatment of diseases associated with, but not limited to, inflammatory, reproductive, epidermal and neurological tissues. Isolation of purified, enzymatically active proteases MH2, F, prostasin, O, and neuropsin or any other protease allows the proteins to be used directly, for example, for the treatment of diseases associated with, but not limited to, inflammatory, reproductive, epidermal and neurological tissues. Purified proteases MH2, F, prostasin, O, and neuropsin or any other protease can be manufactured as a component for use in commercial products including laundry detergents, stain-removing solutions, and skin care products.

BRIEF DESCRIPTION OF THE DRAWINGS

FIG. 2—The sequences of various activation constructs (SEQ.ID.NO.:1 through SEQ.ID.NO.:6) are presented. For each, the double-stranded nucleotide sequence is shown, below which segments are translated to reveal the pertinent amino acid sequence encoded by each respective module. The relevant restriction endonuclease sites are also included along with the sequences derived from the SV 40 Late polyadenylation sequences.

SEQ.ID.NO.:1 Construct:PFEK2-Stop
SEQ.ID.NO.:2 Construct:TEK3-1XHA-TAG
SEQ.ID.NO.:3 Construct:PFFXa-3XHA-TAG
SEQ.ID.NO.:4 Construct:PFEK1-6HIS-TAG
SEQ.ID.NO.:5 Construct:CFEK2-6XHIS-TAG
SEQ.ID.NO.:6 Construct:CFEK2-HA6XHIS-TAG FIG. 3—The sequence of the catalytic domain from the protease prostasin, inserted into the PFEK2-6XHIS-TAG activation construct (SEQ.ID.NO.:7).

FIG. 4—The sequence of the catalytic domain from the protease prostasin, inserted into the CFEK2-6XHIS-TAG activation construct (SEQ.ID.NO.:8).

FIG. 5—The sequence of the catalytic domain from the protease neuropsin, inserted into the PFEK1-6XHIS-TAG activation construct (SEQ.ID.NO.:9).

FIG. 6—The sequence of the catalytic domain from the protease O, inserted into the PFEK1-6XHIS-TAG activation construct (SEQ.ID.NO.:10).

Figure 7:
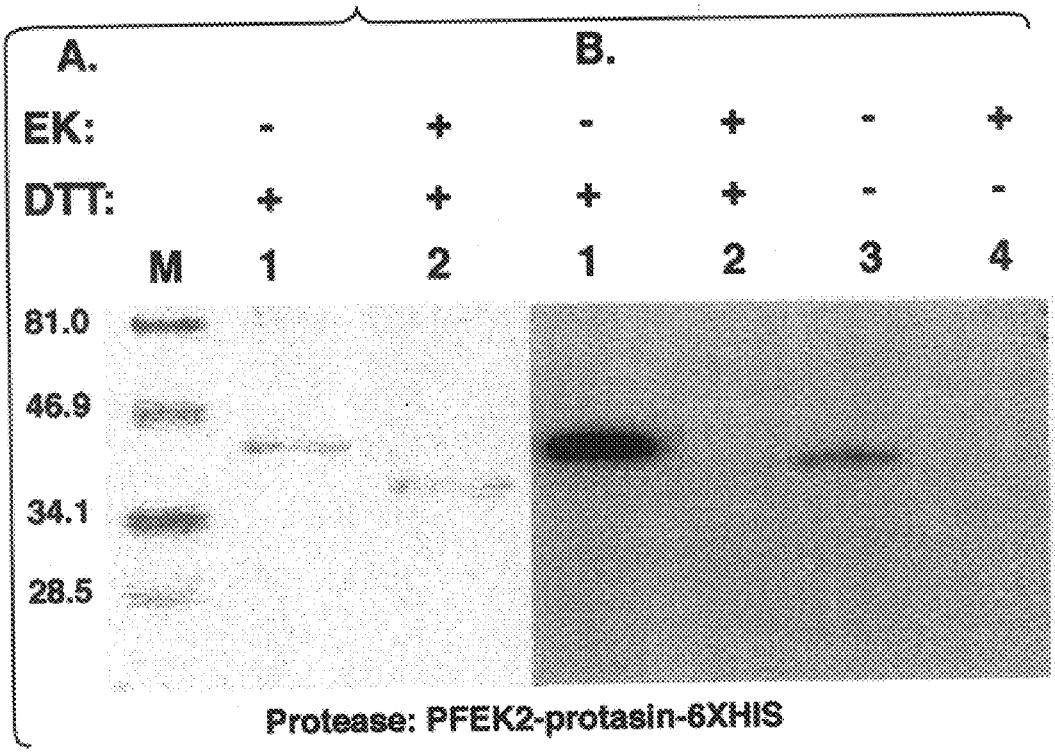

FIG. 7—Polyacrylamide gel and Western blot analyses of the recombinant protease PFEK2-prostasin-6XHIS expressed, purified and activated from the activation construct of SEQ.ID.NO.:7 (FIG. 3). Shown is the polyacrylamide gel containing samples of the serine protease PFEK2-prostasin-6XHIS stained with Coomassie Brilliant Blue (A). The relative molecular masses are indicated by the positions of protein standards (M). In the indicated lanes, the purified zymogen was either untreated (−) or digested with EK (+) which was used to cleave and activate the zymogen into its active form. A Western blot of the gel in A, probed with the anti-FLAG MoAb M2, is also shown (B lanes 1 and 2). This demonstrates the quantitative cleavage of the expressed and purified zymogen to generate the processed and activated protease. Since the FLAG epitope is located just upstream of the of the EK pro sequence, cleavage with EK generates a FLAG-containing polypeptide which is too small to be retained in the polyacrylamide gel, and is therefore not detected in the +EK lanes. Also shown in panel B, the untreated or EK digested PFEK2-prostasin-6XHIS was denatured in the absence of DTT, in order to retain disulfide bonds, prior to electrophoresis (lanes 3 and 4). Although equivalent amounts of sample were loaded into each lane of the gel in the Western blot of B, the anti-FLAG MoAb M2 appears to detect proteins better when pretreated with DTT (compare lane B1 with B3).

Figure 8:
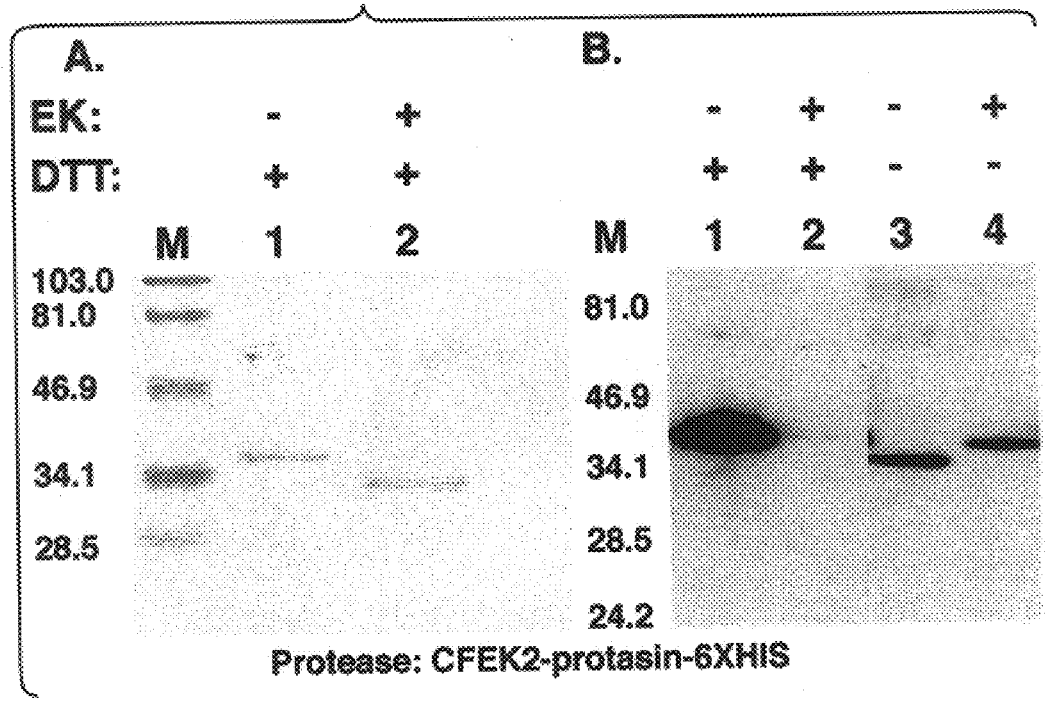

FIG. 8—Polyacrylamide gel and Western blot analyses of the recombinant protease CFEK2-prostasin-6XHIS expressed, purified and activated from the activation construct of SEQ.ID.NO.:8 (FIG. 4). Shown is the polyacrylamide gel containing samples of the serine protease CFEK2-prostasin-6XHIS stained with Coomassie Brilliant Blue (A). The relative molecular masses are indicated by the positions of protein standards (M). In the indicated lanes, the purified zymogen was either untreated (−) or digested with EK (+) which was used to cleave and activate the zymogen into its active form. A Western blot of the gel in A, probed with the anti-FLAG MoAb M2, is also shown (B lanes 1 and 2). This demonstrates the quantitative cleavage of the expressed and purified zymogen to generate the processed and activated protease. Since the FLAG epitope is located just upstream of the of the EK2 pro sequence, cleavage with EK generates a FLAG-containing polypeptide which is too small to be retained in the polyacrylamide gel, and is therefore not detected in the +EK lanes. Also shown in panel B, the untreated or EK digested CFEK2-prostasin-6XHIS was denatured in the absence of DTT, in order to retain disulfide bonds, prior to electrophoresis (lanes 3 and 4). Of significance in lane 4 is the retention of the FLAG epitope indicating the formation of a disulfide bond between the cysteine in the CF pre sequence with a cysteine in the catalytic domain of prostasin which is presumably Cys-122 (chymotrypsin numbering). Retention of the FLAG epitope, following EK cleavage and denaturation without DTT, is not observed using the prolactin pre sequence which lacks a cysteine residue (Compare lane 4 of FIG. 7 with lane 4 of FIG. 8). This documents that the CF pre sequence is capable of forming a light chain, that is disulfide bonded to the heavy catalytic chain of the recombinant serine proteases, when expressed in this system. It appears that in the absence of the reducing agent DTT, the EK cleaved polypeptides have a reproducibly decreased mobility in the gel (compare lane B3 with B4).

Figure 9:
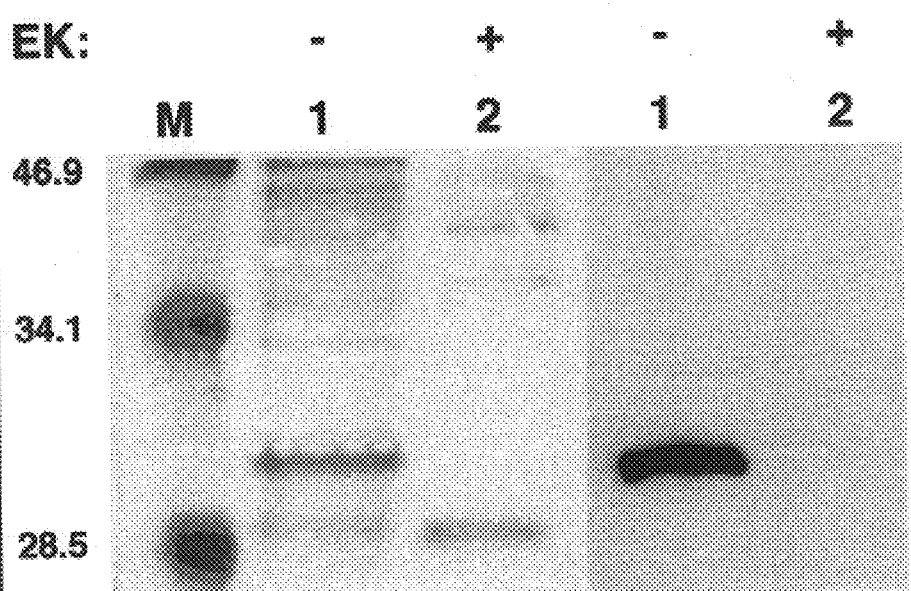

FIG. 9—Polyacrylamide gel and Western blot analyses of the recombinant protease PFEK1-neuropsin-6XHIS expressed, purified and activated from the activation construct of SEQ.ID.NO.:9 (FIG. 5). Shown is the polyacrylamide gel containing samples of the serine protease PFEK1-neuropsin-6XHIS stained with Coomassie Brilliant Blue (A). The relative molecular masses are indicated by the positions of protein standards (M). In the indicated lanes, the purified zymogen was either untreated (−) or digested with EK (+) which was used to cleave and activate the zymogen into its active form. A Western blot of the gel in A, probed with the anti-FLAG MoAb M2, is also shown. This demonstrates the quantitative cleavage of the expressed and purified zymogen to generate the processed and activated protease. Since the FLAG epitope is located just upstream of the of the EK1 pro sequence, cleavage with EK1 generates a FLAG-containing polypeptide which is too small to be retained in the polyacrylamide gel, and is therefore not detected in the +EK lane.

Figure 10:
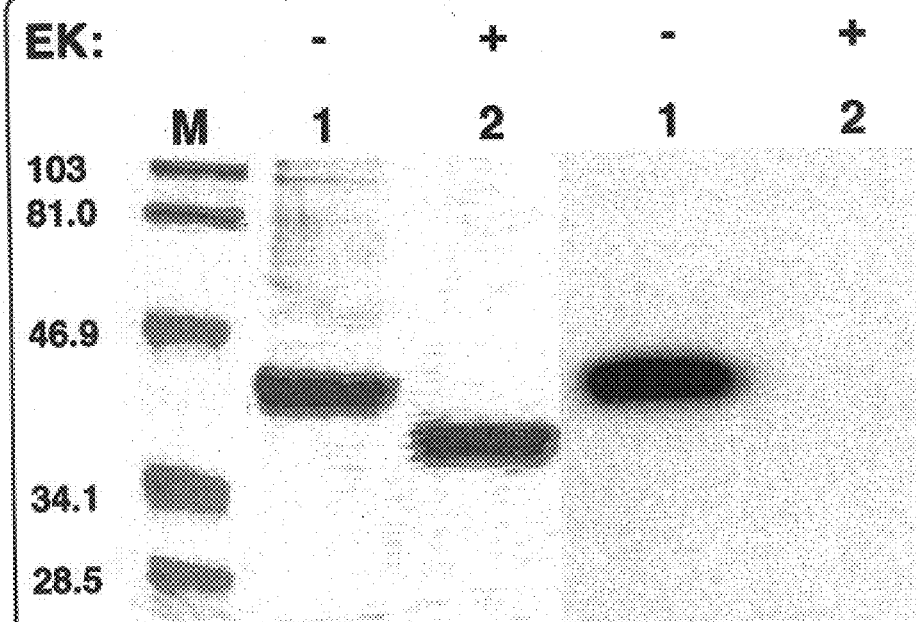

FIG. 10—Polyacrylamide gel and Western blot analyses of the recombinant protease PFEK1-protease O-6XHIS expressed, purified and activated from the activation construct of SEQ.ID.NO.:10 (FIG. 6). Shown is the polyacrylamide gel containing samples of the novel serine protease PFEK1-protease O-6XHIS stained with Coomassie Brilliant Blue (A). The relative molecular masses are indicated by the positions of protein standards (M). In the indicated lanes, the purified zymogen was either untreated (−) or digested with EK (+) which was used to cleave and activate the zymogen into its active form. A Western blot of the gel in A, probed with the anti-FLAG MoAb M2, is also shown. This demonstrates the quantitative cleavage of the expressed and purified zymogen to generate the processed and activated protease. Since the FLAG epitope is located just upstream of the of the EK pro sequence, cleavage with EK generates a FLAG-containing polypeptide which is too small to be retained in the polyacrylamide gel, and is therefore not detected in the +EK lane.

Figure 11:
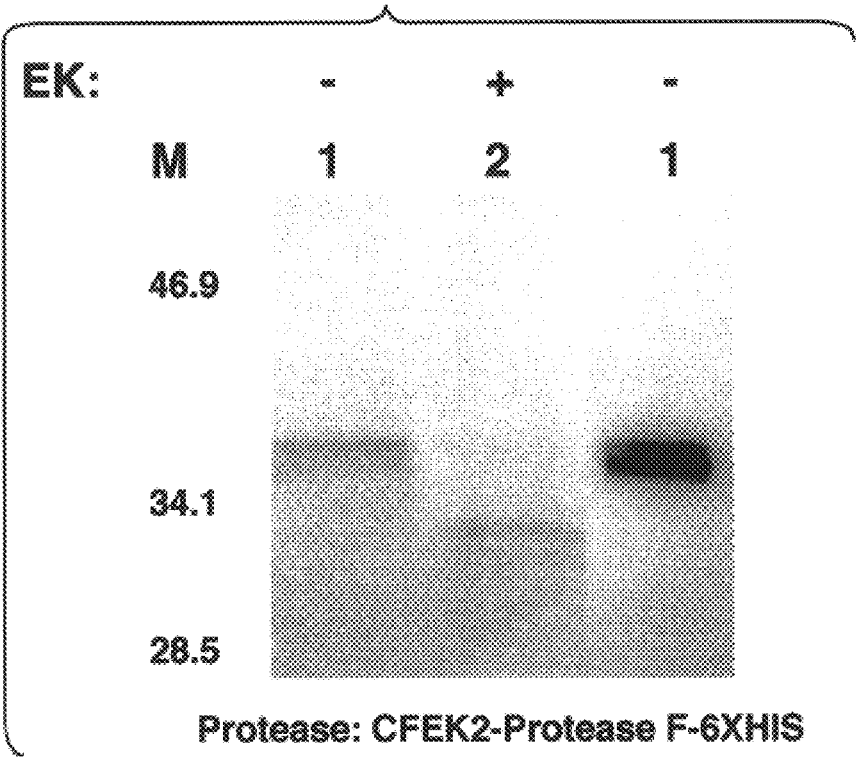

FIG. 11 Polyacrylamide gel and Western blot analyses of the recombinant protease PFEK2-protease F-6XHIS. Shown is the polyacrylamide gel containing samples of the novel serine protease PFEK2-protease F-6XHIS stained with Coomassie Brilliant Blue(Leftmost lanes 1 and 2). The relative molecular masses are indicated under the column labeled (M). In the indicated lanes, the purified zymogen was either untreated (−) or digested with EK (+) which was used to cleave and activate the zymogen into its active form. A Western blot of the gel, probed with the anti-FLAG MoAb M2, is also shown (rightmost 1). This demonstrates the quantitative cleavage of the expressed and purified zymogen to generate the processed and activated protease.

Figure 12:
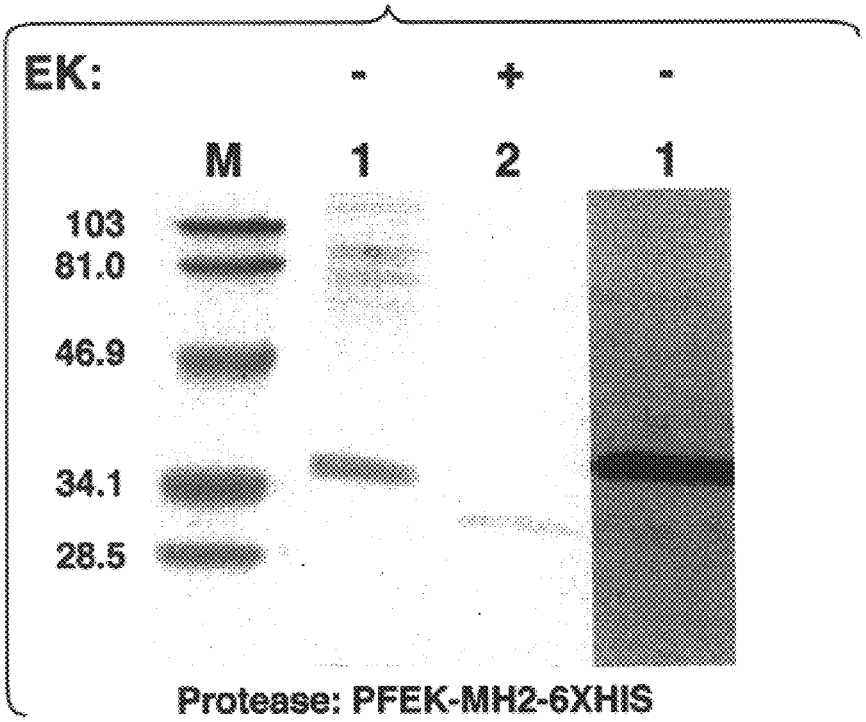

FIG. 12 Polyacrylamide gel and Western blot analyses of the recombinant protease PFEK1-protease MH2-6XHIS. Shown is the polyacrylamide gel containing samples of the novel serine protease PFEK1-protease MH2-6XHIS stained with Coomassie Brilliant Blue (Leftmost 1 and 2). The relative molecular masses are indicated by the positions of protein standards (M). In the indicated lanes, the purified zymogen was either untreated (−) or digested with EK (+) which was used to cleave and activate the zymogen into its active form. A Western blot of the gel in A, probed with the anti-FLAG MoAb M2, is also shown (rightmost 1). This demonstrates the quantitative cleavage of the expressed and purified zymogen to generate the processed and activated protease.

Figure 13D:
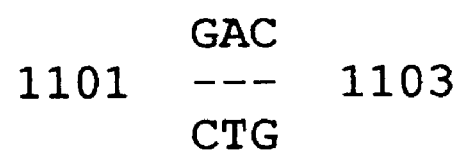

FIG. 13—The sequence of the catalytic domain from the protease F, inserted into the PFEK2-6XIS-TAG activation construct (SEQ.ID.NO.:53).

FIG. 14—The sequence of the catalytic domain from the protease MH2, inserted into the PFEK1-6XHIS-TAG activation construct (SEQ.ID.NO.:54).

DETAILED DESCRIPTION OF THE INVENTION

DEFINITIONS

The term "protein domain" as used herein refers to a region of a protein that can fold into a stable three-dimensional structure independent to the rest of the protein. This structure may maintain a specific function associated with the domain's function within the protein including enzymatic activity, creation of a recognition motif for another molecule, or provide necessary structural components for a protein to exist in a particular environment. Protein domains are usually evolutionarily conserved regions of proteins, both within a protein superfamily and within other protein superfamilies that perform similar functions.

The term "protein superfamily" as used herein refers to proteins whose evolutionary relationship may not be entirely established or may be distant by accepted phylogenetic standards, but show similar three dimensional structure or display unique consensus of critical amino acids. The term "protein family" as used herein refers to proteins whose evolutionary relationship has been established by accepted phylogenic standards.

The term "fusion protein" as used herein refers to protein constructs that are the result of combining multiple protein domains or linker regions for the purpose of gaining function of the combined functions of the domains or linker regions. This is most often accomplished by molecular cloning of the nucleotide sequences to result in the creation of a new polynucleotide sequence that codes for the desired protein. Alternatively, creation of a fusion protein may be accomplished by chemically joining two proteins together.

The term "liner region" or "linker domain" or similar such descriptive terms as used herein refers to stretches of polynucleotide or polypeptide sequence that are used in the construction of a cloning vector or fusion protein. Functions of a linker region can include introduction of cloning sites into the nucleotide sequence, introduction of a flexible component or space-creating region between two protein domains, or creation of an affinity tag for specific molecule interaction. A linker region may be introduced into a fusion protein without a specific purpose, but results from choices made during cloning.

The term "pre-sequence" as used herein refers to a nucleotide sequence that encodes a secretion signal amino acid sequence. A wide variety of such secretion signal sequences are known to those skilled in the art, and are suitable for use in the present invention. Examples of suitable pre-sequences include, but are not limited to, prolactinFLAG, trypsinogen, and chymoFLAG.

The term "pro-sequence" as used herein refers to a nucleotide sequence that encodes a cleavage site for a restriction protease. A wide variety of cleavage sites for restriction proteases are known to those skilled in the art, and are suitable for use in the present invention. Examples of suitable pro-sequences include, but are not limited to, EK, FXa, and thrombin.

The term "cloning site" or "polycloning site" as used herein refers to a region of the nucleotide sequence contained within a cloning vector or engineered within a fusion protein that has one or more available restriction endonuclease consensus sequences. The use of a correctly chosen restriction endonuclease results in the ability to isolate a desired nucleotide sequence that codes for an in-frame sequence relative to a start codon that yields a desirable protein product after transcription and translation. These nucleotide sequences can then be introduced into other cloning vectors, used create novel fusion proteins, or used to introduce specific site-directed mutations. It is well known by those in the art that cloning sites can be engineered at a desired location by silent mutations, conserved mutation, or introduction of a linker region that contains desired restriction enzyme consensus sequences. It is also well known by those in the art that the precise location of a cloning site can be flexible so long as the desired function of the protein or fragment thereof being cloned is maintained.

The term "tag" as used herein refers to a nucleotide sequence that encodes an amino acid sequence that facilitates isolation, purification or detection of a fusion protein containing the tag. A wide variety of such tags are known to those skilled in the art, and are suitable for use in the present invention. Suitable tags include, but are not limited to, HA-tag, His-tag, biotin, avidin, and antibody binding sites.

As used herein, "expression vectors" are defined herein as DNA sequences that are required for the transcription of cloned copies of genes and the translation of their mRNAs in an appropriate host. Such vectors can be used to express eukaryotic genes in a variety of hosts such as bacteria including *E. coli*, blue-green algae, plant cells, insect cells, fungal cells including yeast cells, and animal cells.

The term "catalytic domain cassette" as used herein refers to a nucleotide sequence that encodes an amino acid sequence encoding at least the catalytic domain of the serine protease of interest. A wide variety of protease catalytic domains may be inserted into the expression vectors of the present invention, including those presently known to those skilled in the art, as well as those not yet having an isolated nucleotide sequence encodes it, once the nucleotide sequence is isolated.

As used herein, a "functional derivative" of the nucleotide sequence, vector, or polypeptide possesses a biological activity (either functional or structural) that is substantially similar to the properties described herein. The term "functional derivatives" is intended to include the "fragments," "variants," "degenerate variants," "analogs" and "homologues" of the nucleotide sequence, vector, or polypeptide. The term "fragment" is meant to refer to any nucleotide sequence, vector, or polypeptide subset of the modules described as pre and pro sequences used for the activation of expressed zymogen precursors. The term "variant" is meant to refer to a nucleotide or amino acid sequence that is substantially similar in structure and function to either the entire nucleic acid sequence or encoded protein or to a fragment thereof. A nucleic acid or amino acid sequence is "substantially similar" to another if both molecules have similar structural characteristics or if both molecules possess similar biological properties. Therefore, if the two molecules possess substantially similar activity, they are considered to be variants even if the structure of one of the molecules is not found in the other or even if the two amino acid sequences are not identical. The term "analog" refers to a protein molecule that is substantially similar in function to another related protein.

Figure 1:
FIG. 1—Shown schematically is this zymogen activation vector that features a series of interchangeable modules represented by segments of different pattern and summarized in the Table. The arrowhead over the pro sequence indicates that sequences within this region can be cleaved with a restriction protease. The HDS represent the amino acids of the catalytic triad in the serine protease catalytic domain cassette. Listed below are the various sequence modules we have employed for the secretory pre sequences, the zymogen activation pro sequences and various C-terminal affinity/epitope tagging combinations we have designed and successfully used. These constructs can be generally used to express different serine proteases by the in-frame insertion of a particular cDNA fragment encoding only the conserved catalytic domain. The generic activation is achieved through the digestion of the purified zymogen using the appropriate restriction protease EK or FXa.

The present invention relates to DNA encoding an expression vector system, schematized in FIG. 1, which will permit post-translational modification, through limited proteolysis, to activate inactive zymogen precursor proteins in a highly controlled and reproducible fashion. The expressed and processed protein is rendered in an activated form amenable to measuring its catalytic activity which often gives a more accurate representation of the mature protease gene product than is often available from purified native tissue samples.

The present invention includes the enzymatically active human serine protease, termed prostasin by means of comparison. Since the enzymatic activity of native purified prostasin (Yu et al. (1994). *J. Biol. Chem.* 269:18843–8) along with its nucleotide sequence have previously been reported (Yu et al. (1995). *J. Biol. Chem.* 270:13483–9), we wanted to compare the recombinant prostasin expressed and activated from the zymogen activation construct to the native prostasin purified from seminal fluid. Thus, when the substrate specificity of the recombinant prostasin expressed and activated from the zymogen activation construct is compared to that previously published for the native prostasin (Yu et al. (1994). *J. Biol. Chem.* 269:18843–8), there is agreement between the substrate preferences. In both cases, the prostasin cleaves a variety of substrates containing the amino acid arginine the P1 position, which is just upstream of the scissile bond. The present invention also includes a wide variety of enzymatically active human serine proteases, including but not limited to protease O, neuropsin, F and MH2. The cloning of full-length DNA molecules encoding human proteins of identical sequence to protease O (Yoshida et al. (1998). *Biochim. Biophys. Acta* 1399:225–228), neuropsin (Yoshida et al. (1998). *Gene* 213:9–16), protease F (Inoue et al. (1998). *Biochem. Biophys. Res. Commun.* 252:307–312;) and protease MH2 (Nelson et al. (1999). *Proc. Natl. Acad. Sci. U. S. A.* 96:3114–3119) were recently reported, as well as some analysis of their nucleic acid expression in human tissues. These references do not, however, demonstrate functional expression of the proteins, nor do they describe characterization of the enzymatic activity of, these novel human serine proteases. This is the first report of functionally active proteases O, neuropsin, F, prostasin, and MH2 as well as the first description of a method to express large amounts of the protein for further biochemical analysis and further manufacture of commercially valuable products. It shall be readily apparent to those skilled in the art that a wide variety of proteases other than proteases O, neuropsin, F, prostasin, and MH2 are suitable for use in the present invention, and that other proteases can readily be substituted for proteases O, neuropsin, F, prostasin, and MH2 in this disclosure. The proteases O, neuropsin, F, prostasin, and MH2 are recited herein as examples of suitable proteases for use in the present invention, without limiting in any way the application of other proteases in this invention.

Any of a variety of procedures, known in the art, may be used to molecularly manipulate recombinant DNA to enable study of a particular serine protease using this system. These methods include, but are not limited to, direct functional expression of the serine protease cDNA following their insertion into and subsequent expression from this series of vectors. A method to obtain such a serine protease cDNA molecule is to screen a cDNA library constructed in a bacteriophage or plasmid shuttle vector with a labeled oligonucleotide probe designed from the amino acid sequence or restriction fragment of the partial or related cDNA. This partial cDNA is obtained by the specific polymerase chain reaction (PCR) amplification of the cDNA fragments through the design of matching or degenerate oligonucleotide primers from the sequence of the cDNA or amino acid sequence of the protein. Expressed sequence tags (ESTs) are also available for this purpose. Alternatively, the full-length cDNA of a published sequence may be obtained by the specific PCR amplification through the design of matching oligonucleotide primers flanking the entire coding sequence. Insertion into the zymogen activation construct described herein would require only the isolation, through PCR amplification, of just the catalytic domain (catalytic cassette) of the particular serine protease cDNA. The catalytic domain can then be subcloned into the zymogen activation construct in the proper translational register and orientation so as to produce a recombinant fusion protein.

The serine protease catalytic cassette obtained through the methods described above may be recombinantly expressed by molecular cloning into an expression vector containing a suitable promoter and other appropriate transcription regulatory elements, and transferred into prokaryotic or eukaryotic host cells to express a recombinant zymogen of the serine protease catalytic domain. Techniques for such manipulations are fully described in (Sambrook, et al. *Molecular Cloning: A Laboratory Manual*, 2nd ed., (1989). 1–1626) and are well known to those in the art.

Specifically designed vectors allow the shuttling of DNA between hosts such as bacteria-yeast or bacteria-animal cells or bacteria-fungal cells or bacteria-invertebrate cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one that causes mRNAs to be initiated at high frequency. Expression vectors may include, but are not limited to, cloning vectors, modified cloning vectors, specifically designed plasmids or viruses.

A variety of mammalian expression vectors may be used to express recombinant serine protease catalytic domain in a zymogen configuration in mammalian cells. Commercially available mammalian expression vectors which may be suitable for recombinant protein expression, include but are not limited to, pCI Neo (Promega, Madison, Wis., Madison Wis.), pMAMneo (Clontech, Palo Alto, Calif.), pcDNA3 (InVitrogen, San Diego, Calif.), pMCIneo (Stratagene, La Jolla, Calif.), pXT1 (Stratagene, La Jolla, Calif.), pSG5 (Stratagene, La Jolla, Calif.), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and 1ZD35 (ATCC 37565).

A variety of bacterial expression vectors may be used to express recombinant serine protease catalytic domain in a zymogen form in bacterial cells. Commercially available bacterial expression vectors which may be suitable for recombinant protein expression include, but are not limited to pET vectors (Novagen, Inc., Madison Wis.) and pQE vectors (Qiagen, Valencia, Calif.) pGEX (Pharmacia Biotech Inc., Piscataway, N.J.). In general, as is found for many mammalian cDNAs, bacterial serine protease cDNA expression can result in insoluble recombinant proteins that must be renatured in order to refold the protein in the active conformation (Takayama, et al. (1997). *J Biol Chem* 272:21582–21588).

A variety of fungal cell expression vectors may be used to express recombinant serine protease catalytic domain in a zymogen configuration in fungal cells such as yeast. Commercially available fungal cell expression vectors which may be suitable for recombinant protein expression include but are not limited to pYES2 (InVitrogen, San Diego, Calif.) and Pichia expression vector (InVitrogen, San Diego, Calif.).

A variety of insect cell expression systems may be used to express recombinant serine protease catalytic domain in a zymogen form in insect cells. Commercially available baculovirus transfer vectors which may be suitable for the generation of a recombinant baculovirus for recombinant protein expression in Sf9 cells include but are not limited to pFastBac1 (Life Technologies, Gaithersberg, Md.) pAcSG2 (Pharmingen, San Diego, Calif.) pBlueBacII (InVitrogen, San Diego, Calif.). In addition, a class of insect cell vectors, which permit the expression of recombinant proteins in Drosophila Schneider line 2 (S2) cells, is also available (InVitrogen, San Diego, Calif.).

DNA encoding the zymogen activation construct may be subcloned into an expression vector for expression in a recombinant host cell. Recombinant host cells may be prokaryotic or eukaryotic, including but not limited to bacteria such as $E.$ $coli$, fingal cells such as yeast, mammalian cells including but not limited to cell lines of human, bovine, porcine, monkey and rodent origin, and insect cells including but not limited to Drosophila S2 (ATCC CRL-1963) and silkworm Sf9 (ATCC CRL-1711), derived cell lines. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171), L-cells, and HEK-293 (ATCC CRL1573).

The expression vector may be introduced into host cells via any one of a number of techniques including but not limited to transformation, transfection, protoplast fusion, lipofection, and electroporation. Pools of transfected cells may be cultured and analyzed for recombinant protein expression. Alternatively, the expression vector-containing cells are clonally propagated and individually analyzed to determine whether they produce recombinant protein. Identification of host cell clones expressing recombinant serine protease catalytic domain in a zymogen configuration may be done by several means, including but not limited to immunological reactivity with antibodies directed against the amino acid sequence of serine protease catalytic domain if available.

To determine the protease MH2, F, prostasin, O, and neuropsin or any other protease or any other protease DNA sequence(s) that yields optimal levels of proteolytic activity and/or MH2, F, prostasin, O, and neuropsin or any other protease or any other protease protein, DNA molecules including, but not limited to, the following can be constructed: the full-length open reading frame of the protease cDNA encoding the 30-kDa protein from approximately base 69 to approximately base 920 (these numbers correspond to first nucleotide of first methionine and last nucleotide before the first stop codon; FIG. 1) and several constructs containing portions of the cDNA encoding the MH2, F, prostasin, O, and neuropsin protease. Constructs described herein can be designed to contain only the portions of the catalytic domains of heterologous serine proteases including but not limited to protease prostasin, O, neuropsin, F and MH2 cDNAs or fusion chimerics of their catalytic domains with other serine protease catalytic domains. Protease activity and levels of protein expression can be determined following the introduction, both singly and in combination, of these constructs into appropriate host cells. Following determination of the protease MH2, F, prostasin, O, and neuropsin or any other protease or any other protease DNA cassette yielding optimal expression in transient assays, the DNA construct is transferred to a variety of expression vectors, for expression in host cells including, but not limited to, mammalian cells, baculovirus-infected insect cells, $E.$ $coli$, and the yeast $S.$ $cerevisiae.$ Host cell transfectants and microinjected oocytes may be used to assay both the levels of protease proteolytic activity and levels of MH2, F, prostasin, O, and neuropsin or any other protease or any other protease protein by the following methods. In the case of recombinant host cells, this involves the co-transfection of one or possibly two or more plasmids, containing the protease DNA encoding one or more fragments or subunits. In the case of oocytes, this involves the co-injection of synthetic RNAs encoding protease. Following an appropriate period of time to allow for expression, cellular protein is metabolically labeled with, for example $^{35}$S-methionine for 24 hours, after which cell lysates and cell culture supernatants are harvested and subjected to immunoprecipitation with polyclonal antibodies directed against the protease protein.

Other methods for detecting protease expression involve the direct measurement of MH2, F, prostasin, O, and neuropsin or any other protease or any other protease proteolytic activity in whole cells transfected with protease MH2, F, prostasin, O, and neuropsin or any other protease or any other protease cDNA or oocytes injected with protease mRNA. Proteolytic activity can be measured by analyzing conditioned media or cell lysates by hydrolysis of a chromogenic or fluorogenic substrate. In the case of recombinant host cells expressing protease MH2, F, prostasin, O, and neuropsin or any other protease or any other protease, higher levels of substrate hydrolysis would be observed relative to mock transfected cells or cells transfected with expression vector lacking the protease DNA insert. In the case of oocytes, lysates or conditioned media from those injected with RNA encoding protease MH2, F, prostasin, O, and neuropsin or any other protease, would show higher levels of substrate hydrolysis than those oocytes programmed with an irrelevant RNA.

Other methods for detecting proteolytic activity include, but are not limited to, measuring the products of proteolytic degradation of radiolabeled proteins (Coolican et al. (1986). $J.$ $Biol.$ $Chem.$ 261:4170–6), fluorometric (Lonergan et al. (1995). $J.$ $Food$ $Sci.$ 60:72–3, 78; Twining (1984). $Anal.$ $Biochem.$ 143:30–4) or colorimetric (Buroker-Kilgore and Wang (1993). $Anal.$ $Biochem.$ 208:387–92) analyses of degraded protein substrates. Zymography following SDS polyacrylamide gel electrophoresis (Wadstroem and Smyth (1973). $Sci.$ $Tools$ 20:17–21), as well as by fluorescent resonance energy transfer (FRET)-based methods (Ng and Auld (1989). $Anal.$ $Biochem.$ 183:50–6) are also methods used to detect proteolytic activity.

The zymogen activation vector described herein contains modules encoding epitope tags for anti-FLAG and/or anti-HA monoclonal antibodies, which are readily available (Babco, Richmond, Calif.). Thus, levels of the expressed zymogen protein can be quantified by immunoaffinity and/or ligand affinity techniques. These can be employed by any one of a number of means, such as Western blotting, ELISA or RIA assays of conditioned media from transfected eukaryotic cells or transformed bacterial lysates to detect the production of secreted recombinant serine protease catalytic domain in zymogen form. Since the FLAG epitope is located between the pre and pro sequences, and is removed upon proteolytic activation with either enterokinase (EK) or factor Xa (FXa), the disappearance of this tag is an effective measure of quantitative digestion (see FIGS. 7, 8, 9 and 10).

Several members of the S1 serine protease family appear to be membrane bound. They may be type II integral membrane proteases, anchored by the $NH_2$-terminus as is the case for hepsin (Leytus, et al. (1988). *Biochemistry* 27:1067–74) and EK (Kitamoto, et al. (1994). *Proc. Natl. Acad. Sci. U. S. A.* 91:7588–92), or at the C-terminus as exemplified by prostasin (Yu, et al. (1995). *J. Biol. Chem.* 270:13483–9). In these cases, the biochemical characterization of serine proteases generated in this system is facilitated in that only the catalytic portion is expressed and these trans-membrane domains are excluded. Thus, the expressed zymogens are soluble, which greatly facilitates purification, activation, and subsequent biochemical analyses. Expression of the catalytic domain by the generation of a catalytic cassette module precludes the difficulties one would encounter with the type II membrane bound serine proteases, since the trans-membrane domain is within an extended non-catalytic $NH_2$-terminus. The design of a soluble catalytic module of the C-terminally tethered serine proteases however, would require trans-membrane prediction in order to determine how to truncate the catalytic domain upstream of the predicted trans-membrane segment. Identifying putative trans-membrane spanning regions within a particular polypeptide is often accomplished by measuring amino acid hydropathy within a stretch of the sequence being analyzed. There are currently sequence analysis algorithms that are capable of determining regional hydropathy (Kyte and Doolittle (1982). *J. Mol. Biol.* 157:105–32) enabling the prediction of a potential trans-membrane anchoring C-terminal tail within a given protease sequence.

We have found that activation with either of the two restriction proteases EK and FXa occurs efficiently when the purified serine protease zymogen is bound to Ni-NTA agarose beads. The proteolytic activity of Ni-NTA agarose bead-bound recombinant protease, once cleaved and activated, is unimpeded. The Ni-NTA agarose bead-bound proteases (protease beads) appear stable and their activity can be measured by sequential chromogenic assays, punctuated by intermittent washings, and are active through multiple rounds of assay. Although the stability of the protease beads will be determined by the properties of the particular protease being analyzed, potentially these protease beads could be applied where the immobilization of the protease is required. An example might be for in vivo analysis of the proteolytic activity. A protease bead preparation could be evaluated following subcutaneous or intramuscular delivery and since the Ni-NTA agarose bead-bound protease would be unlikely to diffuse away, it would better approximate a localized accumulation of the protease in vivo than similarly delivered soluble preparations.

Recombinant protease MH2, F, prostasin, O, and neuropsin or any other protease can be separated from other cellular proteins by use of an immunoaffinity column made with monoclonal or polyclonal antibodies specific for full-length protease, or polypeptide fragments thereof. Monospecific antibodies to protease MH2, F, prostasin, O, and neuropsin or any other protease are purified from mammalian antisera, or are prepared as monoclonal antibodies reactive with protease prostasin F, O, and neuropsin using the technique of (Kohler and Milstein (1976). *Eur J Immunol* 6:511–9).

Monospecific antibody as used herein is defined as a single antibody species or multiple antibody species with homogenous binding characteristics for protease prostasin F, O, and neuropsin. Homogenous binding as used herein refers to the ability of the antibody species to bind to a specific antigen or epitope, such as those associated with the protease MH2, F, prostasin, O, and neuropsin or any other protease, as described above. Protease MH2, F, prostasin, O, and neuropsin or any other protease specific antibodies are raised by immunizing animals such as mice, rats, guinea pigs, rabbits, goats, horses and the like, with rabbits being preferred, with an appropriate concentration of protease MH2, F, prostasin, O, and neuropsin or any other protease either with or without an immune adjuvant.

Generation of antiserum against proteins is well know by those skilled in the art, and is described for proteases MH2, F, prostasin, O, or neuropsin. Preimmune serum is collected prior to the first immunization. Each animal receives between about 0.001 mg and about 100.0 mg of the protease protein or peptide(s), derived from the deduced protease MH2, F, prostasin, O, or neuropsin DNA sequence or perhaps by the chemical degradation or enzymatic digestion of the protease protein itself, associated with an acceptable immune adjuvant. Such acceptable adjuvants include, but are not limited to, Freund's complete, Freund's incomplete, alum-precipitate, water in oil emulsion containing *Corynebacterium parvum* and tRNA, or Titermax (CytRx, Norcross, Ga.). The initial immunization consists of protease antigen in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of the antigen in Freund's incomplete adjuvant by the same route. Booster injections are given at about three-week intervals until maximal titers are obtained. At about 7 days after each booster immunization or about weekly after a single immunization, the animals are bled, the serum collected, and aliquots are stored at about −20° C.

Monoclonal antibodies (MoAb) reactive with protease MH2, F, prostasin, O, or neuropsin are prepared by immunizing inbred mice, preferably Balb/c, with protease protein or peptide(s), derived from the deduced protease MH2, F, prostasin, O, or neuropsin DNA sequence or perhaps by the chemical degradation or enzymatic digestion of the protease MH2, F, prostasin, O, or neuropsin protein itself. The mice are immunized by the IP or SC route with about 0.001 mg to about 1.0 mg, preferably about 0.1 mg, of protease antigen in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 0.001 to about 1.0 mg of protease antigen in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions that will allow the formation of stable hybridomas. Fusion partners may include, but are not limited to: mouse myelomas P3/NS1/Ag 4-1; MPC-11; S-194 and Sp 2/0, with Sp 2/0 being generally preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using protease or antigenic peptide(s) as the antigen. The culture fluids are also tested in the Ouchterlony precipitation assay to determine the isotype of the MoAb. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

Monoclonal antibodies are produced in vivo by injection of pristane primed Balb/c mice, approximately 0.5 ml per mouse, with about $2\times10^6$ to about $6\times10^6$ hybridoma cells about 4 days after priming. Ascites fluid is collected at approximately 8–12 days after cell transfer and the monoclonal antibodies are purified by techniques known in the art.

In vitro production of anti-protease MoAb is carried out by growing the hybridoma in DMEM containing about 2% fetal calf serum to obtain sufficient quantities of the specific MoAb. The monoclonal antibodies are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of protease MH2, F, prostasin, O, or neuropsin in body fluids or tissue and cell extracts.

It is readily apparent to those skilled in the art that the above described methods for producing monospecific antibodies may be utilized to produce antibodies specific for protease MH2, F, prostasin, O, or neuropsin polypeptide fragments, or full-length nascent protease polypeptide. Specifically, it is readily apparent to those skilled in the art that monospecific antibodies may be generated which are specific for only one or more protease MH2, F, prostasin, O, or neuropsin epitopes.

Protease MH2, F, prostasin, O, and neuropsin or any other protease antibody affinity columns are made by adding the antibodies to Affigel-10 (Bio-Rad), a gel support which is activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) and the cell culture supernatants or cell extracts containing proteases MH2, F, prostasin, O, and neuropsin or any other protease are slowly passed through the column. The column is then washed with phosphate buffered saline until the optical density ($A_{280}$) falls to background, then the protein is eluted with 0.23 M glycine-HCl (pH 2.6). The purified protease MH2, F, prostasin, O, and neuropsin or any other protease protein is then dialyzed against phosphate buffered saline.

Another method of expression for recombinant proteins produced by the zymogen activation construct is the in vitro transcription/translation systems (Promega, Madison, Wis.). The addition of canine pancreatic microsomal membranes would permit membrane translocation and core glycosylation of the expressed zymogen catalytic domains by in vitro transcription/translation. Although, these systems generally produce low amounts of translated product, in vitro translated zymogen catalytic domains of serine proteases with high specific activities could be detected following proteolytic activation. RNA transcribed from the zymogen activation construct in vitro may also be translated efficiently following microinjection into Xenopus laevis oocytes.

It is known that there is a substantial amount of redundancy in the various codons that code for specific amino acids. Therefore, this invention is also directed to those DNA sequences that contain alternative codons that code for the eventual translation of the identical amino acid. For purposes of this specification, a sequence bearing one or more replaced codons will be defined as a degenerate variation. Also included within the scope of this invention are mutations either in the DNA sequence or the translated protein that do not substantially alter the ultimate physical properties of the expressed protein. An example of such changes include substitution of an aliphatic for another aliphatic, aromatic for aromatic, acidic for another acidic, or a basic for another basic amino acid may not cause a change in functionality of the polypeptide. Also, more apparently radical substitutions may be made if the function of the residue is to maintain polypeptide solubility, including a charge reversal. It is known that DNA sequences coding for a peptide may be altered so as to code for a peptide having properties that are different than those of the naturally occurring peptide. Methods of altering the DNA sequences include, but are not limited to, site directed mutagenesis.

The S1 family of serine proteases is the largest family of peptidases (Rawlings and Barrett (1994). *Methods Enzymol* 244:19–61). As described above members of this diverse family perform diverse functions including food digestion, blood coagulation and fibrinolysis, complement activation as well as other immune or inflammatory responses. It is likely that these functions in both normal physiology and during diseased states, currently under investigation by numerous laboratories, will become better understood in the near future. These functions will undoubtedly be aided by the ability to express large amounts of the active protease, which is then amenable to biochemical analyses. In addition, the discovery of novel S1 serine protease cDNAs will enhance our understanding of the complex pathways controlled by these enzymes. The zymogen activation construct described herein will facilitate the future biochemical characterization of these novel genes.

The present invention is also directed to methods for screening for compounds that modulate the expression of DNA or RNA encoding protease T as well as the function of protease T protein in vivo. Compounds that modulate these activities may be DNA, RNA, peptides, proteins, or non-proteinaceous organic molecules. Compounds may modulate by increasing or attenuating the expression of DNA or RNA encoding protease T, or the function of protease T protein. Compounds that modulate the expression of DNA or RNA encoding protease T or the function of protease T protein may be detected by a variety of assays. The assay may be a simple "yes/no" assay to determine whether there is a change in expression or function. The assay may be made quantitative by comparing the expression or function of a test sample with the levels of expression or function in a standard sample. Modulators identified in this process are potentially useful as therapeutic agents. Methods for detecting compounds that modulate protease T proteolytic activity comprise combinding compound, protease T and a suitable labeled substrate and monitoring an effect of the compound on the the protease by changes in the amount of substrate as a function of time. Labeled substrates include, but are not limited to, substrate that are radiolabeled (Coolican et al. (1986). J. Biol. Chem. 261:4170–6), fluorimetric (Lonergan et al. (1995). J. Food Sci. 60:72–3, 78; Twining (1984). Anal. Biochem. 143:30–4) or colorimetric (Buroker-Kilgore and Wang (1993). Anal. Biochem. 208:387–92). Zymography following SDS polyacrylamide gel electrophoresis (Wadstroem and Smyth (1973). Sci. Tools 20:17–21), as well as by fluorescent resonance energy transfer (FRET)-based methods (Ng and Auld (1989). Anal. Biochem. 183:50–6) are also methods used to detect compounds that modulate protease T proteolytic activity. Compounds that are agonists will increase the rate of substrate degradation and will result in less remaining substrate as a function of time. Compounds that are antagonists will decrease the rate of substrate degradation and will result in greater remaining substrate as a function of time.

Kits containing the zymogen activation vector DNA may be prepared since these constructs will be generally useful to express, activate and characterize the activity of a wide variety of heterologous serine proteases. Such kits will be particularly beneficial, for example, to investigators in gene discovery for expressing novel serine proteases in order to determine their proteolytic specificity. Such a kit would comprise a compartmentalized carrier suitable to hold in close confinement at least one container. The carrier would further comprise reagents such as recombinant protein or antibodies suitable for detecting the expressed proteins. The carrier may also contain a means for detection such as labeled antigen or enzyme substrates or the like.

Kits containing antibodies to protease MH2, F, prostasin, O, and neuropsin or any other protease, or protease MH2, F, prostasin, O, and neuropsin or any other protease protein may be prepared. Such kits are used to detect the presence of protease protein or peptide fragments in a sample. Such characterization is useful for a variety of purposes including but not limited to forensic analyses, diagnostic applications, and epidemiological studies.

The recombinant protein and antibodies of the present invention may be used to screen and measure levels of protease MH2, F, prostasin, O, and neuropsin or any other protease DNA, protease MH2, F, prostasin, O, and neuropsin or any other protease RNA or protease MH2, F, prostasin, O, and neuropsin or any other protease protein. The recombinant proteins and antibodies lend themselves to the formulation of kits suitable for the detection and typing of protease MH2, F, prostasin, O, and neuropsin or any other protease. Such a kit would comprise a compartmentalized carrier suitable to hold in close confinement at least one container. The carrier would further comprise reagents such as recombinant protease protein or anti-protease antibodies suitable for detecting protease MH2, F, prostasin, O, or neuropsin protein. The carrier may also contain a means for detection such as labeled antigen or enzyme substrates or the like.

In addition, the use of the methodology described herein, has commercial value since it can be used to generate vast amounts of activated serine proteases which have the potential utility in biochemical reactions or as therapeutic proteins. Industrial scale production of zymogen activated constructs can be done, for example, in Bacillus or eukaryotic cells such as CHO, by techniques well known by those skilled in the art.

Protease MH2, F, prostasin, O, and neuropsin or any other protease gene therapy may be used to introduce enzymatically active protease MH2, F, prostasin, O, and neuropsin or any other protease into the cells of target organisms. The protease gene can be ligated into viral vectors that mediate transfer of the protease DNA by infection of recipient host cells. Suitable viral vectors include retrovirus, adenovirus, adeno-associated virus, herpes virus, vaccinia virus, poliovirus and the like. Alternatively, protease MH2, F, prostasin, O, and neuropsin or any other protease DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection. These procedures and variations thereof are suitable for ex vivo as well as in vivo protease gene therapy. Protease MH2, F, prostasin, O, and neuropsin or any other protease gene therapy may be particularly useful for the treatment of diseases where it is beneficial to elevate protease MH2, F, prostasin, O, and neuropsin or any other protease expression or activity.

Pharmaceutically useful compositions comprising protease MH2, F, prostasin, O, and neuropsin or any other protease protein, or modulators of protease MH2, F, prostasin, O, and neuropsin or any other protease activity, may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, or modulator.

Therapeutic or diagnostic compositions of the invention are administered to an individual in amounts sufficient to treat or diagnose disorders in which modulation of protease MH2, F, prostasin, O, and neuropsin or any other protease related activity is indicated. The effective amount may vary according to a variety of factors such as the individual's condition, weight, sex and age. Other factors include the mode of administration. The pharmaceutical compositions may be provided to the individual by a variety of routes such as subcutaneous, topical, oral and intramuscular.

The term "chemical derivative" describes a molecule that contains additional chemical moieties that are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages defined by routine testing in order to obtain optimal inhibition of the protease MH2, F, prostasin, O, and neuropsin or any other protease activity while minimizing any potential toxicity. In addition, co-administration or sequential administration of other agents may be desirable.

The protease MH2, F, prostasin, O, and neuropsin or any other protease may be formulated as an active ingredient in non-pharmaceutical commercial products including laundry detergents, skin care lotions or creams. In these formulations the protease MH2, F, prostasin, O, and neuropsin or any other protease is utilized to degrade proteins to increase the efficacy of the product. For example, in laundry detergent formulations inclusion of the protease MH2, F, prostasin, O, and neuropsin or any other protease would act as a "stain remover" by degrading proteacious contaminants from fabric such that the organic compound would become more soluble in detergent and water. Protease MH2, F, prostasin, O, and neuropsin or any other protease can be included in skin care products to aid in desquamation, the process of elimination of the superficial layers of the stratum corneum. An additional benefit of utilizing the protease MH2, F, prostasin, O, and neuropsin or any other protease in non-pharmaceutical commercial formulations is that it is not likely to induce allergic response in sensitive individuals since the protease MH2, F, prostasin, O, and neuropsin or any other protease is of human origin.

The present invention also has the objective of providing suitable topical, oral, systemic and parenteral pharmaceutical formulations for use in the novel methods of treatment of the present invention. The compositions containing compounds or modulators identified according to this invention as the active ingredient for use in the modulation of protease MH2, F, prostasin, O, and neuropsin or any other protease activity can be administered in a wide variety of therapeutic dosage forms in conventional vehicles for administration. For example, the compounds or modulators can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as a protease MH2, F, prostasin, O, and neuropsin or any other protease modulating agent.

The daily dosage of the products may be varied over a wide range from 0.01 to 1,000 mg per patient, per day. For oral administration, the compositions are preferably provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 100 mg/kg of body weight per day. The range is more particularly from about 0.001 mg/kg to 10mg/kg of body weight per day. The dosages of the protease MH2, F, prostasin, O, and neuropsin or any other protease modulators are adjusted when combined to achieve desired effects. On the other hand, dosages of these various agents may be independently optimized and combined to achieve a synergistic result wherein the pathology is reduced more than it would be if either agent were used alone.

Advantageously, compounds or modulators of the present invention may be administered in a single daily dose, or the total daily dosage may be administered in divided doses of two, three or four times daily. Furthermore, compounds or modulators for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds or modulators of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

In the methods of the present invention, the compounds or modulators herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents that may be employed include glycerin and the like. For parenteral administration, sterile suspensions and solutions are desired. Isotonic preparations, which generally contain suitable preservatives, are employed when intravenous administration is desired.

Topical preparations containing the active drug component can be admixed with a variety of carrier materials well known in the art, such as, eg., alcohols, aloe vera gel, allantoin, glycerine, vitamin A and E oils, mineral oil, PPG2 myristyl propionate, and the like, to form, eg., alcoholic solutions, topical cleansers, cleansing creams, skin gels, skin lotions, and shampoos in cream or gel formulations.

The compounds or modulators of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds or modulators of the present invention may also be coupled with soluble polymers as targetable drug carriers. Such polymers can include polyvinyl-pyrrolidone, pyran copolymer, polyhydroxypropylmethacryl-amidephenol, polyhydroxy-ethylaspartamidephenol, or polyethyleneoxidepolylysine substituted with palmitoyl residues. Furthermore, the compounds or modulators of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

For oral administration, the compounds or modulators may be administered in capsule, tablet, or bolus form or alternatively they can be mixed in the animals feed. The capsules, tablets, and boluses are comprised of the active ingredient in combination with an appropriate carrier vehicle such as starch, talc, magnesium stearate, or di-calcium phosphate. These unit dosage forms are prepared by intimately mixing the active ingredient with suitable finely-powdered inert ingredients including diluents, fillers, disintegrating agents, and/or binders such that a uniform mixture is obtained. An inert ingredient is one that will not react with the compounds or modulators and which is non-toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5% by weight of the active ingredient.

The compounds or modulators may alternatively be administered parenterally via injection of a formulation consisting of the active ingredient dissolved in an inert liquid carrier. Injection may be either intramuscular, intraruminal, intratracheal, or subcutaneous. The injectable formulation consists of the active ingredient mixed with an appropriate inert liquid carrier. Acceptable liquid carriers include the vegetable oils such as peanut oil, cottonseed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 10% by weight of the active ingredient.

Topical application of the compounds or modulators is possible through the use of a liquid drench or a shampoo containing the instant compounds or modulators as an aqueous solution or suspension. These formulations generally contain a suspending agent such as bentonite and normally will also contain an antifoaming agent. Formulations containing from 0.005 to 10% by weight of the active ingredient are acceptable. Preferred formulations are those containing from 0.01 to 5% by weight of the instant compounds or modulators.

Proteases are used in non-natural environments for various commercial purposes including laundry detergents, food processing, fabric processing, and skin care products. In laundry detergents, the protease is employed to break down organic, poorly soluble compounds to more soluble forms that can be more easily dissolved in detergent and water. In this capacity the protease acts as a "stain remover." Examples of food processing include tenderizing meats and producing cheese. Proteases are used in fabric processing, for example, to treat wool in order prevent fabric shrinkage. Proteases may be included in skin care products to remove scales on the skin surface that build up due to an imbalance in the rate of desquamation. Common proteases used in some of these applications are derived from prokaryotic or eukaryotic cells that are easily grown for industrial manufacture of their enzymes, for example a common species used is Bacillus as described in U.S. Pat. No. 5,217,878. Alternatively, U.S. Pat. No. 5,278,062 describes serine proteases isolated from a fungus, *Tritirachium album*, for use in laundry detergent compositions. Unfortunately use of some proteases is limited by their potential to cause allergic reactions in sensitive individuals or by reduced efficiency when used in a non-natural environment. It is anticipated that protease proteins derived from non-human sources would be more likely to induce an immune response in a sensitive individual. Because of these limitations, there is a need for alternative proteases that are less immunogenic to sensitive individuals and/or provides efficient proteolytic activity in a non-natural environment. The advent of recombinant technology allows expression of any species' proteins in a host suitable for industrial manufacture.

Another aspect of the present invention relates to compositions comprising the Protease MH2, F, prostasin, O, and neuropsin or any other protease and an acceptable carrier. The composition may be any variety of compositions that requires a protease component. Particularly preferred are compositions that may come in contact with humans, for example, through use or manufacture. The use of the Protease MH2, F, prostasin, O, and neuropsin or any other protease of the present invention is believed to reduce or eliminate the immunogenic response users and/or handlers might otherwise experience with a similar composition containing a known protease, particularly a protease of non-human origin. Preferred compositions are skin care compositions and laundry detergent compositions.

Herein, "acceptable carries" includes, but is not limited to, cosmetically-acceptable carriers, pharmaceutically-acceptable carriers, and carriers acceptable for use in cleaning compositions.

Skin Care Compositions

Skin care compositions of the present invention preferably comprise, in addition to the Protease MH2, F, prostasin, O, and neuropsin or any other protease, a cosmetically- or pharmaceutically-acceptable carrier.

Herein, "cosmetically-acceptable carrier" means one or more compatible solid or liquid filler diluents or encapsulating substances which are suitable for use in contact with the skin of humans and lower animals without undue toxicity, incompatibility, instability, irritation, allergic response, and the like, commensurate with a reasonable benefit/risk ratio.

Herein, "pharmaceutically-acceptable" means one or more compatible drugs, medicaments or inert ingredients which are suitable for use in contact with the tissues of humans and lower animals without undue toxicity, incompatibility, instability, irritation, allergic response, and the like, commensurate with a reasonable. benefit/risk ratio. Pharmaceutically-acceptable carriers must, of course, be of sufficiently high purity and sufficiently low toxicity to render them suitable for administration to the mammal being treated.

Herein, "compatible" means that the components of the cosmetic or pharmaceutical compositions are capable of being commingled with the Protease MH2, F, prostasin, O, and neuropsin or any other protease, and with each other, in a manner such that there is no interaction which would substantially reduce the cosmetic or pharmaceutical efficacy of the composition under ordinary use situations.

Preferably the skin care compositions of the present invention are topical compositions, i.e., they are applied topically by the direct laying on or spreading of the composition on skin. Preferably such topical compositions comprise a cosmetically- or pharmaceutically acceptable topical carrier.

The topical composition may be made into a wide variety of product types. These include, but are not limited to, lotions, creams, beach oils, gels, sticks, sprays, ointments, pastes, mousses, and cosmetics; hair care compositions such as shampoos and conditioners (for, e.g., treating/preventing dandruff); and personal cleansing compositions. These product types may comprise several carrier systems including, but not limited to, solutions, emulsions, gels and solids.

Preferably the carrier is a cosmetically or pharmaceutically acceptable aqueous or organic solvent. Water is a preferred solvent. Examples of suitable organic solvents include: propylene glycol, polyethylene glycol (200–600), polypropylene glycol (425–2025), propylene glycol-14 butyl ether, glycerol, 1,2,4butanetriol, sorbitol esters, 1,2,6-hexanetriol, ethanol, isopropanol, butanediol, and mixtures thereof. Such solutions useful in the present invention preferably contain from about 0.001% to about 25% of the Protease MH2, F, prostasin, O, and neuropsin or any other protease, more preferably from about 0.1% to about 10% more preferably from about 0.5% to about 5%; and preferably from about 50% to about 99.99% of an acceptable aqueous or organic solvent, more preferably from about 90% to about 99%.

Skin care compositions of the present invention may further include a wide variety of additional oil-soluble materials and/or water-soluble materials conventionally used in topical compositions, at their art-established levels. Such additional components include, but are not limited to: thickeners, pigments, fragrances, humectants, proteins and polypeptides, preservatives, pacifiers, penetration enhancing agents, collagen, hyaluronic acid, elastin, hydrolysates, primrose oil, jojoba oil, epidermal growth factor, soybean saponins, mucopolysaccharides, Vitamin A and derivatives thereof, Vitamin B2, biotin, pantothenic acid, Vitamin D, and mixtures thereof.

Cleaning Compositions

Cleaning compositions of the present invention preferably comprise, in addition to the Protease MH2, F, prostasin, O, and neuropsin or any other protease, a surfactant. The cleaning composition may be in a wide variety of forms, including, but not limited to, hard surface cleaning compositions, dish-care cleaning compositions, and laundry detergent compositions.

Preferred cleaning compositions are laundry detergent compositions. Such laundry detergent compositions include, but are not limited to, granular, liquid and bar compositions.

Preferably, the laundry detergent composition further comprises a builder.

The laundry detergent composition of the present invention contains the Protease MH2, F, prostasin, O, and neuropsin or any other protease at a level sufficient to provide a "cleaning-effective amount". The term "cleaning effective amount" refers to any amount capable of producing a cleaning, stain removal, soil removal, whitening, deodorizing, or freshness improving effect on substrates such as fabrics, dishware and the like. In practical terms for current commercial preparations, typical amounts are up to about 5 mg by weight, more typically 0.01 mg to 3 mg, of active enzyme per gram of the detergent composition. Stated another way, the laundry detergent compositions herein will typically comprise from 0.001% to 5%, preferably 0.01%–3%, more preferably 0.01% to 1% by weight of raw Protease MH2, F, prostasin, O, and neuropsin or any other protease preparation. Herein, "raw Protease MH2, F, prostasin, O, and neuropsin or any other protease preparation" refers to preparations or compositions in which the Protease MH2, F, prostasin, O, and neuropsin or any other protease is contained in prior to its addition to the laundry detergent composition. Preferably, the Protease MH2, F, prostasin, O, and neuropsin or any other protease is present in such raw Protease MH2, F, prostasin, O, and neuropsin or any other protease preparations at levels sufficient to provide from 0.005 to 0.1 Anson units (AU) of activity per gram of raw Protease MH2, F, prostasin, O, and neuropsin or any other protease preparation. For certain detergents, such as in automatic dishwashing, it maybe desirable to increase the active Protease MH2, F, prostasin, O, and neuropsin or any other protease content of the raw Protease MH2, F, prostasin, O, and neuropsin or any other protease preparation in order to minimize the total amount of non-catalytically active materials and thereby improve spotting/filming or other end-results. Higher active levels may also be desirable in highly concentrated detergent formulations.

Preferably, the laundry detergent compositions of the present invention, including but not limited to liquid compositions, may comprise from about 0.001% to about 10%, preferably from about 0.005% to about 8%, most preferably from about 0.01% to about 6%, by weight of an enzyme stabilizing system. The enzyme stabilizing system can be any stabilizing system that is compatible with the Protease MH2, F, prostasin, O, and neuropsin or any other protease, or any other additional detersive enzymes that may be included in the composition. Such a system may be inherently provided by other formulation actives, or be added separately, e.g., by the formulator or by a manufacturer of detergent-ready enzymes. Such stabilizing systems can, for example, comprise calcium ion, boric acid, propylene glycol, short chain carboxylic acids, boronic acids, and mixtures thereof, and are designed to address different stabilization problems depending on the type and physical form of the detergent composition.

The detergent composition also comprises a detersive surfactant. Preferably the detergent composition comprises at least about 0.01% of a detersive surfactant; more preferably at least about 0.1%; more preferably at least about 1%; more preferably still, from about 1% to about 55%.

Preferred detersive surfactants are cationic, anionic, nonionic, ampholytic, zwitterionic, and mixtures thereof, further described herein below. Non-limiting examples of detersive surfactants useful in the detergent composition include, the conventional C11–C18 alkyl benzene sulfonates ("LAS") and primary, branched-chain and random C10–C20 alkyl sulfates ("AS"), the C10–C18 secondary (2,3) alkyl sulfates of the formula $CH_3(CH_2)x(CHOSO_3-M+) CH_3$ and $CH_3 (CH_2)_y(CHOSO_3-M+) CH_2CH_3$ where x and (y+1) are integers of at least about 7, preferably at least about 9, and M is a water-solubilizing cation, especially sodium, unsaturated sulfates such as oleyl sulfate, the C10–C18 alkyl alkoxy sulfates ("AExS"; especially EO 1–7 ethoxy sulfates), C10–C18 alkyl alkoxy carboxylates (especially the EO 1–5 ethoxycarboxylates), the C10–18 glycerol ethers, the C10–C18 alkyl polyglycosides and their corresponding sulfated polyglycosides, and C12–C18 alpha-sulfonated fatty acid esters. If desired, the conventional nonionic and amphoteric surfactants such as the C12–C18 alkyl ethoxylates ("AE") including the so-called narrow peaked alkyl Ethoxylates and C6–C12 alkyl phenol alkoxylates (especially ethoxylates and mixed ethoxy/propoxy), C12–C18 betaines and solfobetaines ("sultaines"), C10–C18 amine oxides, and the like, can also be included in the overall compositions. The C10–C18 N-alkyl polyhydroxy fatty acid amides can also be used. Typical examples include the C12–C18 N-methylglucamides. See WO 9,206,154. Other sugar-derived surfactants include the N-alkoxy polyhydroxy fatty acid amides, such as C10–C18 N-(3-methoxypropyl) glucamide. The N-propyl through N-hexyl C12–C18 glucamides can be used for low sudsing. C10–C20 conventional soaps may also be used. If high sudsing is desired, the branched-chain C10–C16 soaps may be used. Mixtures of anionic and nonionic surfactants are especially useful. Other conventional useful surfactants are listed in standard texts.

Detergent builders are also included in the laundry detergent composition to assist in controlling mineral hardness. Inorganic as well as organic builders can be used. Builders are typically used in fabric laundering compositions to assist in the removal of particulate soils.

The level of builder can vary widely depending upon the end use of the composition and its desired physical form. When present, the compositions will typically comprise at least about 1% builder. Liquid formulations typically comprise from about 5% to about 50%, more typically about 5% to about 30%, by weight, of detergent builder. Granular formulations typically comprise from about 10% to about 80%, more typically from about 15% to about 50% by weight, of the detergent builder. Lower or higher levels of builder, however, are not excluded.

Inorganic or P-containing detergent builders include, but are not limited to, the alkali metal, ammonium and alkanolammonium salts of polyphosphates (exemplified by the tripolyphosphates, pyrophosphates, and glassy polymeric meta-phosphates), phosphonates, phytic acid, silicates, carbonates (including bicarbonates and sesquicarbonates), sulphates, and aluminosilicates. However, non-phosphate builders are required in some locales. Importantly, the compositions herein function surprisingly well even in the presence of the so-called "weak" builders (as compared with phosphates) such as citrate, or in the so-called "underbuilt" situation that may occur with zeolite or layered silicate builders.

Examples of silicate builders are the alkali metal silicates, particularly those having a SiO2:Na2O ration in the range 1.6:1 to 3.2:1 and layered silicates, such as the layered sodium silicates described in U.S. Pat. No. 4,664,839, issued May 12, 1987 to H. P. Rieck. NaSKS-6 is the trademark for a crystalline layered silicate marketed by Hoechst (commonly abbreviated herein as "SKS-6"). Unlike zeolite builders, the Na SKS-6 silicate builder does not contain aluminum. NaSKS-6 has the delta-Na2SiO5 morphology form of layered silicate. It can be prepared by methods such as those described in German DE-A-3,417,649 and DE-A-3,742,043. SKS-6 is a highly preferred layered silicate for use herein, but other such layered silicates, such as those having the general formula NaMSixO2x+1 yH20 wherein M is sodium or hydrogen, x is a number from 1.9 to 4, preferably 2, and y is a number from 0 to 20, preferably 0 can be used herein. Various other layered silicates from Hoechst include NaSKS-5, NaSKS-7 and NaSKS-11, as the alpha, beta and gamma forms. As noted above, the delta-Na2SiO5 (NaSKS-6 form) is most preferred for use herein. Other silicates may also be useful such as for example magnesium silicate, which can serve as a crispening agent in granular formulations, as a stabilizing agent for oxygen bleaches, and as a component of suds control systems.

Examples of carbonate builders are the alkaline earth and alkali metal carbonates as disclosed in German Patent Application No. 2,321,001 published on Nov. 15, 1973.

Aluminosilicate builders are useful in the present invention. Aluminosilicate builders are of great importance in most currently marketed heavy duty granular detergent compositions, and can also be a significant builder ingredient in liquid detergent formulations. Aluminosilicate builders include those having the empirical formula:

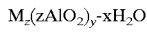

$$M_z(zAlO_2)_y \cdot xH_2O$$

wherein z and y are integers of at least 6, the molar ratio of z to y is in the range from 1.0 to about 0.5, and x is an integer from about 15 to about 264.

Useful aluminosilicate ion exchange materials are commercially available. These aluminosilicates can be crystalline or amorphous in structure and can be naturally-occurring aluminosilicates or synthetically derived. A method for producing aluminosilicate ion exchange materials is disclosed in U.S. Pat. No. 3,985,669, Krummel, et al, issued Oct. 12, 1976. Preferred synthetic crystalline aluminosilicate ion exchange materials useful herein are available under the designations Zeolite A, Zeolite P (b), Zeolite MAP and Zeolite X. In an especially preferred embodiment, the crystalline aluminosilicate ion exchange material has the formula:

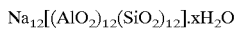

$$Na_{12}[(AlO_2)_{12}(SiO_2)_{12}] \cdot xH_2O$$

wherein x is from about 20 to about 30, especially about 27. This material is known as Zeolite A. Dehydrated zeolites (x=0–10) may also be used herein. Preferably, the aluminosilicate has a particle size of about 0.1–10 microns in diameter.

Organic detergent builders suitable for the purposes of the present invention include, but are not restricted to, a wide variety of polycarboxylate compounds. As used herein, "polycarboxylate" refers to compounds having a plurality of carboxylate groups, preferably at least 3 carboxylates. Polycarboxylate builder can generally be added to the composition in acid form, but can also be added in the form of a neutralized salt. When utilized in salt form, alkali metals, such as sodium, potassium, and lithium, or alkanolammonium salts are preferred.

Included among the polycarboxylate builders are a variety of categories of useful materials. One important category of poiycarboxylate builders encompasses the ether polycarboxylates, including oxydisuccinate, as disclosed in Berg, U.S. Pat. No. 3,128,287, issued Apr. 7, 1964, and Lamberti et al., U.S. Pat. No. 3,635,830, issued Jan. 18, 1972. See also "TMSFTDS" builders of U.S. Pat. No. 4,663,071, issued to Bush et al., on May 5, 1987. Suitable ether polycarboxylates also include cyclic compounds, particularly alicyclic compounds, such as those described in U.S. Pat. No. 3,923,679 to Rapko, issued Dec. 2, 1975; U.S. Pat. No. 3,835,163 to Rapko, issued Sep. 10, 1974; U.S. Pat. No. 4,158,635 to Crutchfield et al., issued Jun. 19, 1979; U.S. Pat. No. 4,120,874 to Crutchfield et al., issued Oct. 17, 1978; and U.S. Pat. No. 4,102,903 to Crutchfield et al., issued Jul. 25, 1978.

Other useful detergency builders include the ether hydroxypolycarboxylates, copolymers of maleic anhydride with ethylene or vinyl methyl ether, 1, 3, 5-trihydroxy benzene-2, 4, 6-t6sulphonic acid, and carboxymethyloxysuccinic acid, the various alkali metal, ammonium and substituted ammonium salts of polyacetic acids such as. ethylenediamine tetraacetic acid and nitrilotriacetic acid, as well as polycarboxylates such as Mellitic acid, succinic acid, oxydisuccinic acid, polymaleic acid, benzene 1,3,5-tricarboxylic acid, carboxymethyloxysuccinic acid, and soluble salts thereof, Citrate builders, e.g., citric acid and soluble salts thereof (particularly sodium salt), are polycarboxylate builders of particular importance for heavy-duty liquid detergent formulations due to their availability from renewable resources and their biodegradability. Citrates can also be used in granular compositions, especially in combination with zeolite and/or layered silicate builders. Oxydisuccinates are also especially useful in such compositions and combinations.

Also suitable in the detergent compositions of the present invention are the 3,3-dicarboxy-4-oxa-1,6-hexanedioates and the related compounds disclosed in U.S. Pat. No. 4,566,984 to Bush, issued Jan. 28, 1986. Useful succinic acid builders include the C5–C20 alkyl and alkenyl succinic acids and salts thereof. A particularly preferred compound of this type is dodecenylsuccinic acid. Specific examples of succinate builders include: laurylsuccinate, myristylsuccinate, paimitylsuccinate, 2-dodecenylsuccinate (preferred), 2pentadecenylsuccinate, and the like. Laurylsuccinates are the preferred builders of this group, and are described in European Patent Application 200,263 to Barrat et al., published Nov. 5, 1986.

Other suitable polycarboxylates are disclosed in U.S. Pat. No. 4,144,226, Crutchfield et al, issued Mar. 13, 1979 and in U.S. Pat. No. 3,308,067, Diehl, issued Mar. 7, 1967. See also U.S. Pat. No. 3,723,322 to Diehl, issued Mar. 27, 1973.

Fatty acids, e.g., C12–C18 monocarboxylic acids, can also be incorporated into the compositions alone, or in combination with the aforesaid builders, especially citrate and/or the succinate builders, to provide additional builder activity. Such use of fatty acids will generally result in a diminution of sudsing, which should be taken into account by the formulator.

In situations where phosphorus-based builders can be used, and especially in the formulation of bars used for hand-laundering operations, the various alkali metal phosphates such as the well-known sodium tripolyphosphates, sodium pyrophosphate and sodium orthophosphate can be used. Phosphonate builders such as ethane-1-hydroxy-1,1-diphosphonate and other known phosphonates (see, for example, U.S. Pat. No. 3,159,581 to Diehl, issued Dec. 1, 1964; U.S. Pat. No. 3,213,030 to Diehl, issued Oct. 19, 1965; U.S. Pat. No. 3,400,148 to Quimby, issued Sep. 3, 1968; U.S. Pat. No. 3,422,021 to Roy, issued Jan. 14, 1969; and U.S. Pat. No. 3,422,137 to Quimby, issued Jan. 4, 1969) can also be used.

Additional components which may be used in the laundry detergent compositions of the present invention include, but are not limited to: alkoxylated polycarboxylates (to provide, e.g., additional grease stain removal performance), bleaching agents, bleach activators, bleach catalysts, brighteners, chelating agents, clay soil removal/anti-redeposition agents, dye transfer inhibiting agents, additional enzymes (including lipases, amylases, hydrolases, and other proteases), fabric softeners, polymeric soil release agents, polymeric dispersing agents, and suds suppressors.

The compositions herein may further include one or more other detergent adjunct materials or other materials for assisting or enhancing cleaning performance, treatment of the substrate to be cleaned, or to modify the aesthetics of the detergent composition (e.g., perfumes, colorants, dyes, etc.). Non-limiting examples of such adjunct materials include, The detergent compositions herein may further comprise other known detergent cleaning components including alkoxylated polycarboxylates, bleaching compounds, brighteners, chelating agents, clay soil removal/antiredeposition agents, dye transfer inhibiting agents, enzymes, enzyme stabilizing systems, fabric softeners, polymeric soil release agents, polymeric dispersing agents, suds suppressors. The detergent composition may also comprise other ingredients including carriers, hydrotropes, processing aids, dyes or pigments, solvents for liquid formulations, solid fillers for bar compositions.

Method of Treating or Preventing Skin Flaking

Another aspect of the present invention relates to a method of treating or preventing skin flaking. The method comprises topical application of a safe and effective amount of a composition comprising the Protease MH2, F, prostasin, O, and neuropsin or any other protease.

Herein, "safe and effective amount" means an amount of Protease MH2, F, prostasin, O, and neuropsin or any other protease high enough to provide a significant positive modification of the condition to be treated, but low enough to avoid serious side effects (at a reasonable benefit/risk ratio), within the scope of sound medical judgment. A safe and effective amount of Protease MH2, F, prostasin, O, and neuropsin or any other protease will vary with the particular condition being treated, the age and physical condition of the subject being treated, the severity of the condition, the duration of the treatment, the nature of concurrent therapy and like factors.

The following examples illustrate the present invention without, however, limiting the same thereto.

EXAMPLE 1

Plasmid Manipulations:

All molecular biological methods were in accordance with those previously described (Sambrook, et al. *Molecular Cloning: A Laboratory Manual*, 2nd ed., (1989). 1–1626). Oligonucleotides were purchased from Ransom Hill Biosciences (Ransom Hill, Calif.)(Table 1) and all restriction endonucleases and other DNA modifying enzymes were from New England Biolabs (Beverly, Mass.) unless otherwise specified. Constructs were initially made in the pCDNA3 (InVitrogen, San Diego, Calif.) or the pCIneo (Promega, Madison. Wis.) vectors and subsequently transferred into Drosophila expression vectors pRM63 and pFLEX64 as described below. The Drosophila expression vectors used are similar to those commercially available (InVitrogen, San Diego, Calif.). All construct manipulations were confirmed by dye terminator cycle sequencing using Allied Biosystems 373 fluorescent sequencers (Perkin Elmer, Foster City, Calif.).

Pre Sequence Generation

The various modules used in the zymogen activation constructs are schematized in FIG. 1. The bovine prolactin pre sequence signal sequence fused upstream of the FLAG epitope in a manner similar to that previously described (Ishii, et al. (1993). *J Biol Chem* 268:9780–6). This sequence module was generated by designing a series of 5 double stranded oligonucleotides having cohesive overhangs. These oligonucleotides were kinased, paired (PF-#1U with PF-#10L, PF-#2U with PF-#9L, PF-#3U with PF-#8L, PF-#4U with PF-#7L, PF-#5U with PF-#6L; Table 1), in 500 mM NaCl and annealed in 5 separate reactions. Aliquots of the annealed oligonucleotides were combined, ligated and the product subjected to PCR with primers PF-#-1U and PF-#6L. This preparative reaction was performed using Amplitaq (Perkin Elmer, Foster City, Calif.) in the buffer supplied by the manufacturer with 10 cycles of 93° C. for 45 seconds/ 60° C. for 45 seconds/ 72° C. for 45 seconds, followed by 5 min at 72° C. The product was digested with Eco RI and Not I and ligated into the pCDNA3 vector cleaved with Eco RI and Not I followed by dephosphorylation with calf alkaline phosphatase. An isolate, containing the desired sequence designated prolactinFLAGpCDNA3 (PFpCDNA3) was used in subsequent manipulations. Additional pre sequences such as the human trypsinogen I and chymotrypsinogenFLAG (ChymoFLAG or CF) (FIG. 1) were generated by a direct double-stranded oligonucleotide insertion using the corresponding oligonucleotides (Table 1). Since these two pre sequences are shorter than that of prolactin, the annealed duplexes were designed to contain a 5'-Eco RI and a 3'-Not I cohesive ends and thereby could be inserted into the corresponding sites of pCDNA3 directly.

Most members of the S1 protease family contain a cysteine residue just upstream from the cleavage site of the pro sequence in a conserved region. This cysteine residue (Cys-1 by chymotrypsin numbering) is disulfide bonded to another conserved cysteine within the catalytic domain (Cys-122) (Matthews, et al. (1967). *Nature* (London) 214:652–6). We will refer to this class of S1 serine proteases as type II. It is possible that the existence of this catalytic cysteine residue 122 in the disulfide-bonded state is important for specific activity and/or substrate specificity. Consequently, in order to accommodate serine proteases of this type, we synthesized the CF pre sequence that will produce recombinant proteases containing a cysteine residue just upstream of the zymogen cleavage site.

Other pre sequences are suitable for use in the present invention as pre sequences for trafficking recombinant proteins into the secretory pathway of eukaryotic cells. These often include but are not limited to translational initiation methionine residues followed by a stretch of aliphatic amino acids. Export signal sequences target newly synthesized proteins to the endoplasmic reticulum of eukaryotic cells and the plasma membrane of bacteria. Although signal sequences contain a hydrophobic core region, they show great variation in both overall length and amino acid sequence. Recently, it has become clear that this variation allows signal sequences to specify different modes of targeting and membrane insertion. In the vast majority of instances, the signal peptide does not interfere with the secreted protein function following its cleavage by the signal peptidase (Martoglio and Dobberstein (1998). *Trends Cell Biol* 8:410–415). A variety of signal sequence modules, for general use in the secretion of expressed proteins, are currently commercially available (Invtirogen, San Diego, Calif.), and are suitable for use in the present invention as pre sequences.

Pro Sequence Generation

The EK cleavage site of human trypsinogen I was generated using the PCR with the two primers EK1-U and EK1-L (Table 1). The template was an EST (W40511) identified through FASTA searches (Pearson and Lipman (1988). *Proc Natl Acad Sci U. S. A.* 85:2444–8) of Db EST and obtained from the I.M.A.G.E. consortium through Genome Systems Inc., St. Louis, Mo. The purified plasmid DNA of W40511 was used as a template in preparative PCR reactions, with Amplitaq (Perkin Elmer, Foster City, Calif.) in accordance with the manufacturer's recommendations with 15 cycles of 93° C. for 45 seconds/ 53° C. for 45 seconds/ 72° C. for 45 seconds, followed by 5 min at 72° C. The PCR product was subcloned using the T/A vector pCR 2.1 (InVitrogen, San Diego, Calif.) and a clone with the desired sequence was chosen. The product was preparatively isolated by digestion using Not I and Xba I and subcloned downstream of the PF pre sequence between the Not I and Xba I sites in PFpCDNA3 to make PFEKpCDNA3. Additional pro sequences such as the FXa cleavage site and variations of the EK site (EK2 and EK3) were generated by direct double-stranded oligonucleotide insertions using the corresponding oligonucleotides. By design, these oligonucleotides once annealed would possess a 5'-Not I and a 3'-Xba I site such that they could be inserted into PFpCDNA3 or CFpCDNA3, which contain the prolactin-FLAG and chymotrypsinogenFLAG pre sequences respectively, to generate a series of pre-pro sequence modules such as PFFXapCDNA3 and CFEK2pcDNA3 etc.

The other class of S1 serine proteases can be generally defined by several smaller serine proteases like trypsin, prostate specific antigen, and stratum corneum chymotryptic enzyne. This class, we will refer to as type I, lack the cysteine residue just upstream of the cleavage site yet, contain a cysteine just downstream of the zymogen activation pro sequence. In the case of these trypsin-like S1 serine proteases, this cysteine (Cys-22 by chymotrypsinogen numbering) participates in disulfide bond formation with a cysteine in the catalytic domain (Cys-157) (Stroud, et al (1974). *J Mol Biol* 83:185–208, Kossiakoff et al. (1977). *Biochemistry* 16:654–64) and may have important consequences on catalytic activity and or substrate specificity. In order to accommodate this other type of serine protease, two more EK cleavage modules for the zymogen activation constructs were generated (FIG. 2).

Thus, to analyze the activity of a particular serine protease cDNA, the appropriate combination of pre-pro sequence that corresponds to the amino acid sequence of the particular serine protease, can be used. For example, the trypsin-like type I serine proteases could be expressed from a PFEK3 pre-pro sequence while a chymotrypsin-like type II protease may be better represented by the CFEK2 pre-pro modules.

Other pro sequences, and variations of them, are suitable for use in the present invention as pro sequences for cleavage by a restriction protease for activating the inactive zymogen produced by this system. These include, but are not limited to, the cleavage sites for the restriction proteases thrombin and PreScission™ Protease (Pharmacia Biotech Inc., Piscataway, N.J.).

C-terminal Affinity/Epitope Tags

Kinased, annealed double-stranded oligonucleotides, containing 5'-Xba I and 3'-Not I cohesive ends were designed corresponding to either a stop codon, 6 histidine codons and a C-terminal stop codon (6XHISTAG), or a Hemagglutinin epitope tag with a C-terminal stop codon (HATAG) (FIG. 1 and Table 1). These oligonucleotides were individually ligated between the Xba I and Not I sites in the plasmid vector pCI Neo (Promega, Madison, Wis.). Likewise, oligonucleotides were designed corresponding to the Hemagglutinin epitope tag but lacking a C-terminal stop codon (HA-Nonstop). This kinased annealed double-stranded oligonucleotide, containing Xba I cohesive termini, was reiteratively inserted upstream of the HATAG to generate a 3XHATAG epitope tag. In addition, the HA-Nonstop oligonucleotide was inserted upstream of the 6XHISTAG to generate a Hemagglutinin epitope/ 6XHIS affinity tag (HA6XHISTAG).

Zymogen Activation Vector Generation

The series of pre-pro sequences described above (ex. PFFXa or CFEK2 etc.) were preparatively excised from the pCDNA3 vector using Eco RI and Xba I. The FXa sequence, shown in Table 1 in particular, contains a Xba I site which becomes blocked by overlapping Dam methylation. To overcome this phenomenon, plasmid DNA of these FXa recombinants had to be transformed into and purified from a strain lacking Dam methylation (SCS110 for ex. Stratagene, La Jolla, Calif.) in order to cleave this site using the Xba I restriction enzyme. The pre-pro sequences were ligated into the various C-terminal epitope or affinity tagged pCIneo constructs between their 5'-Eco RI and 3'-Xba I sites. Thus, these constructs all feature a pre sequence (prolactin FLAG, PF; chymotrypsinogenFLAG, CF; or trypsinogen, T) to direct secretion in-frame with a pro sequence recognized by a restriction protease EK (sites EKI EK2 EK3); or factor Xa (site FXa), to permit the post-translational cleavage for zymogen activation. A unique Xba I restriction enzyme site immediately upstream of the epitope/affinity tags, described above, separates these pre-pro combinations (FIG. 2). Due to the nature of the design, the Xba I site is critical to these vectors, and was chosen based on several criteria as follows. These include the observation that the "6-cutter" (a restriction enzyme recognizing 6 nucleotide bases in its specific cleavage site) restriction enzyme Xba I site is found infrequently within cDNAs which greatly minimizes labor-intensive cloning steps in the generation of cDNA expression constructs for general use. Additionally, should one or more Xba I sites exist within a particular cDNA sequence one desires to insert into this vector, two other restriction enzymes (Spe I and Nhe I) are also rare 6-cutters which give rise to Xba I compatible cohesive ends. It should be noted that in this series of zymogen activation constructs, the translational register of the pre-pro sequences is distinct from that of the epitope/affinity tags. The resulting recombinants comprise a series of mammalian zymogen activation constructs in the pCIneo background. For increased levels of expression, these pre-pro-epitope modules were individually shuttled into vectors capable of expression in Drosophila S2 cells. This was accomplished by preparatively isolating the individual pre-pro-Xba I-epitope/affinity-tag modules by digesting the mammalian pCI Neo zymogen activation constructs with 5'-Eco RI and 3'-Hinc II. These modules were then inserted into the Eco RI and Hinc II sites of either an inducible Drosophila vector pRM63 containing the metallothionein promoter, or the constitutive Drosophila vector pFLEX64 containing the actin 5c promoter.

EXAMPLE 2

Acquisition of Serine Protease cDNAs

Acquisition of a Full Length cDNA Corresponding to the Serine Protease Prostasin The full length cDNA for prostasin (Yu, et al. (1995). J Biol Chem 270:13483–9) was identified through FASTA searches of Db EST (Genbank accession number AA205604) and obtained from the I.M.A.G.E. consortium through Genome Systems, Inc., St. Louis, Mo. The clone was sequenced for confirmation.

Acquisition of a Full Length cDNA Corresponding to the Novel Protease O

A putative full-length clone of a novel serine protease (Yoshida, et al., (1998). Biochim. Biophys. Acta, 1399:225–228), designated protease O, was cloned and sequenced for confirmation.

Acquisition of a Full Length cDNA Corresponding to the Human Orthologue of Protease Neuropsin A partial clone with homology to the murine neuropsin (Chen, et al. (1995). J Neurosci 15:5088–97) was also identified (Yoshida, et al., (1998). Gene, 213:9–16). The full-length cDNA of human neuropsin was obtained by screening a Uni-ZAP keratinocyte library, followed by in vivo excision and sequence analysis of positive purified plaques.

Acquisition of a Full Length cDNA Corresponding to Protease F/ESP-1

Homology searches identified a novel serine protease, we designated proteases F, within sequence nucleotide databases. An EST containing the full length cDNA for protease F was identified through FASTA searches of Db EST (Genbank accession number AA159101) and obtained from the I.M.A.G.E. consortium through Genome Systems, Inc., St. Louis, Mo. The clone was sequenced for confirmation. The nucleotide and deduced amino acid sequences were subsequently published (Inoue, et al. (1998). Biochem. Biophys. Res. Commun. 252:307–312) during the proceeding of our investigations.

Acquisition of the Protease MH2/Prostase Catalytic Domain

Homology searches identified a novel serine protease we designated proteases MH2 within sequence nucleotide databases. This particular serine protease was of interest since expression profiling had indicated prostate specific expression. We employed the 3' and 5' rapid amplification of cDNA ends (RACE) method in an attempt the isolate the full length protease MH2 cDNA using prostate marathon ready cDNA and random primed 5'-adapter-linked prostate cDNA (Clontech, Palo Alto, Calif.). Despite numerous attempts, we were only able to obtain clones which contained the protease MH2 catalytic domain and lacked the initiation methionine and signal sequence. The nucleotide and deduced amino acid sequences were subsequently published (Nelson et al. (1999). Proc. Natl. Acad. Sci. U. S. A. 96:3114–3119) during the proceeding of our investigations.

General Plasmid Manipulation

The purified plasmid DNA of these serine protease cDNAs was used as a template in 100 ul preparative PCR reactions with Amplitaq (Perkin Elmer, Foster City, Calif.) or Pfu DNA polymerase (Stratagene, La Jolla, Calif.) in accordance with the manufacturer's recommendations. Typically, reactions were run at 18 cycles of 93° C. for 30 seconds/ 53 to 65° C. for 30 seconds/ 72° C. for 90 seconds, followed by 5 min at 72° C. using the Pfu DNA polymerase. The annealing temperatures used were determined for the particular construct by the PrimerSelect 3.11 program (DNASTAR Inc., Madison, Wis.). The primers of the respective serine proteases (Table 1), containing Xba I cleavable ends, were designed to flank the catalytic domains of these three proteases and generate Xba I catalytic cassettes (FIG. 1). Since the protease prostasin is initially thought to be C-terminally membrane bound, and subsequently rendered soluble through proteolysis following secretion (Yu, et al. (1995). J Biol Chem 270:13483–9), a soluble form of prostasin was generated. This was accomplished by excluding the C-terminal 29 amino acids in the prostasin catalytic cassette by designing the C-terminal Xba I primer (prostasin(SOL) Xba-L, Table 1) to a position immediately upstream from the hydrophobic stretch of amino acids thought to represent a membrane tether.

The preparative PCR products were phenol/CHCl3 (1:1) extracted once, CHCl3 extracted, and then EtOH precipitated with glycogen (Boehringer-Mannheim Corp., Indianapolis, Ind.) carrier. The precipitated pellets were rinsed with 70% EtOH, dried by vacuum, and resuspended in 80 ul H20, 10 ul 10 restriction buffer number 2 and 1 ul 100×BSA (New England Biolabs, Beverly, Mass.). The products were digested for at least 3 hours at 37° C. with 200 units Xba I restriction enzyme (New England Biolabs, Beverly, Mass.). The Xba I digested products were phenol/ CHCl3 (1:1) extracted once, CHCl3 extracted, EtOH precipitated rinsed with 70% EtOH, and dried by vacuum. For purification from contaminating template plasmid DNA, the products were electrophoresed through 1.0% low melting temperature agarose (Life Technologies, Gaithersberg, Md.) gels in TAE buffer (40 mM Tris-Acetate, 1 mM EDTA pH 8.3) and excised from the gel. Aliquots of the excised products were routinely used for in-gel ligations with the appropriate Xba I digested, dephosphorylated and gel purified, zymogen activation vector. These cassettes once inserted, in the correct orientation, placed them in the proper translational register with the NH2-terminal prepro sequence and C-terminal/epitope affinity tag. PCR products directly cloned, as described above, were sequenced for confirmation. Only clones having confirmed sequences were chosen to isolate the Xba I catalytic cassette for subsequent subcloning into additional vectors of the series when desired.

EXAMPLE 3
Expression of Recombinant Serine Proteases in Drosophila S2 Cells

The recombinant bacmid containing the zymogen activated constructs were prepared from bacterial transformation, selection, growth, purification and PCR confirmation in accordance with the manufacturer's recommendations. Cultured Sf9 insect cells (ATCC CRL-1711) were transfected with purified bacmid DNA and several days later, conditioned media containing recombinant zymogen activated baculovirus was collected for viral stock amplification. Sf9 cells growing in Sf-900 II SFM at a density of $2 \times 10^6$/ml were infected at a multiplicity of infection of 2 at 27° C. for 80 hours, and cell pellets were collected for purification of the zymogen activated constructs.

EXAMPLE 4
Purification, and Activation of Recombinant Serine Proteases

Cells were lysed on ice in 20 mM Tris (pH7.4), 150 mM NaCl, 1% Triton X-100, 1 mM EDTA, 1 mM EGTA, 1 mM PMSF, leupeptin (1 µg/ml), and pepstatin (1 µg/ml). Cell lysates were mixed with anti-FLAG M2 affinity gel (Eastman Kodak Co., New Haven, Conn.) and bound at 4° C. for 3 hours with gentle rotation. The zymogen-bound resin was washed 3 times with TBS buffer (50 mM Tris-HCl, 150 mM NaCl at a final pH of 7.5), and eluted by competition with FLAG peptide (100 µg/ml) in TBS buffer. The eluted zymogen was dialyzed overnight against TBS in Spectra/Por membrane (MWCO: 12,000–14,000) (Spectra Medical Industries, Inc., Huston, Tex.). Ni-NTA (150 µl of a 50% slurry/per 100 µg of zymogen) (Qiagen, Valencia, Calif.) was added to 5 ml the dialyzed sample and mixed by shaking at 4° C. for 60 minutes The zymogen-bound resin was washed 3 times with wash buffer [10 mM Tris-HCl (pH 8.0), 300 mM NaCl, and 15 mM imidazole], followed by with a 1.5 ml wash with ds H$_2$O. Zymogen cleavage was carried out by adding enterokinase (10 U per 50 µg of zymogen) (Novagen, Inc., Madison Wis.; or Sigma, St. Louis, Mo.) to the zymogen-bound Ni-NTA beads in a small volume at room temperature overnight with gentle shaking in a buffer containing 20 mM Tris-HCl (pH 7.4), 50 mM NaCl, and 2.0 mM CaCl$_2$. The resin was then washed twice with 1.5 ml wash buffer. The activated protease was eluted with elution buffer [20 mM Tris-HCl (pH 7.8), 250 mM NaCl, and 250 mM imidazole]. Eluted protein concentration was determined by a Micro BCA Kit (Pierce, Rockford, Ill.) using bovine serum albumin as a standard. Amidolytic activities of the activated protease was monitored by release of para-nitroaniline (pNA) from the synthetic substrates indicated in Table 2. The chromogenic substrates used in these studies were all commercially available (Bachem California Inc., Torrance, PA; American Diagnostica Inc., Greenwich, Conn.; Kabi Pharmacia Hepar Inc., Franklin, Ohio). Assay mixtures contained chromogenic substrates at 500 uM and 10 mM Tris-HCl (pH 7.8), 25 mM NaCl, and 25 mM imidazole. Release of pNA was measured over 120 minutes at 37° C. on a micro-plate reader (Molecular Devices, Menlo Park, Calif.) with a 405 nm absorbance filter. The initial reaction rates (Vmax, mOD/min) were determined from plots of absorbance versus time using Softmax (Molecular Devices, Menlo Park, Calif.). The specific activities (nmole pNA produced /min/ug protein) of the activated proteases for the various substrates are presented in Table 2. No measurable chromogenic amidolytic activity was detected with the purified unactivated zymogens.

EXAMPLE 5
Electrophoresis and Western Blotting Detection of Recombinant Serine Proteases Samples of the purified zymogens or activated proteases, denatured in the presence or absence of the reducing agent dithiothreitol (DTT), were analyzed by SDS-PAGE (Bio Rad, Hercules Calif.) stained with Coomassie Brilliant Blue. For Western Blotting, the Flag-tagged serine proteases expressed from transient or stable S2 cells were detected with anti-Flag M2 antibody (Babco, Richmond, Calif.). The secondary antibody was a goat-anti-mouse IgG (H+L), horseradish peroxidase-linked F(ab')2 fragment, (Boehringer Mannheim Corp., Indianapolis, Ind.) and was detected by the ECL kit (Amersham, Arlington Heights, Ill.). FIG. 7 demonstrates PFEK2-prostasin-6XHIS function by demonstrating the quantitative cleavage of the expressed and purified zymogen to generate the processed and activated protease. Since the FLAG epitope is located just upstream of the of the EK pro sequence, cleavage with EK generates a FLAG-containing polypeptide which is too small to be retained in the polyacrylamide gel, and is therefore not detected in the +EK lanes. Also shown in panel B, the untreated or EK digested PFEK2-prostasin-6XHIS was denatured in the absence of DTT, in order to retain disulfide bonds, prior to electrophoresis (lanes 3 and 4). Although equivalent amounts of sample were loaded into each lane of the gel in the Western blot of B, the anti-FLAG MoAb M2 appears to detect proteins better when pretreated with DTT (compare lane B1 with B3). FIG. 8 demonstrates CFEK2-prostasin-6XHIS function by demonstrating the quantitative cleavage of the expressed and purified zymogen to generate the processed and activated protease. Since the FLAG epitope is located just upstream of the of the EK2 pro sequence, cleavage with EK generates a FLAG-containing polypeptide which is too small to be retained in the polyacrylamide gel, and is therefore not detected in the +EK lanes. Also shown in panel B, the untreated or EK digested CFEK2-prostasin-6XHIS was denatured in the absence of DTT, in order to retain disulfide bonds, prior to electrophoresis (lanes 3 and 4). Of significance in lane 4 is the retention of the FLAG epitope indicating the formation of a disulfide bond between the cysteine in the CF pre sequence with a cysteine in the catalytic domain of prostasin which is presumably Cys-122 (chymotrypsin numbering). Retention of the FLAG epitope, following EK cleavage and denaturation without DTT, is not observed using the prolactin pre sequence which lacks a cysteine residue (Compare lane 4 of FIG. 7 with lane 4 of FIG. 8). This documents that the CF pre sequence is capable of forming a light chain, that is disulfide bonded to the heavy catalytic chain of the recombinant serine proteases, when expressed in this system. It appears that in the absence of the reducing agent DTT, the EK cleaved polypeptides have a reproducibly decreased mobility in the gel (compare lane B3 with B4). FIG. 9 demonstrates function of PFEK1-neuropsin-6XHIS by demonstrating quantitative cleavage of the expressed and purified zymogen to generate the processed and activated protease. FIG. 10 demonstrates function of PFEK1-protease O-6XHIS by demonstrating quantitative cleavage of the expressed and purified zymogen to generate the processed and activated protease. FIG. 11 demonstrates function of PFEK1-protease F-6XHIS by demonstrating quantitative cleavage of the expressed and purified zymogen to generate the processed and activated protease. FIG. 12 demonstrates function of PFEK1-protease MH2-6XHIS by demonstrating quantitative cleavage of the expressed and purified zymogen to generate the processed and activated protease.

EXAMPLE 6

Chromogenic Assay

Amidolytic activities of the activated serine proteases are monitored by release of para-nitroaniline (pNA) from synthetic substrates that are commercially available (Bachem California Inc., Torrance, Pa.; American Diagnostica Inc., Greenwich, Conn.; Kabi Pharmacia Hepar Inc., Franklin, Ohio). Assay mixtures contain chromogenic substrates in 500 uM and 10 mM TRIS-HCl (pH 7.8), 25 mM NaCl, and 25 mM imidazole. Release of pNA is measured over 120 min at 37° C. on a micro-plate reader (Molecular Devices, Menlo Park, Calif.) with a 405 nm absorbance filter. The initial reaction rates (Vmax, mOD/min) are determined from plots of absorbance versus time using Softmax (Molecular Devices, Menlo Park, Calif.). Compounds that modulate a serine protease of the present invention are identified through screening for the acceleration, or more commonly, the inhibition of the proteolytic activity. Although in the present case chromogenic activity is monitored by an increase in absorbance, fluorogenic assays or other methods such as FRET to measure proteolytic activity as mentioned above, can be employed. Compounds are dissolved in an appropriate solvent, such as DMF, DMSO, methanol, and diluted in water to a range of concentrations usually not exceeding 100 uM and are typically tested, though not limited to, a concentration of 1000-fold the concentration of protease. The compounds are then mixed with the protein stock solution, prior to addition to the reaction mixture. Alternatively, the protein and compound solutions may be added independently to the reaction mixture, with the compound being added either prior to, or immediately after, the addition of the protease protein.

TABLE 1

| SEQ. ID. NO.: | Oligo Name | Sequence |
| --- | --- | --- |
| 15 | Stop-U | CTAGATAGC |
| 16 | Stop-L | GGCCGCTAT |
| 17 | HA-Stop-U | CTAGATACCCCTACGATGTGCCCGATTACGCCTAGC |
| 18 | HA-Stop-L | GGCCGCTAGGCGTMTCGGGCACATCGTAGGGGTAT |
| 19 | HA-Nonstop-U | CTAGATACCCCTACGATGTGCCCGATTACGCCG |
| 20 | HA-Nonstop-L | CTAGCGGCGTMTCGGGCACATCGTAGGGGTAT |
| 21 | 6XHIS-U | CTAGACATCACCATCACCATCACTAGC |
| 22 | 6XH IS-L | GGCCGCTAGTGATGGTGATGGTGATGT |
| 23 | PF-#1U | TGMTTCACCACCATGGACAGCAAAGGTTCGTCG |
| 24 | PF-#2U | CAGAAAGGGTCCCGCCTGCTCCTGCTGCTG |
| 25 | PF-#3U | GTGGTGTCAMTCTACTCTTGTGCCAGGGT |
| 26 | PF-#4U | GTGGTCTCCGACTACGGACGACGACGAC |
| 27 | PF-#5U | GTGGACGCGGCCGCATTATTA |
| 28 | PF-#6L | TMTMTGCGGCCGCGTCCACGTCGTCGTCGTCCT |
| 29 | PF-#7L | TGTAGTCGGAGACCACACCCT |
| 30 | PF-#8L | GGCACMGAGTAGATTTGACACCACCAGCA |
| 31 | PF-#9L | GCAGGAGCAGGCGGGACCCTTTCTGCGACG |
| 32 | PF-#10L | AACCTTTGCTGTCCATGGTGGTGAATTCA |
| 33 | Trypl Pre-U | AATTCACCATGAATCCACTCCTGATCCTTACCTTTGTCGC |
| 34 | Trypl Pre-L | GGCCGCCACMAGGTMGGATCAGGAGTGGATTCATGGTG |
| 35 | CF-#1U | AATTCACCACCATGGCTTTCCTCTGGCTCCTCTCCTGCTGGGCCCTCCTGGGTAC |
| 36 | CF-#2L | CCAGGAGGGCCCAGCAGGAGAGGAGCCAGAGGAAAGCCATGGTGGTG |
| 37 | CF-#3U | CACCTTCGGCTGCGGGGTCCCCGACTACAAGGACGACGACGC |
| 38 | CF-#4L | GGCCGCGTCGTCGTCGTCCTTGTAGTCGGGGACCCCGCAGCCGMGGTGGTAC |
| 39 | EK1-U | GTGGCGGCCGCTCTTGCTGCCCCCTTTGA |
| 40 | EK1-L | TTCTCTAGACAGTTGTAGCCCCCAACGA |
| 41 | Ek2-U | GGCCGCTCUGCTGCCCCCTUGATGATGATGACAAGATCGUGGGGGOTATGCT |
| 42 | EK2-L | CTAGAGCATAGCCCCCAACGATCGTCATCATCATCAAGGGGGCAGCAAGAGC |
| 43 | EK3-U | GGCCGCTCUGCTGCCCCCUTGATGATGATGACAAGATCGTTGGGGGCTATTGT |

TABLE 1-continued

| 44 | EK2-L | CTAGACAATAGCCCCCAACGATCUGTCATCATCATCA AAGGGGGCAGCAAGAGC |
| --- | --- | --- |
| 45 | FXa-U | GGCCGCTCUGCTGCCCCCUTATCGAGGGGCGCAT TGTGGAGGGCTCGGAT |
| 46 | FXa-L | CTAGATCCGAGCCCTCCACAATGCGCCCCTCGATAAA GGGGGCAGCMGAGC |
| 47 | prostasin Xba-U | AGCAGTCTAGAGGCCGGTCAGTGGCCCTGGCA |
| 48 | prostasin(SOL) Xba-L | GCTGGTCTAGAGCTGMGGCCAGGTGGC |
| 49 | neuropsin Xba-U | GGTATCTAGAGCCCUGCTGCCTATGATC |
| 50 | neuropsin Xba-L | ACTGTCTAGMCCCCAUCGCAGCCUGGC |
| 51 | protease O Xba-U | TCGATCTAGAAAAGCACTCCCAGCCCTGGCAG |
| 52 | protease O Xba-L | GTCCTCTAGMUGUCUCATCGTCTCCTGG |

| Protease cDNA | Genbank Acc.# |
| --- | --- |
| h Trypsinogen I | W40511 |
| h Prostasin | AA205604 |
| h Neuropsin | 2604309 |
| h Protease O | 2723646 |

TABLE 2

| Recombinant Protease | H-D-Pro-HHT-Arg-pNA | H-D-Lys (CBO)-Pro-Arg-pNA | H-D-Val-Leu-Lys-pNA | H-DL-Val-Leu-Arg-pNA |
| --- | --- | --- | --- | --- |
| PFEK2-prostasin-6XHIS | 0.055± 0.002 | 0.870± 0.022 | N. D. | 0.251± 0.005 |
| CFEK2-prostasin-6XHIS | 0.116± 0.011 | 1.317± 0.024 | N. D. | 0.384± 0.003 |
| PFEK1-neuropsin-6XHIS | 0.463± 0.014 | 0.731± 0.004 | 0.158± 0.001 | 0.938± 0.002 |
| PFEK1-protease O-6XHIS | 0.058± 0.002 | 0.022± 0.000 | N. D. | 0.006± 0.000 |
| PFEK-MH2-6XHIS | 0.052± 0.000 | 0.893± 0.067 | 0.121± 0.054 | 0.058± 0.002 |
| CFEK2-Prot.F-6XHIS | 0.016± 0.001 | 0.045± 0.006 | N. D. | N. D. |

References Cited

Altschul, S. F., Gish, W., Miller, W., Myers, E. W., and Lipman, D. J. (1990). Basic local alignment search tool. J. Mol. Biol. 215, 403–10.

Chen, Z. -L., Yoshida, S., Kato, K., Momota, Y., Suzuki, J., Tanaka, T., Ito, J., Nishino, H., Aimoto, S., Kiyama, H., and Shiosaka, S. (1995). Expression and activity-dependent changes of a novel limbic-serine protease gene in the hippocampus. J. Neurosci. 15, 5088–97.

Davie, E. W., Fujikawa, K., and Kisiel, W. (1991). The coagulation cascade: initiation, maintenance, and regulation. Biochemistry 30, 10363–70.

Hansson, L., Stroemqvist, M., Baeckman, A., Wallbrandt, P., Carlstein, A., and Egelrud, T. (1994). Cloning, expression, and characterization of stratum corneum chymotryptic enzyme. A skin-specific human serine proteinase. J. Biol. Chem. 269, 19420–6.

Huber, R., and Bode, W. (1978). Structural basis of the activation and action of trypsin. Acc. Chem. Res. 11, 114–22.

Inoue, M., Kanbe, N., Kurosawa, M., and Kido, H. (1998). Cloning and tissue distribution of a novel serine protease esp-1 from human eosinophils. Biochem. Biophys. Res. Commun. 252, 307–312.

Ishii, K., Hein, L., Kobilka, B., and Coughlin, S. R. (1993). Kinetics of thrombin receptor cleavage on intact cells. Relation to signaling. J. Biol. Chem. 268, 9780–6.

Kitamoto, Y., Yuan, X., Wu, Q., McCourt, D. W., and Sadler, J. E. (1994). Enterokinase, the initiator of intestinal digestion, is a mosaic protease composed of a distinctive assortment of domains. Proc. Natl. Acad. Sci. U. S. A. 91, 7588–92.

Kossiakoff, A. A., Chambers, J. L., Kay, L. M., and Stroud, R. M. (1977). Structure of bovine trypsinogen at 1.9 ANG. resolution. Biochemistry 16, 654–64.

Kyte, J., and Doolittle, R. F. (1982). A simple method for displaying the hydropathic character of a protein. J. Mol. Biol. 157, 105–32.

Leytus, S. P., Loeb, K. R., Hagen, F. S., Kurachi, K., and Davie, E. W. (1988). A novel trypsin-like serine protease (hepsin) with a putative transmembrane domain expressed by human liver and hepatoma cells. Biochemistry 27, 1067–74.

Little, S. P., Dixon, E. P., Norris, F., Buckley, W., Becker, G. W., Johnson, M., Dobbins, J. R., Wyrick, T., Miller, J. R., Mackellar, W., Hepburn, D., Corvalan, J., Mcclure, D., Liu, X., Stephenson, D., Clemens, J., and Johnstone, E. M. (1997). Zyme, a novel and potentially amyloidogenic enzyme cDNA isolated from Alzheimer's disease brain. J. Biol. Chem. 272, 25135–25142.

Martoglio, B., and Dobberstein, B. (1998). Signal sequences: more than just greasy peptides. Trends Cell Biol. 8, 410–415.

Matthews, B. W., Sigler, P. B., Henderson, R., and Blow, D. M. (1967). Three-dimensional structure of tosyl-.alpha.-chymotrypsin. Nature (London) 214, 652–6.

Nelson, P. S., Gan, L., Ferguson, C., Moss, P., Gelinas, R., Hood, L., and Wang, K. (1999). Molecular cloning and characterization of prostase, an androgen-regulated serine protease with prostate-restricted expression. Proc. Natl. Acad. Sci. U. S. A. 96, 3114–3119.

Pearson, W. R., and Lipman, D. J. (1988). Improved tools for biological sequence comparison. Proc. Natl. Acad. Sci. U. S. A. 85, 2444–8.

Proud, D., and Kaplan, A. P. (1988). Kinin formation: mechanisms and role in inflammatory disorders. Annu. Rev. Immunol. 6, 49–83.

Rawlings, N. D., and Barrett, A. J. (1994). Families of serine peptidases. Methods Enzymol. 244, 19–61.

Reid, K. B. M., and Porter, R. R. (1981). The proteolytic activation systems of complement. Annual Review of Biochemistry 50, 433–464.

Sambrook, J., Fritsch, E. F., and Maniatis, T. (1989). Molecular Cloning: A Laboratory Manual, 2nd ed.: Cold Spring Harbor Laboratory, Cold Spring Harbor, N.Y.

Stroud, R. M., Kay, L. M., and Dickerson, R. E. (1974). Structure of bovine trypsin. Electron density maps of the inhibited enzyme at 5 ang. and 2.7 .ang. resolution. J. Mol. Biol. 83, 185–208.

Tachias, K., and Madison, E. L. (1996). Converting tissue-type plasminogen activator into a zymogen. J. Biol. Chem. 271, 28749–28752.

Takayama, T. K., Fujikawa, K., and Davie, E. W. (1997). Characterization of the precursor of prostate-specific antigen Activation by trypsin and by human glandular kallikrein. J. Biol. Chem. 272, 21582–21588.

Wang, Z. -m., Rubin, H., and Schechter, N. M. (1995). Production of active recombinant human chymase from a construct containing the enterokinase cleavage site of trypsinogen in place of the native propeptide sequence. Biol. Chem. Hoppe-Seyler 376, 681-4.

Wigler, M., Silverstein, S., Lee, L. -S., Pellicer, A., Cheng, Y. -C., and Axel, R. (1977). Transfer of purified Herpes virus thymidine kinase gene to cultured mouse cells. Cell (Cambridge, Mass.) 11, 223–32.

Yamashiro, K., Tsuruoka, N., Kodama, S., Tsujimoto, M., Yamamura, Y., Tanaka, T., Nakazato, H., and Yamaguchi, N. (1997). Molecular cloning of a novel trypsin-like serine protease (neurosin) preferentially expressed in brain. Biochim. Biophys. Acta 1350, 11–14.

Yoshida, S., Taniguchi, M., Hirata, A., and Shiosaka, S. (1998). Sequence analysis and expression of human neuropsin cDNA and gene. Gene 213, 9–16.

Yoshida, S., Taniguchi, M., Suemoto, T., Oka, T., He, X., and Shiosaka, S. (1998). cDNA cloning and expression of a novel serine protease, TLSP1. Biochim. Biophys. Acta 1399, 225–228.

Yu, J. X., Chao, L., and Chao, J. (1994). Prostasin is a novel human serine proteinase from seminal fluid. Purification, tissue distribution, and localization in prostate gland. J. Biol. Chem. 269, 18843–8.

Yu, J. X., Chao, L., and Chao, J. (1995). Molecular cloning, tissue-specific expression, and cellular localization of human prostasin mRNA. J. Biol. Chem. 270, 13483–9.

What is claimed is:

1. An expression vector comprising a nucleotide sequence encoding, in frame and in order, a pre sequence, a pro sequence, and an affinity tag sequence, and further comprising a cloning site for the in frame insertion of a protease catalytic domain-encoding cassette, wherein said expression vector comprises the nucleotide sequence set forth in SEQ ID NO:5.

2. The expression vector of claim 1 wherein said protease catalytic domain-encoding cassette inserted in frame into the cloning site encodes the catalytic domain of a membrane-bound protease but does not encode a transmembrane domain of said membrane-bound protease.

3. A recombinant host cell containing the expression vector of claim 2.

4. A process for expression of a zymogen, comprising:
   (a) transferring the expression vector of claim 2 into suitable host cells; and
   (b) culturing the host cells of step (a) under conditions that allow expression of the zymogen expression vector.

5. The process of claim 4, wherein said expression vector comprises a nucleotide sequence set forth in SEQ ID NO: 8.

6. A protease catalytic domain fusion protein produced from a recombinant host cell containing the expression vector of claim 2, wherein said protease catalytic domain fusion protein functions as a serine protease when said fusion protein is cleaved at the pre sequence.

7. The protease of claim 6, wherein said protease is bound to Ni-NTA silica or Ni-NTA agarose beads.

8. A protease catalytic domain fusion protein produced from a recombinant host cell containing the expression vector of claim 2 wherein the catalytic domain fusion protein comprises the amino acid sequence set forth in SEQ ID NO: 12.

9. A pharmaceutical composition comprising the serine protease catalytic domain of claim 8.

10. The pharmaceutical composition of claim 9 wherein said composition is a topical skin care composition.

11. A method of treating, either prophylactically or acutely, an imbalance of desquamation comprising topical application of the composition of claim 10.

12. A method for identifying compounds that modulate the activity of a protease expressed from the expression vector of claim 2, comprising:
   (a) combining a modulator of protease activity, protease protein, and a labeled substrate; and
   (b) measuring a change in the labeled substrate.

13. The method of claim 11 wherein the labeled substrate is selected from the group consisting of flourogenic, colormetric, radiometric, and fluorescent resonance energy transfer (FRET).

14. A kit comprising an expression vector selected from a group consisting of the expression vector of claim 1.

15. A kit comprising a nucleic acid sequence selected from the group consisting of SEQ ID NO: 5 and SEQ ID NO: 8.

16. A kit comprising a protease catalytic domain fusion protein comprising the amino acid sequence set forth in SEQ ID NO: 12.

* * * * *

SEQUENCE LISTING

```
<160> NUMBER OF SEQ ID NOS: 60

<210> SEQ ID NO 1
<211> LENGTH: 361
<212> TYPE: DNA
<213> ORGANISM: Artificial Sequence
<220> FEATURE:
<223> OTHER INFORMATION: Description of Artificial Sequence: Fusion gene
      vectors.

<400> SEQUENCE: 1
gaattcacca ccatggacag caaaggttcg tcgcagaaat cccgcctgct cctgctgctg         60
gtggtgtcaa atctactctt gtgccagggt gtggtctccg actacaagga cgacgacgac        120
gtggacgcgg ccgctcttgc tgcccccttt gatgatgatg acaagatcgt tgggggctat        180
gctctagata gcggccgctt ccctttagtg agggttaatg cttcgagcag acatgataag        240
atacattgat gagtttggac aaaccacaac tagaatgcag tgaaaaaaat gctttatttg        300
tgaaatttgt gatgctattg ctttatttgt aaccattata agctgcaata aacaagttga        360
c                                                                        361

<210> SEQ ID NO 2
<211> LENGTH: 301
<212> TYPE: DNA
<213> ORGANISM: Artificial Sequence
<220> FEATURE:
<223> OTHER INFORMATION: Description of Artificial Sequence: Fusion gene
      vectors.

<400> SEQUENCE: 2
gaattcacca tgaatccact cctgatcctt acctttgtgg cggccgctct tgctgccccc         60
tttgatgatg atgacaagat cgttgggggc tattgtctag ataccccctac gatgtgcccg       120 attacgccta gcggccgctt ccctttagtg agggttaatg cttcgagcag acatgataag        180
atacattgat gagtttggac aaaccacaac tagaatgcag tgaaaaaaat gctttatttg        240
tgaaatttgt gatgctattg ctttatttgt aaccattata agctgcaata aacaagttga        300
c                                                                        301
```

<210> SEQ ID NO 3
<211> LENGTH: 484
<212> TYPE: DNA
<213> ORGANISM: Artificial Sequence
<220> FEATURE:
<223> OTHER INFORMATION: Description of Artificial Sequence: Fusion gene
      vectors.

<400> SEQUENCE: 3

```
gaattcacca ccatggacag caaaggttcg tcgcagaaat cccgcctgct cctgctgctg      60
gtggtgtcaa atctactctt gtgccagggt gtggtctccg actacaagga cgacgacgac     120
gtggacgcgg ccgctcttgc tgccccttt atcgaggggc gcattgtgga gggctcggat      180
ctagatacc ctacgatgtg cccgattacg ccgctagata ccctacgat gtgcccgatt       240
acgccgctag ataccactac gatgtgcccg attacgccgc tagatacccc tacgatgtgc     300
ccgattacgc ctagcggccg cttcccttta gtgagggtta atgcttcgag cagacatgat     360
aagatacatt gatgagtttg acaaaccac aactagaatg cagtgaaaaa aatgctttat      420
ttgtgaaatt tgtgatgcta ttgctttatt tgtaaccatt ataagctgca ataaacaagt     480
tgac                                                                  484
```

<210> SEQ ID NO 4
<211> LENGTH: 382
<212> TYPE: DNA
<213> ORGANISM: Artificial Sequence
<220> FEATURE:
<223> OTHER INFORMATION: Description of Artificial Sequence: Fusion gene
      vectors.

<400> SEQUENCE: 4

```
gaattcacca ccatggacag caaaggttcg tcgcagaaat cccgcctgct cctgctgctg      60
gtggtgtcaa atctactctt gtgccagggt gtggtctccg actacaagga cgacgacgac     120
gtggacgcgg ccgctcttgc tgccccttt gatgatgatg acaagatcgt tggggctac       180
aactgtctag acatcaccat caccatcact agcggccgct tccctttagt gagggttaat     240
gcttcgagca gacatgataa gatacattga tgagtttgga caaaccacaa ctagaatgca    300
gtgaaaaaaa tgctttattt gtgaaatttg tgatgctatt gctttatttg taaccattat    360
aagctgcaat aaacaagttg ac                                              382
```

<210> SEQ ID NO 5
<211> LENGTH: 352
<212> TYPE: DNA
<213> ORGANISM: Artificial Sequence
<220> FEATURE:
<223> OTHER INFORMATION: Description of Artificial Sequence: Fusion gene
      vectors.

<400> SEQUENCE: 5

```
gaattcacca ccatggcttt cctctggctc ctctcctgct gggccctcct gggtaccacc      60
ttcggctgcg gggtccccga ctacaaggac gacgacgacg cggccgctct tgctgccccc     120
tttgatgatg atgacaagat cgttggggc tatgctctag acatcaccat caccatcact     180
agcggccgct tccctttagt gagggttaat gcttcgagca gacatgataa gatacattga    240
tgagtttgga caaaccacaa ctagaatgca gtgaaaaaaa tgctttattt gtgaaatttg    300
tgatgctatt gctttatttg taaccattat aagctgcaat aaacaagttg ac            352
```

<210> SEQ ID NO 6
<211> LENGTH: 385

```
<212> TYPE: DNA
<213> ORGANISM: Artificial Sequence
<220> FEATURE:
<223> OTHER INFORMATION: Description of Artificial Sequence: Fusion gene
      vectors.

<400> SEQUENCE: 6
gaattcacca ccatggcttt cctctggctc ctctcctgct gggccctcct gggtaccacc       60
ttcggctgcg gggtccccga ctacaaggac gacgacgacg cggccgctct tgctgccccc      120
tttgatgatg atgacaagat cgttgggggc tatgctctag ataccctac gatgtgcccg       180 attacgccgc tagacatcac catcaccatc actagcggcc gcttcccttt agtgagggtt      240
aatgcttcga gcagacatga taagatacat tgatgagttt ggacaaacca caactagaat      300
gcagtgaaaa aaatgcttta tttgtgaaat tgtgatgct attgctttat ttgtaaccat       360
tataagctgc aataaacaag ttgac                                            385

<210> SEQ ID NO 7
<211> LENGTH: 1169
<212> TYPE: DNA
<213> ORGANISM: Artificial Sequence
<220> FEATURE:
<223> OTHER INFORMATION: Description of Artificial Sequence: Fusion gene
      with homo sapien serine protease catalytic domain

<400> SEQUENCE: 7
gaattcacca ccatggacag caaaggttcg tcgcagaaat cccgcctgct cctgctgctg       60
gtggtgtcaa atctactctt gtgccagggt gtggtctccg actacaagga cgacgacgac      120
gtggacgcgg ccgctcttgc tgcccccttt gatgatgatg acaagatcgt tgggggctat      180
gctctagagg ccggtcagtg gccctggcag gtcagcatca cctatgaagg cgtccatgtg      240
tgtggtggct ctctcgtgtc tgagcagtgg gtgctgtcag ctgctcactg cttccccagc      300
gagcaccaca aggaagccta tgaggtcaag ctggggggccc accagctaga ctcctactcc      360
gaggacgcca aggtcagcac cctgaaggac atcatcccc accccagcta cctccaggag       420
ggctcccagg gcgacattgc actcctccaa ctcagcagac ccatcacctt ctcccgctac      480
atccggccca tctgcctccc tgcagccaac gcctccttcc caacggcct ccactgcact        540 gtcactggct ggggtcatgt ggccccctca gtgagcctcc tgacgccaa gccactgcag        600 caactcgagg tgcctctgat cagtcgtgag acgtgtaact gcctgtacaa catcgacgcc      660
aagcctgagg agccgcactt gtccaagag gacatggtgt gtgctggcta tgtggagggg       720
ggcaaggacg cctgccaggg tgactctggg ggcccactct cctgccctgt ggagggtctc      780
tggtacctga cgggcattgt gagctgggga gatgcctgtg ggcccgcaa caggcctggt       840 gtgtacactc tggcctccag ctatgcctcc tggatccaaa gcaaggtgac agaactccag      900
cctcgtgtgg tgccccaaac ccaggagtcc cagcccgaca gcaacctctg tggcagccac      960
ctggccttca gctctagaca tcaccatcac catcactagc ggccgcttcc ctttagtgag     1020
ggttaatgct tcgagcagac atgataagat acattgatga gtttggacaa accacaacta     1080
gaatgcagtg aaaaaaatgc tttatttgtg aaatttgtga tgctattgct ttatttgtaa     1140
ccattataag ctgcaataaa caagttgac                                       1169

<210> SEQ ID NO 8
<211> LENGTH: 1142
<212> TYPE: DNA
<213> ORGANISM: Artificial Sequence
<220> FEATURE:
```

-continued

<223> OTHER INFORMATION: Description of Artificial Sequence: Fusion gene
      with homo sapien serine protease catalytic domain

<400> SEQUENCE: 8

| | | | | | |
|---|---|---|---|---|---|
| gaattcacca | ccatggcttt | cctctggctc | ctctcctgct | gggccctcct | ggtaccacc | 60 |
| ttcggctgcg | gggtccccga | ctacaaggac | gacgacgacg | cggccgctct | tgctgccccc | 120 |
| tttgatgatg | atgacaagat | cgttgggggc | tatgctctag | aggccggtca | gtggccctgg | 180 |
| caggtcagca | tcacctatga | aggcgtccat | gtgtgtggtg | gctctctcgt | gtctgagcag | 240 |
| tgggtgctgt | cagctgctca | ctgcttcccc | agcgagcacc | acaaggaagc | ctatgaggtc | 300 |
| aagctggggg | cccaccagct | agactcctac | tccgaggacg | ccaaggtcag | caccctgaag | 360 |
| gacatcatcc | cccaccccag | ctacctccag | gagggctccc | agggcgacat | tgcactcctc | 420 |
| caactcagca | gacccatcac | cttctcccgc | tacatccggc | ccatctgcct | ccctgcagcc | 480 |
| aacgcctcct | tccccaacgg | cctccactgc | actgtcactg | gctgggtca | tgtggccccc | 540 |
| tcagtgagcc | tcctgacgcc | caagccactg | cagcaactcg | aggtgcctct | gatcagtcgt | 600 |
| gagacgtgta | actgcctgta | caacatcgac | gccaagcctg | aggagccgca | ctttgtccaa | 660 |
| gaggacatgg | tgtgtgctgg | ctatgtggag | gggggcaagg | acgcctgcca | gggtgactct | 720 |
| ggggggcccac | tctcctgccc | tgtggagggt | ctctggtacc | tgacgggcat | tgtgagctgg | 780 |
| ggagatgcct | gtggggcccg | aacaggcct | ggtgtgtaca | ctctggcctc | cagctatgcc | 840 |
| tcctggatcc | aaagcaaggt | gacagaactc | agcctcgtg | tggtgcccca | acccaggag | 900 |
| tcccagcccg | acagcaacct | ctgtggcagc | cacctggcct | tcagctctag | acatcaccat | 960 |
| caccatcact | agcggccgct | tcccttagt | gagggttaat | gcttcgagca | gacatgataa | 1020 |
| gatacattga | tgagtttgga | caaaccacaa | ctagaatgca | gtgaaaaaa | tgctttattt | 1080 |
| gtgaaatttg | tgatgctatt | gctttatttg | taaccattat | aagctgcaat | aaacaagttg | 1140 |
| ac | | | | | 1142 |

<210> SEQ ID NO 9
<211> LENGTH: 1049
<212> TYPE: DNA
<213> ORGANISM: Artificial Sequence
<220> FEATURE:
<223> OTHER INFORMATION: Description of Artificial Sequence: Fusion gene
      with homo sapien serine protease catalytic domain

<400> SEQUENCE: 9

| | | | | | |
|---|---|---|---|---|---|
| gaattcacca | ccatggacag | caaaggttcg | tcgcagaaat | cccgcctgct | cctgctgctg | 60 |
| gtggtgtcaa | atctactctt | gtgccagggt | gtggtctccg | actacaagga | cgacgacgac | 120 |
| gtggacgcgg | ccgctcttgc | tgccccctt | gatgatgatg | acaagatcgt | tgggggctac | 180 |
| aactgtctag | aacccattc | gcagccttgg | caggcggcct | tgttccaggg | ccagcaacta | 240 |
| ctctgtggcg | gtgtccttgt | aggtggcaac | tgggtcctta | cagctgccca | ctgtaaaaaa | 300 |
| ccgaaataca | cagtacgcct | gggagaccac | agcctacaga | ataaagatgg | cccagagcaa | 360 |
| gaaatacctg | tggttcagtc | catcccacac | ccctgctaca | acagcagcga | tgtggaggac | 420 |
| cacaaccatg | atctgatgct | tcttcaactg | cgtgaccagg | catccctggg | gtccaaagtg | 480 |
| aagcccatca | gcctggcaga | tcattgcacc | cagcctggcc | agaagtgcac | cgtctcaggc | 540 |
| tggggcactg | tcaccagtcc | ccgagagaat | tttcctgaca | ctctcaactg | tgcagaagta | 600 |
| aaaatctttc | cccagaagaa | gtgtgaggat | gcttacccg | ggcagatcac | agatggcatg | 660 |
| gtctgtgcag | gcagcagcaa | agggctgac | acgtgccagg | gcgattctgg | aggccccctg | 720 |

```
gtgtgtgatg gtgcactcca gggcatcaca tcctggggct cagacccctg tgggaggtcc      780
gacaaacctg gcgtctatac caacatctgc cgctacctgg actggatcaa gaagatcata      840
ggcagcaagg gctctagaca tcaccatcac catcactagc ggccgcttcc ctttagtgag      900
ggttaatgct tcgagcagac atgataagat acattgatga gtttggacaa accacaacta      960
gaatgcagtg aaaaaaatgc tttatttgtg aatttgtga tgctattgct ttatttgtaa      1020
ccattataag ctgcaataaa caagttgac                                         1049
```

<210> SEQ ID NO 10
<211> LENGTH: 1052
<212> TYPE: DNA
<213> ORGANISM: Artificial Sequence
<220> FEATURE:
<223> OTHER INFORMATION: Description of Artificial Sequence: Fusion gene
    with homo sapien serine protease catalytic domain

<400> SEQUENCE: 10

```
gaattcacca ccatggacag caaaggttcg tcgcagaaat cccgcctgct cctgctgctg       60
gtggtgtcaa atctactctt gtgccagggt gtggtctccg actacaagga cgacgacgac      120
gtggacgcgg ccgctcttgc tgcccccttt gatgatgatg acaagatcgt tggggggctac     180 aactgtctag aaaagcactc ccagccctgg caggcagccc tgttcgagaa gacgcggcta      240
ctctgtgggg cgacgctcat cgcccccaga tggctcctga cagcagccca ctgcctcaag      300
ccccgctaca tagttcacct ggggcagcac aacctccaga aggaggaggg ctgtgagcag      360
acccggacag ccactgagtc cttcccccac cccggcttca acaacagcct ccccaacaaa      420
gaccaccgca tgacatcat gctggtgaag atggcatcgc cagtctccat cacctgggct      480
gtgcgacccc tcaccctctc ctcacgctgt gtcactgctg caccagctg cctcatttcc     540 ggctggggca gcacgtccag cccccagtta cgcctgcctc acaccttgcg atgcgccaac     600
atcaccatca ttgagcacca gaagtgtgag aacgcctacc ccggcaacat cacagacacc     660
atggtgtgtg ccagcgtgca ggaagggggc aaggactcct gccagggtga ctccgggggc     720
cctctggtct gtaaccagtc tcttcaaggc attatctcct ggggccagga tccgtgtgcg     780
atcacccgaa agcctggtgt ctacacgaaa gtctgcaaat atgtggactg gatccaggag     840
acgatgaaga caattctag acatcaccat caccatcact agcggccgct tccctttagt      900
gagggttaat gcttcgagca gacatgataa gatacattga tgagtttgga caaccacaa      960 ctagaatgca gtgaaaaaaa tgctttattt gtgaaatttg tgatgctatt gctttatttg      1020
taaccattat aagctgcaat aaacaagttg ac                                   1052
```

<210> SEQ ID NO 11
<211> LENGTH: 328
<212> TYPE: PRT
<213> ORGANISM: Artificial Sequence
<220> FEATURE:
<223> OTHER INFORMATION: Description of Artificial Sequence: Fusion gene
    with homo sapien serine protease catalytic domain

<400> SEQUENCE: 11

```
Met Asp Ser Lys Gly Ser Ser Gln Lys Ser Arg Leu Leu Leu Leu Leu
 1               5                   10                  15

Val Val Ser Asn Leu Leu Leu Cys Gln Gly Val Val Ser Asp Tyr Lys
                20                  25                  30

Asp Asp Asp Asp Val Asp Ala Ala Ala Leu Ala Ala Pro Phe Asp Asp
            35                  40                  45
```

-continued

```
Asp Asp Lys Ile Val Gly Gly Tyr Ala Leu Glu Ala Gly Gln Trp Pro
 50                  55                  60
Trp Gln Val Ser Ile Thr Tyr Glu Gly Val His Val Cys Gly Gly Ser
 65                  70                  75                  80
Leu Val Ser Glu Gln Trp Val Leu Ser Ala His Cys Phe Pro Ser
                 85                  90                  95
Glu His His Lys Glu Ala Tyr Glu Val Lys Leu Gly Ala His Gln Leu
                100                 105                 110
Asp Ser Tyr Ser Glu Asp Ala Lys Val Ser Thr Leu Lys Asp Ile Ile
            115                 120                 125
Pro His Pro Ser Tyr Leu Gln Glu Gly Ser Gln Gly Asp Ile Ala Leu
        130                 135                 140
Leu Gln Leu Ser Arg Pro Ile Thr Phe Ser Arg Tyr Ile Arg Pro Ile
145                 150                 155                 160
Cys Leu Pro Ala Ala Asn Ala Ser Phe Pro Asn Gly Leu His Cys Thr
                165                 170                 175
Val Thr Gly Trp Gly His Val Ala Pro Ser Val Ser Leu Leu Thr Pro
            180                 185                 190
Lys Pro Leu Gln Gln Leu Glu Val Pro Leu Ile Ser Arg Glu Thr Cys
        195                 200                 205
Asn Cys Leu Tyr Asn Ile Asp Ala Lys Pro Glu Glu Pro His Phe Val
210                 215                 220
Gln Glu Asp Met Val Cys Ala Gly Tyr Val Glu Gly Gly Lys Asp Ala
225                 230                 235                 240
Cys Gln Gly Asp Ser Gly Gly Pro Leu Ser Cys Pro Val Glu Gly Leu
                245                 250                 255
Trp Tyr Leu Thr Gly Ile Val Ser Trp Gly Asp Ala Cys Gly Ala Arg
            260                 265                 270
Asn Arg Pro Gly Val Tyr Thr Leu Ala Ser Ser Tyr Ala Ser Trp Ile
        275                 280                 285
Gln Ser Lys Val Thr Glu Leu Gln Pro Arg Val Val Pro Gln Thr Gln
    290                 295                 300
Glu Ser Gln Pro Asp Ser Asn Leu Cys Gly Ser His Leu Ala Phe Ser
305                 310                 315                 320
Ser Arg His His His His His His
                325
```

<210> SEQ ID NO 12
<211> LENGTH: 319
<212> TYPE: PRT
<213> ORGANISM: Artificial Sequence
<220> FEATURE:
<223> OTHER INFORMATION: Description of Artificial Sequence: Fusion gene
      with homo sapien serine protease catalytic domain

<400> SEQUENCE: 12

```
Met Ala Phe Leu Trp Leu Leu Ser Cys Trp Ala Leu Leu Gly Thr Thr
  1               5                  10                  15
Phe Gly Cys Gly Val Pro Asp Tyr Lys Asp Asp Asp Ala Ala
                 20                  25                  30
Leu Ala Ala Pro Phe Asp Asp Asp Lys Ile Val Gly Gly Tyr Ala
             35                  40                  45
Leu Glu Ala Gly Gln Trp Pro Trp Gln Val Ser Ile Thr Tyr Glu Gly
         50                  55                  60
Val His Val Cys Gly Gly Ser Leu Val Ser Glu Gln Trp Val Leu Ser
```

```
                65                  70                  75                  80
Ala Ala His Cys Phe Pro Ser Glu His His Lys Glu Ala Tyr Glu Val
                        85                  90                  95

Lys Leu Gly Ala His Gln Leu Asp Ser Tyr Ser Glu Asp Ala Lys Val
                100                 105                 110

Ser Thr Leu Lys Asp Ile Ile Pro His Pro Ser Tyr Leu Gln Glu Gly
            115                 120                 125

Ser Gln Gly Asp Ile Ala Leu Leu Gln Leu Ser Arg Pro Ile Thr Phe
        130                 135                 140

Ser Arg Tyr Ile Arg Pro Ile Cys Leu Pro Ala Ala Asn Ala Ser Phe
145                 150                 155                 160

Pro Asn Gly Leu His Cys Thr Val Thr Gly Trp Gly His Val Ala Pro
                165                 170                 175

Ser Val Ser Leu Leu Thr Pro Lys Pro Leu Gln Gln Leu Glu Val Pro
                180                 185                 190

Leu Ile Ser Arg Glu Thr Cys Asn Cys Leu Tyr Asn Ile Asp Ala Lys
            195                 200                 205

Pro Glu Glu Pro His Phe Val Gln Glu Asp Met Val Cys Ala Gly Tyr
        210                 215                 220

Val Glu Gly Gly Lys Asp Ala Cys Gln Gly Asp Ser Gly Gly Pro Leu
225                 230                 235                 240

Ser Cys Pro Val Glu Gly Leu Trp Tyr Leu Thr Gly Ile Val Ser Trp
                245                 250                 255

Gly Asp Ala Cys Gly Ala Arg Asn Arg Pro Gly Val Tyr Thr Leu Ala
                260                 265                 270

Ser Ser Tyr Ala Ser Trp Ile Gln Ser Lys Val Thr Glu Leu Gln Pro
            275                 280                 285

Arg Val Val Pro Gln Thr Gln Glu Ser Gln Pro Asp Ser Asn Leu Cys
        290                 295                 300

Gly Ser His Leu Ala Phe Ser Ser Arg His His His His His
305                 310                 315

<210> SEQ ID NO 13
<211> LENGTH: 288
<212> TYPE: PRT
<213> ORGANISM: Artificial Sequence
<220> FEATURE:
<223> OTHER INFORMATION: Description of Artificial Sequence: Fusion gene
      with homo sapien serine protease catalytic domain

<400> SEQUENCE: 13

Met Asp Ser Lys Gly Ser Ser Gln Lys Ser Arg Leu Leu Leu Leu Leu
1               5                   10                  15

Val Val Ser Asn Leu Leu Leu Cys Gln Gly Val Val Ser Asp Tyr Lys
                20                  25                  30

Asp Asp Asp Asp Val Asp Ala Ala Leu Ala Ala Pro Phe Asp Asp
            35                  40                  45

Asp Asp Lys Ile Val Gly Gly Tyr Asn Cys Leu Glu Pro His Ser Gln
        50                  55                  60

Pro Trp Gln Ala Ala Leu Phe Gln Gly Gln Gln Leu Leu Cys Gly Gly
65                  70                  75                  80

Val Leu Val Gly Gly Asn Trp Val Leu Thr Ala Ala His Cys Lys Lys
                85                  90                  95

Pro Lys Tyr Thr Val Arg Leu Gly Asp His Ser Leu Gln Asn Lys Asp
                100                 105                 110
```

```
Gly Pro Glu Gln Glu Ile Pro Val Val Gln Ser Ile Pro His Pro Cys
            115                 120                 125

Tyr Asn Ser Ser Asp Val Glu Asp His Asn His Asp Leu Met Leu Leu
        130                 135                 140

Gln Leu Arg Asp Gln Ala Ser Leu Gly Ser Lys Val Lys Pro Ile Ser
145                 150                 155                 160

Leu Ala Asp His Cys Thr Gln Pro Gly Gln Lys Cys Thr Val Ser Gly
                165                 170                 175

Trp Gly Thr Val Thr Ser Pro Arg Glu Asn Phe Pro Asp Thr Leu Asn
            180                 185                 190

Cys Ala Glu Val Lys Ile Phe Pro Gln Lys Cys Glu Asp Ala Tyr
                195                 200                 205

Pro Gly Gln Ile Thr Asp Gly Met Val Cys Ala Gly Ser Ser Lys Gly
            210                 215                 220

Ala Asp Thr Cys Gln Gly Asp Ser Gly Gly Pro Leu Val Cys Asp Gly
225                 230                 235                 240

Ala Leu Gln Gly Ile Thr Ser Trp Gly Ser Asp Pro Cys Gly Arg Ser
                245                 250                 255

Asp Lys Pro Gly Val Tyr Thr Asn Ile Cys Arg Tyr Leu Asp Trp Ile
            260                 265                 270

Lys Lys Ile Ile Gly Ser Lys Gly Ser Arg His His His His His His
            275                 280                 285

<210> SEQ ID NO 14
<211> LENGTH: 289
<212> TYPE: PRT
<213> ORGANISM: Artificial Sequence
<220> FEATURE:
<223> OTHER INFORMATION: Description of Artificial Sequence: Fusion gene
      with homo sapien serine protease catalytic domain

<400> SEQUENCE: 14

Met Asp Ser Lys Gly Ser Ser Gln Lys Ser Arg Leu Leu Leu Leu Leu
  1               5                  10                  15

Val Val Ser Asn Leu Leu Leu Cys Gln Gly Val Val Ser Asp Tyr Lys
             20                  25                  30

Asp Asp Asp Asp Val Asp Ala Ala Leu Ala Ala Pro Phe Asp Asp
         35                  40                  45

Asp Asp Lys Ile Val Gly Gly Tyr Asn Cys Leu Glu Lys His Ser Gln
     50                  55                  60

Pro Trp Gln Ala Ala Leu Phe Glu Lys Thr Arg Leu Leu Cys Gly Ala
 65                  70                  75                  80

Thr Leu Ile Ala Pro Arg Trp Leu Leu Thr Ala Ala His Cys Leu Lys
                 85                  90                  95

Pro Arg Tyr Ile Val His Leu Gly Gln His Asn Leu Gln Lys Glu Glu
             100                 105                 110

Gly Cys Glu Gln Thr Arg Thr Ala Thr Glu Ser Phe Pro His Pro Gly
             115                 120                 125

Phe Asn Asn Ser Leu Pro Asn Lys Asp His Arg Asn Asp Ile Met Leu
         130                 135                 140

Val Lys Met Ala Ser Pro Val Ser Ile Thr Trp Ala Val Arg Pro Leu
145                 150                 155                 160

Thr Leu Ser Ser Arg Cys Val Thr Ala Gly Thr Ser Cys Leu Ile Ser
                165                 170                 175

Gly Trp Gly Ser Thr Ser Ser Pro Gln Leu Arg Leu Pro His Thr Leu
            180                 185                 190
```

```
Arg Cys Ala Asn Ile Thr Ile Ile Glu His Gln Lys Cys Glu Asn Ala
        195                 200                 205

Tyr Pro Gly Asn Ile Thr Asp Thr Met Val Cys Ala Ser Val Gln Glu
        210                 215                 220

Gly Gly Lys Asp Ser Cys Gln Gly Asp Ser Gly Gly Pro Leu Val Cys
225                 230                 235                 240

Asn Gln Ser Leu Gln Gly Ile Ile Ser Trp Gly Gln Asp Pro Cys Ala
                245                 250                 255

Ile Thr Arg Lys Pro Gly Val Tyr Thr Lys Val Cys Lys Tyr Val Asp
            260                 265                 270

Trp Ile Gln Glu Thr Met Lys Asn Asn Ser Arg His His His His
        275                 280                 285

His

<210> SEQ ID NO 15
<211> LENGTH: 9
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 15 ctagatagc                                                                9

<210> SEQ ID NO 16
<211> LENGTH: 9
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 16 ggccgctat                                                                9

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 17 ctagatacccc tacgatgtg cccgattacg cctagc                                 36

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18
ggccgctagg cgtaatcggg cacatcgtag gggtat                                 36

<210> SEQ ID NO 19
<211> LENGTH: 33
<212> TYPE: DNA
<213> ORGANISM: Artificial Sequence
<220> FEATURE:
```

<223> OTHER INFORMATION: Description of Artificial Sequence:
      oligonucleotide

<400> SEQUENCE: 19
ctagataccc ctacgatgtg cccgattacg ccg                          33

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 20
ctagcggcgt aatcgggcac atcgtagggg tat                          33

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 21
ctagacatca ccatcaccat cactagc                                 27

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 22
ggccgctagt gatggtgatg gtgatgt                                 27

<210> SEQ ID NO 23
<211> LENGTH: 34
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 23
tgaattcacc accatggaca gcaaaggttc gtcg                         34

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 24
cagaaagggt cccgcctgct cctgctgctg                              30

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence:

oligonucleotide

<400> SEQUENCE: 25
gtggtgtcaa atctactctt gtgccagggt                                30

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 26
gtggtctccg actacaagga cgacgacgac                                30

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 27
gtggacgcgg ccgcattatt a                                         21

<210> SEQ ID NO 28
<211> LENGTH: 35
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 28
taataatgcg gccgcgtcca cgtcgtcgtc gtcct                          35

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 29
tgtagtcgga gaccacaccc t                                         21

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 30
ggcacaagag tagatttgac accaccagca                                30

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 31
gcaggagcag gcgggaccct ttctgcgacg                                    30

<210> SEQ ID NO 32
<211> LENGTH: 29
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 32
aacctttgct gtccatggtg gtgaattca                                     29

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 33
aattcaccat gaatccactc ctgatcctta cctttgtggc                         40

<210> SEQ ID NO 34
<211> LENGTH: 40
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 34
ggccgccaca aagtaagga tcaggagtgg attcatggtg                          40

<210> SEQ ID NO 35
<211> LENGTH: 55
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 35
aattcaccac catggctttc ctctggctcc tctcctgctg ggccctcctg ggtac        55

<210> SEQ ID NO 36
<211> LENGTH: 47
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 36
ccaggagggc ccagcaggag aggagccaga ggaaagccat ggtggtg                 47

<210> SEQ ID NO 37
<211> LENGTH: 45
<212> TYPE: DNA
<213> ORGANISM: Artificial Sequence
<220> FEATURE:
<223> OTHER INFORMATION: Description of Artificial Sequence:
      oligonucleotide

<210> SEQ ID NO 37

<400> SEQUENCE: 37
caccttcggc tgcggggtcc ccgactacaa ggacgacgac gacgc            45

<210> SEQ ID NO 38
<211> LENGTH: 53
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 38
ggccgcgtcg tcgtcgtcct tgtagtcggg gaccccgcag ccgaaggtgg tac      53

<210> SEQ ID NO 39
<211> LENGTH: 29
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 39
gtggcggccg ctcttgctgc cccctttga                              29

<210> SEQ ID NO 40
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 40
ttctctagac agttgtagcc cccaacga                               28

<210> SEQ ID NO 41
<211> LENGTH: 55
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 41
ggccgctctt gctgccccct ttgatgatga tgacaagatc gttggggct atgct      55

<210> SEQ ID NO 42
<211> LENGTH: 55
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 42
ctagagcata gccccccaacg atcttgtcat catcatcaaa gggggcagca agagc      55

<210> SEQ ID NO 43
<211> LENGTH: 55
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 43
ggccgctctt gctgccccct ttgatgatga tgacaagatc gttgggggct attgt     55

<210> SEQ ID NO 44
<211> LENGTH: 55
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 44
ctagacaata gccccccaacg atcttgtcat catcatcaaa ggggcagca agagc     55

<210> SEQ ID NO 45
<211> LENGTH: 52
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 45
ggccgctctt gctgccccct ttatcgaggg gcgcattgtg gagggctcgg at        52

<210> SEQ ID NO 46
<211> LENGTH: 52
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 46
ctagatccga gccctccaca atgcgcccct cgataaaggg ggcagcaaga gc        52

<210> SEQ ID NO 47
<211> LENGTH: 32
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 47
agcagtctag aggccggtca gtggccctgg ca                              32

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 48
gctggtctag agctgaaggc caggtggc                                   28

<210> SEQ ID NO 49
<211> LENGTH: 29
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 49
ggtatctaga gcccttgctg cctatgatc                                29

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 50
actgtctaga accccattcg cagccttggc                               30

<210> SEQ ID NO 51
<211> LENGTH: 32
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 51
tcgatctaga aaagcactcc cagccctggc ag                            32

<210> SEQ ID NO 52
<211> LENGTH: 32
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 52
gtcctctaga attgttcttc atcgtctcct gg                            32

<210> SEQ ID NO 53
<211> LENGTH: 306
<212> TYPE: PRT
<213> ORGANISM: Artificial Sequence
<220> FEATURE:
<223> OTHER INFORMATION: Description of Artificial Sequence: Fusion gene
      of human protease F in CFEK2 zymogen vector

<400> SEQUENCE: 53

Met Ala Phe Leu Trp Leu Leu Ser Cys Trp Ala Leu Leu Gly Thr Thr
  1               5                  10                  15

Phe Gly Cys Gly Val Pro Asp Tyr Lys Asp Asp Asp Ala Ala Ala
                 20                  25                  30

Leu Ala Ala Pro Phe Asp Asp Asp Lys Ile Val Gly Gly Tyr Ala
             35                  40                  45

Leu Glu Leu Gly Arg Trp Pro Trp Gln Gly Ser Leu Arg Leu Trp Asp
     50                  55                  60

Ser His Val Cys Gly Val Ser Leu Leu Ser His Arg Trp Ala Leu Thr
 65                  70                  75                  80

Ala Ala His Cys Phe Glu Thr Tyr Ser Asp Leu Ser Asp Pro Ser Gly
                 85                  90                  95

Trp Met Val Gln Phe Gly Gln Leu Thr Ser Met Pro Ser Phe Trp Ser
            100                 105                 110

Leu Gln Ala Tyr Tyr Asn Arg Tyr Phe Val Ser Asn Ile Tyr Leu Ser
        115                 120                 125

Pro Arg Tyr Leu Gly Asn Ser Pro Tyr Asp Ile Ala Leu Val Lys Leu
    130                 135                 140

```
Ser Ala Pro Val Thr Tyr Thr Lys His Ile Gln Pro Ile Cys Leu Gln
145                 150                 155                 160

Ala Ser Thr Phe Glu Phe Glu Asn Arg Thr Asp Cys Trp Val Thr Gly
                165                 170                 175

Trp Gly Tyr Ile Lys Glu Asp Glu Ala Leu Pro Ser Pro His Thr Leu
                180                 185                 190

Gln Glu Val Gln Val Ala Ile Ile Asn Ser Met Cys Asn His Leu
        195                 200                 205

Phe Leu Lys Tyr Ser Phe Arg Lys Asp Ile Phe Gly Asp Met Val Cys
        210                 215                 220

Ala Gly Asn Ala Gln Gly Gly Lys Asp Ala Cys Phe Gly Asp Ser Gly
225                 230                 235                 240

Gly Pro Leu Ala Cys Asn Lys Asn Gly Leu Trp Tyr Gln Ile Gly Val
                245                 250                 255

Val Ser Trp Gly Val Gly Cys Gly Arg Pro Asn Arg Pro Gly Val Tyr
                260                 265                 270

Thr Asn Ile Ser His His Phe Glu Trp Ile Gln Lys Leu Met Ala Gln
                275                 280                 285

Ser Gly Met Ser Gln Pro Asp Pro Ser Trp Ser Arg His His His
        290                 295                 300

His His
305

<210> SEQ ID NO 54
<211> LENGTH: 284
<212> TYPE: PRT
<213> ORGANISM: Artificial Sequence
<220> FEATURE:
<223> OTHER INFORMATION: Description of Artificial Sequence: Human MH2
      protease in PFEK zymogen vector

<400> SEQUENCE: 54

Met Asp Ser Lys Gly Ser Ser Gln Lys Ser Arg Leu Leu Leu Leu
1               5                   10                  15

Val Val Ser Asn Leu Leu Leu Cys Gln Gly Val Val Ser Asp Tyr Lys
                20                  25                  30

Asp Asp Asp Asp Val Asp Ala Ala Leu Ala Ala Pro Phe Asp Asp
            35                  40                  45

Asp Asp Lys Ile Val Gly Gly Tyr Asn Cys Leu Glu Pro His Ser Gln
        50                  55                  60

Pro Trp Gln Ala Ala Leu Val Met Glu Asn Glu Leu Phe Cys Ser Gly
65                  70                  75                  80

Val Leu Val His Pro Gln Trp Val Leu Ser Ala Ala His Cys Phe Gln
                85                  90                  95

Asn Ser Tyr Thr Ile Gly Leu Gly Leu His Ser Leu Glu Ala Asp Gln
                100                 105                 110

Glu Pro Gly Ser Gln Met Val Glu Ala Ser Leu Ser Val Arg His Pro
            115                 120                 125

Glu Tyr Asn Arg Pro Leu Leu Ala Asn Asp Leu Met Leu Ile Lys Leu
        130                 135                 140

Asp Glu Ser Val Ser Glu Ser Asp Thr Ile Arg Ser Ile Ser Ile Ala
145                 150                 155                 160

Ser Gln Cys Pro Thr Ala Gly Asn Ser Cys Leu Val Ser Gly Trp Gly
                165                 170                 175

Leu Leu Ala Asn Gly Arg Met Pro Thr Val Leu Gln Cys Val Asn Val
                180                 185                 190
```

Ser Val Ser Glu Val Cys Ser Lys Leu Tyr Asp Pro Leu Tyr
    195                 200                 205

His Pro Ser Met Phe Cys Ala Gly Gly His Asp Gln Lys Asp Ser
    210                 215                 220

Cys Asn Gly Asp Ser Gly Pro Leu Ile Cys Asn Gly Tyr Leu Gln
225                 230                 235                 240

Gly Leu Val Ser Phe Gly Lys Ala Pro Cys Gly Gln Val Gly Val Pro
                245                 250                 255

Gly Val Tyr Thr Asn Leu Cys Lys Phe Thr Glu Trp Ile Glu Lys Thr
            260                 265                 270

Val Gln Ala Ser Ser Arg His His His His His His
        275                 280

<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 55
aggatctaga gccgcactcg cagccctggc                                      30

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 56
cccatctaga actggcctgg acggttttct                                      30

<210> SEQ ID NO 57
<211> LENGTH: 32
<212> TYPE: DNA
<213> ORGANISM: Artificial Sequence
<220> FEATURE:
<223> OTHER INFORMATION: Description of Artificial Sequence: PCR primer

<400> SEQUENCE: 57
aggatctaga actcgggcgt tggccgtggc ag                                   32

<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 58
agagtctaga ccaggagggg tctggctggg                                      30

<210> SEQ ID NO 59
<211> LENGTH: 1103
<212> TYPE: DNA
<213> ORGANISM: Artificial Sequence
<220> FEATURE:
<223> OTHER INFORMATION: Description of Artificial Sequence: Nucleic
      acid sequence of human protease F in CFEK2 zymogen
      vector

<400> SEQUENCE: 59

-continued

```
gaattcacca ccatggcttt cctctggctc ctctcctgct gggccctcct gggtaccacc      60
ttcggctgcg gggtccccga ctacaaggac gacgacgacg cggccgctct tgctgccccc     120
tttgatgatg atgacaagat cgttgggggc tatgctctag aactcgggcg ttggccgtgg     180
caggggagcc tgcgcctgtg ggattcccac gtatgcggag tgagcctgct cagccaccgc     240
tgggcactca cggcggcgca ctgctttgaa acctatagtg accttagtga tccctccggg     300
tggatggtcc agtttggcca gctgacttcc atgccatcct tctggagcct gcaggcctac     360
tacaaccgtt acttcgtatc gaatatctat ctgagccctc gctacctggg gaattcaccc     420
tatgacattg ccttggtgaa gctgtctgca cctgtcacct acactaaaca catccagccc     480
atctgtctcc aggcctccac atttgagttt gagaaccgga cagactgctg ggtgactggc     540
tgggggtaca tcaaagagga tgaggcactg ccatctcccc acaccctcca ggaagttcag     600
gtcgccatca taaacaactc tatgtgcaac cacctcttcc tcaagtacag tttccgcaag     660
gacatctttg agacatggt tgtgctggc aatgcccaag gcgggaagga tgcctgcttc     720
ggtgactcag gtggaccctt ggcctgtaac aagaatggac tgtggtatca gattggagtc     780
gtgagctggg gagtgggctg tggtcggccc aatcggcccg tgtctacac caatatcagc     840
caccactttg agtggatcca gaagctgatg gcccagagtg gcatgtccca gccagacccc     900
tcctggtcta gacatcacca tcaccatcac tagcggccgc ttccctttag tgagggttaa     960
tgcttcgagc agacatgata agatacattg atgagtttgg acaaaccaca actagaatgc    1020
agtgaaaaaa atgctttatt tgtgaaattt gtgatgctat tgctttattt gtaaccatta    1080
taagctgcaa taaacaagtt gac                                            1103
```

<210> SEQ ID NO 60
<211> LENGTH: 1037
<212> TYPE: DNA
<213> ORGANISM: Artificial Sequence
<220> FEATURE:
<223> OTHER INFORMATION: Description of Artificial Sequence: Nucleic acid sequence of human MH2 protease in PFEK zymogen vector

<400> SEQUENCE: 60

```
gaattcacca ccatggacag caaaggttcg tcgcagaaat cccgcctgct cctgctgctg      60
gtggtgtcaa atctactctt gtgccagggt gtggtctccg actacaagga cgacgacgac     120
gtggacgcgg ccgctcttgc tgccccctt gatgatgatg acaagatcgt tggggggctac     180
aactgtctag agccgcactc gcagccctgg caggcggcac tggtcatgga aaacgaattg     240
ttctgctcgg gcgtcctggt gcatccgcag tgggtgctgt cagccgcaca ctgtttccag     300
aactcctaca ccatcgggct gggcctgcac agtcttgagg ccgaccaaga gccagggagc     360
cagatggtgg aggccagcct ctccgtacgg cacccagagt acaacagacc cttgctcgct     420
aacgacctca tgctcatcaa gttggacgaa tccgtgtccg agtctgacac catccggagc     480
atcagcattg cttcgcagtg ccctaccgcg gggaactctt gcctcgtttc tggctggggt     540
ctgctggcga acggcagaat gcctaccgtg ctgcagtgcg tgaacgtgtc ggtggtgtct     600
gaggaggtct gcagtaagct ctatgacccg ctgtaccacc ccagcatgtt ctgcgccggc     660
ggagggcacg accagaagga ctcctgcaac ggtgactctg gggggcccct gatctgcaac     720
gggtacttgc agggccttgt gtcttttcgga aagcccccgt gtggccaagt tggcgtgcca     780
ggtgtctaca ccaacctctg caaattcact gagtggtaga agaaaaccgt ccaggccagt    840
tctagacatc accatcacca tcactagcgg ccgcttccct ttagtgaggg ttaatgcttc     900
```

```
gagcagacat gataagatac attgatgagt ttggacaaac cacaactaga atgcagtgaa        960
aaaaatgctt tatttgtgaa atttgtgatg ctattgcttt atttgtaacc attataagct       1020
gcaataaaca agttgac                                                      1037
```